(12) United States Patent
Guo et al.

(10) Patent No.: US 9,512,440 B2
(45) Date of Patent: Dec. 6, 2016

(54) MODULATION OF RECEPTOR-LIKE KINASES FOR PROMOTION OF PLANT GROWTH

(71) Applicant: IOWA STATE UNIVERSITY RESEARCH FOUNDATION, INC., Ames, IA (US)

(72) Inventors: Hongqing Guo, Ames, IA (US); Yanhai Yin, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 786 days.

(21) Appl. No.: 13/773,150

(22) Filed: Feb. 21, 2013

(65) Prior Publication Data

US 2013/0239254 A1 Sep. 12, 2013

Related U.S. Application Data

(63) Continuation of application No. 12/928,233, filed on Dec. 7, 2010, now abandoned.

(60) Provisional application No. 61/283,674, filed on Dec. 7, 2009.

(51) Int. Cl.
*C12N 15/87* (2006.01)
*C12N 15/82* (2006.01)

(52) U.S. Cl.
CPC ....... *C12N 15/8261* (2013.01); *C12N 15/8281* (2013.01); *C12N 15/8298* (2013.01)

(58) Field of Classification Search
None
See application file for complete search history.

(56) References Cited

U.S. PATENT DOCUMENTS

| | | |
|---|---|---|
| 6,501,008 B1 | 12/2002 | Nevins et al. |
| 6,534,313 B1 | 3/2003 | Neff et al. |
| 7,034,205 B2 | 4/2006 | Neff et al. |
| 7,265,264 B2 | 9/2007 | Neff |

OTHER PUBLICATIONS

Bowie et al, Science 247:1306-1310, 1990.*
McConnell et al, Nature 411 (6838):709-713, 2001.*
Lindner et al (2012, Current Opinion in Plant Biology 15 (6): 659-669).*
Escobar-Restrepo, Juan-Miguel et al., "The FERONIA Receptor-like Kinase Mediates Male-Female Interactions During Pollen Tube Reception", Science 317, 656 (2007).
Guo, Hongqing et al., "A family of receptor-like kinases are regulated by BES1 and involved in plant growth in Arabidopsis thaliana", Plant Signaling & Behavior 4:8, 1-3; Aug. 2009.
Guo, Hongqing et al., "Three related receptor-like kinases are required for optimal cell elongation in Arabidopsis thaliana", PNAS Early Edition, www.pnas.org/cgi/doi/10.1073/pnas.0812346106, pp. 1-6, published online Apr. 21, 2009.
Hematy, Kian et al., "A Receptor-like Kinase Mediates the Response of Arabidopsis Cells to the Inhibition of Cellulose Synthesis", Current Biology 17, 922-931, Jun. 5, 2007.
Weigel, Detlef et al., "Activation Tagging in Arabidopsis", Plant Physiology, Apr. 2000, vol. 122, pp. 1003-1013.
TAIR Accession: Locus:2075346; Representative Gene Model AT3G46290.1, www.arabidopsis.org/servlets/TairObject?accession=Locus:2075346&showAllNote=true[Aug. 18, 2009 4:48:11 PM].
Hardie et al., Annu. Rev. Plant Physiol. Plant Mol. Biol. (1999) 50: 97-131.
Guo et al. (PNAS 2009a) 106; 7648-7653.
Guo et al. Plant Signal. Behav. (2009b) 4: 784-786.
Boisson-Demier et al., J. Exp. Bot. (2011) 62:1581-1591.
Alonso et al., Science (2003) 301:653-657.
Thilmony et al., (1995) Plant Cell 7:1529-1536.
Jefferson et al. (1987) EMBO J. 6:3901-3907.
Wang et al., (2001) Nature 410:380-383.
Friedrichsen et al. (2000) Plant Phys. 123:1247-1255.

* cited by examiner

*Primary Examiner* — Stuart F Baum
(74) *Attorney, Agent, or Firm* — McKee, Voorhees & Sease, PLC

(57) ABSTRACT

The invention provides the disclosure of a novel plant growth pathway involving several receptor like kinases. The pathway was shown to work largely independent of brassinosteroids and involves several members of the CrRLK1L family of receptor kinases. According to the invention, HERK1, HERK2, FER, THE1 and the brassinosteroid BES1 may be modulated to influence plant growth and elongation. The invention includes methods, and transformed plants, cells tissues and seeds with increased cellular elongation and other related yield traits.

Figure 1:
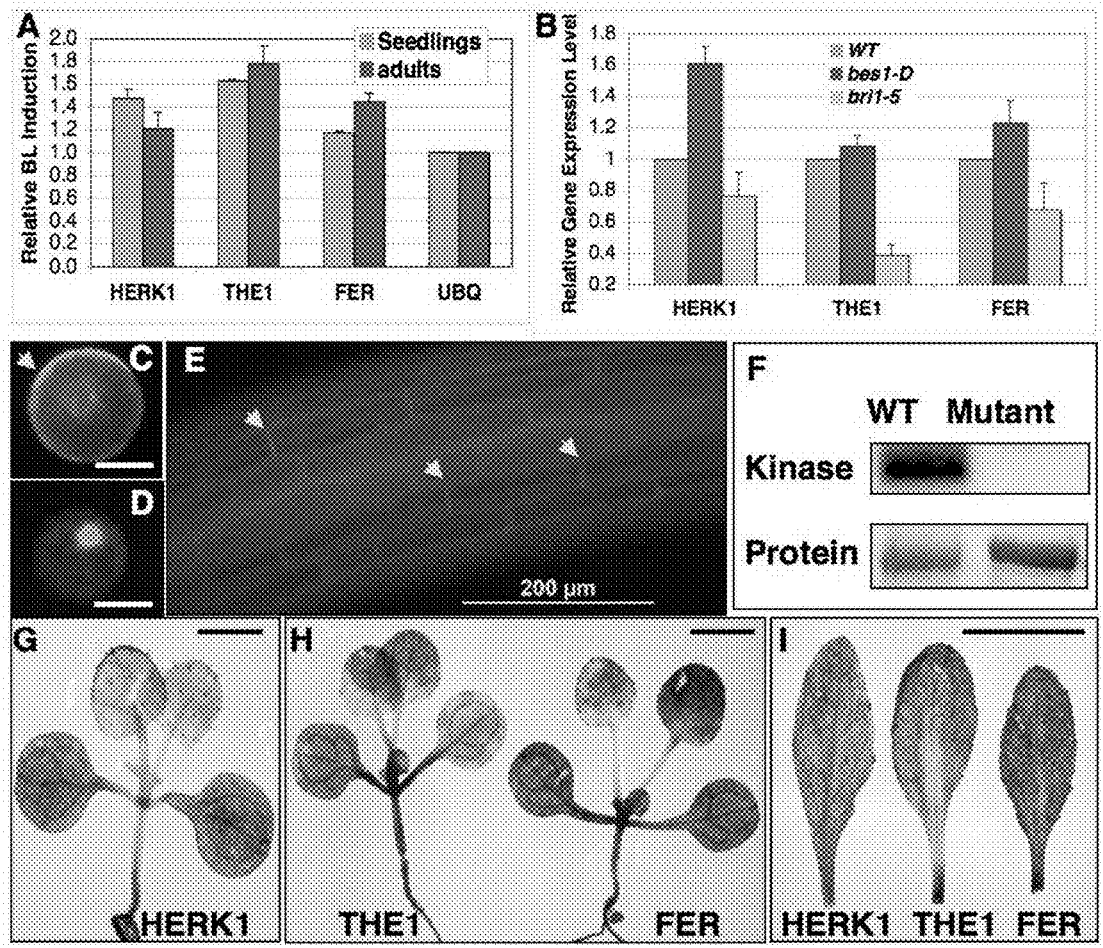

9 Claims, 11 Drawing Sheets
(11 of 11 Drawing Sheet(s) Filed in Color)

SEQUENCE LISTING

```
<160> NUMBER OF SEQ ID NOS: 8

<210> SEQ ID NO 1
<211> LENGTH: 3123
<212> TYPE: DNA
<213> ORGANISM: Arabidopsis thaliana

<400> SEQUENCE: 1
actcattaat tgattttctc tctctctccc ccaaaatatc tctgtcttct ccaaaaactc      60
tctccgattt catcgcttag ggtttcttcc ccgattcttc agatctgaga agaagatctt     120
cccggagaag tgctcttgat cgatgaagat cacagaggga cgattccgtc tctctcttct     180
tcttcttctt cttctcatat ctgcagcaac tttaatctca gctgctgatt actctccaac     240
agagaaaatc ctattgaatt gcggtggtgg tgcttctaat ctaaccgaca cagataaccg     300
tatatggatc tccgatgtca aatcaaaatt cttatcatct tcctctgaag actctaaaac     360
```

```
atcaccagcg ttaacacaag atccttccgt tcccgaagtt ccttacatga cggcgagagt    420
tttccgatct cctttcactt acactttccc tgtagcatca ggtcgtaaat tcgtgcgtct    480
ctacttctac ccaaactcgt acgacggtct caacgctacc aactcgttat tctccgtctc    540
ctttggtcct tacactcttc tcaagaattt cagtgcttct cagacggcgg aggcgttgac    600
ttacgctttc atcatcaagg agtttgttgt caacgttgaa ggtggaacgt tgaacatgac    660
gtttacaccg gaatcagctc cgtctaatgc gtatgcgttt gttaatggga ttgaggttac    720
ttcaatgcct gatatgtata gtagtactga tgggactttg actatggttg gatcatctgg    780
ctctgttact attgataaca gtactgctct tgagaatgtg tataggctca atgttggagg    840
gaatgatatc tcgccttccg cggatacggg tttgtatagg tcgtggtatg atgatcagcc    900
ttatatattt ggtgcaggac ttggtattcc agagactgct gatcccaaca tgacgattaa    960
gtatcctacg gggactccta cttatgttgc tcctgtggat gtttattcaa ccgcgaggtc   1020
tatgggtcca acagctcaga tcaatctcaa ctacaatctt acttggattt tcagcattga   1080
ctctggtttc acttaccttg ttagacttca tttctgtgag gtttcttcga atatcactaa   1140
gatcaaccaa cgggtgttta caatctacct caacaatcaa actgctgagc ctgaagctga   1200
tgtgattgct tggactagtt caaacggggt tccgtttcac aaggattacg tggtgaatcc   1260
tccagaggga aatggacagc aagatttgtg gcttgctctt catcctaacc cagttaacaa   1320
gccggagtat tatgattctc ttcttaatgg agtggagata ttcaagatga atacttctga   1380
tggtaatctg gctggtacca atcctatacc tggtccacag gtgactgctg atccatctaa   1440
agtcctacgc ccgactacta ggaaatcgaa aagcaatacg gctattattg caggcgcagc   1500
cagtggtgca gttgttctgg cccttatcat tgggttttgt gtgtttggtg cttaccgcag   1560
acgtaagcgt ggtgattacc agcctgctag tgatgcaaca tcagggtggc ttccactatc   1620
tctgtatgga aactcacatt ctgctggctc ggcgaagaca aacacaacag gaagttatgc   1680
ctcgtccctt ccgtcaaatc tttgccgtca cttctcgttt gctgagatca agctgccac    1740 taaaaacttt tgatgagtcc gggtgcttgg tgttggtggt ttcggcaagg tttacagagg   1800
agagattgat ggcggaacta caaaggtagc catcaagaga ggcaacccaa tgtccgagca   1860
aggtgtacat gagttccaga ctgagattga aatgctttca aagcttagac atcgtcatct   1920
tgtgtccttg attggatact gtgaagagaa ctgcgaaatg atcttagtct atgattacat   1980
ggctcatggt acaatgaggg agcatctcta caaaacccag aatccttctc ttccatggaa   2040
gcaacgtctt gagatatgca ttggagcagc ccgaggttta cactatctac acactggtgc   2100
aaaacacaca atcatccata gagatgtgaa gacaacaaac attctattgg atgagaaatg   2160
ggtggccaag gtctctgatt ttggtctatc gaagactggt cctacactag accacacaca   2220
cgtaagcaca gttgtgaaag gaagtttcgg ttatcttgac ccagagtatt tcagacggca   2280
gcaactgact gagaaatccg atgtctactc ctttggcgtt gttctattcg aagctctatg   2340
cgctcgtcca gccttgaacc caacacttgc aaaggaacaa gtgagcttag ctgagtgggc   2400
accatactgc tacaagaaag gcatgctaga tcaaatcgtt gatccctacc tcaagggcaa   2460
gatcacacca gaatgcttca aaagtttgc tgaaccgcg atgaagtgtg ttctagacca   2520
gggcattgag agaccatcaa tgggagatgt tctgtggaac ttagaatttg cgttgcagct   2580
ccaggaaagc gcagaagaga acggaaaagg agtatgcggt gacatggaca tggatgagat   2640
taagtacgat gatggaaact gtaaaggaaa gaacgacaag agttctgatg tgtatgaagg   2700
```

```
gaatgtgacg gactcgagga gcagtggaat agatatgagc atcggtggta ggagtttggc    2760
cagcgaagat tcagatggac tcactccaag tgctgtgttt tctcagatca tgaatccaaa    2820
gggacgttag agaagtctta taacacggta caacactact acctttctaa accggctcca    2880
tccaaaggag accggttcgt ttctcttttt tatatttttt ttcctcttaa ctatttatta    2940
ttattctctt tgctgttatt tatttagaat tttggatttg tgtatttgat gccacgatgg    3000
agagtgtaaa aataatgta tttttttttc ttctttctac aaaaacatta aacatgaatc     3060
gcgtcaatgt actatttggt ttgttatcta taacgttttt ggtaattgtt gcatctttac    3120
tct                                                                  3123
```

<210> SEQ ID NO 2
<211> LENGTH: 895
<212> TYPE: PRT
<213> ORGANISM: Arabidopsis thaliana

<400> SEQUENCE: 2

Met Lys Ile Thr Glu Gly Arg Phe Arg Leu Ser Leu Leu Leu Leu Leu
1               5                   10                  15

Leu Leu Ile Ser Ala Ala Thr Leu Ile Ser Ala Ala Asp Tyr Ser Pro
            20                  25                  30

Thr Glu Lys Ile Leu Leu Asn Cys Gly Gly Gly Ala Ser Asn Leu Thr
        35                  40                  45

Asp Thr Asp Asn Arg Ile Trp Ile Ser Asp Val Lys Ser Lys Phe Leu
    50                  55                  60

Ser Ser Ser Ser Glu Asp Ser Lys Thr Ser Pro Ala Leu Thr Gln Asp
65                  70                  75                  80

Pro Ser Val Pro Glu Val Pro Tyr Met Thr Ala Arg Val Phe Arg Ser
                85                  90                  95

Pro Phe Thr Tyr Thr Phe Pro Val Ala Ser Gly Arg Lys Phe Val Arg
            100                 105                 110

Leu Tyr Phe Tyr Pro Asn Ser Tyr Asp Gly Leu Asn Ala Thr Asn Ser
        115                 120                 125

Leu Phe Ser Val Ser Phe Gly Pro Tyr Thr Leu Leu Lys Asn Phe Ser
    130                 135                 140

Ala Ser Gln Thr Ala Glu Ala Leu Thr Tyr Ala Phe Ile Ile Lys Glu
145                 150                 155                 160

Phe Val Val Asn Val Glu Gly Gly Thr Leu Asn Met Thr Phe Thr Pro
                165                 170                 175

Glu Ser Ala Pro Ser Asn Ala Tyr Ala Phe Val Asn Gly Ile Glu Val
            180                 185                 190

Thr Ser Met Pro Asp Met Tyr Ser Ser Thr Asp Gly Thr Leu Thr Met
        195                 200                 205

Val Gly Ser Ser Gly Ser Val Thr Ile Asp Asn Ser Thr Ala Leu Glu
    210                 215                 220

Asn Val Tyr Arg Leu Asn Val Gly Gly Asn Asp Ile Ser Pro Ser Ala
225                 230                 235                 240

Asp Thr Gly Leu Tyr Arg Ser Trp Tyr Asp Asp Gln Pro Tyr Ile Phe
                245                 250                 255

Gly Ala Gly Leu Gly Ile Pro Glu Thr Ala Asp Pro Asn Met Thr Ile
            260                 265                 270

Lys Tyr Pro Thr Gly Thr Pro Thr Tyr Val Ala Pro Val Asp Val Tyr
        275                 280                 285

Ser Thr Ala Arg Ser Met Gly Pro Thr Ala Gln Ile Asn Leu Asn Tyr

-continued

```
            290                 295                 300
Asn Leu Thr Trp Ile Phe Ser Ile Asp Ser Gly Phe Thr Tyr Leu Val
305                 310                 315                 320
Arg Leu His Phe Cys Glu Val Ser Ser Asn Ile Thr Lys Ile Asn Gln
                325                 330                 335
Arg Val Phe Thr Ile Tyr Leu Asn Asn Gln Thr Ala Glu Pro Glu Ala
                340                 345                 350
Asp Val Ile Ala Trp Thr Ser Ser Asn Gly Val Pro Phe His Lys Asp
                355                 360                 365
Tyr Val Val Asn Pro Pro Glu Gly Asn Gly Gln Gln Asp Leu Trp Leu
370                 375                 380
Ala Leu His Pro Asn Pro Val Asn Lys Pro Glu Tyr Tyr Asp Ser Leu
385                 390                 395                 400
Leu Asn Gly Val Glu Ile Phe Lys Met Asn Thr Ser Asp Gly Asn Leu
                405                 410                 415
Ala Gly Thr Asn Pro Ile Pro Gly Pro Gln Val Thr Ala Asp Pro Ser
                420                 425                 430
Lys Val Leu Arg Pro Thr Thr Arg Lys Ser Lys Ser Asn Thr Ala Ile
                435                 440                 445
Ile Ala Gly Ala Ala Ser Gly Ala Val Val Leu Ala Leu Ile Ile Gly
                450                 455                 460
Phe Cys Val Phe Gly Ala Tyr Arg Arg Arg Lys Arg Gly Asp Tyr Gln
465                 470                 475                 480
Pro Ala Ser Asp Ala Thr Ser Gly Trp Leu Pro Leu Ser Leu Tyr Gly
                485                 490                 495
Asn Ser His Ser Ala Gly Ser Ala Lys Thr Asn Thr Thr Gly Ser Tyr
                500                 505                 510
Ala Ser Ser Leu Pro Ser Asn Leu Cys Arg His Phe Ser Phe Ala Glu
                515                 520                 525
Ile Lys Ala Ala Thr Lys Asn Phe Asp Glu Ser Arg Val Leu Gly Val
530                 535                 540
Gly Gly Phe Gly Lys Val Tyr Arg Gly Glu Ile Asp Gly Gly Thr Thr
545                 550                 555                 560
Lys Val Ala Ile Lys Arg Gly Asn Pro Met Ser Glu Gln Gly Val His
                565                 570                 575
Glu Phe Gln Thr Glu Ile Glu Met Leu Ser Lys Leu Arg His Arg His
                580                 585                 590
Leu Val Ser Leu Ile Gly Tyr Cys Glu Glu Asn Cys Glu Met Ile Leu
                595                 600                 605
Val Tyr Asp Tyr Met Ala His Gly Thr Met Arg Glu His Leu Tyr Lys
610                 615                 620
Thr Gln Asn Pro Ser Leu Pro Trp Lys Gln Arg Leu Glu Ile Cys Ile
625                 630                 635                 640
Gly Ala Ala Arg Gly Leu His Tyr Leu His Thr Gly Ala Lys His Thr
                645                 650                 655
Ile Ile His Arg Asp Val Lys Thr Thr Asn Ile Leu Leu Asp Glu Lys
                660                 665                 670
Trp Val Ala Lys Val Ser Asp Phe Gly Leu Ser Lys Thr Gly Pro Thr
                675                 680                 685
Leu Asp His Thr His Val Ser Thr Val Val Lys Gly Ser Phe Gly Tyr
                690                 695                 700
Leu Asp Pro Glu Tyr Phe Arg Arg Gln Gln Leu Thr Glu Lys Ser Asp
705                 710                 715                 720
```

```
Val Tyr Ser Phe Gly Val Val Leu Phe Glu Ala Leu Cys Ala Arg Pro
            725                 730                 735

Ala Leu Asn Pro Thr Leu Ala Lys Glu Gln Val Ser Leu Ala Glu Trp
            740                 745                 750

Ala Pro Tyr Cys Tyr Lys Lys Gly Met Leu Asp Gln Ile Val Asp Pro
            755                 760                 765

Tyr Leu Lys Gly Lys Ile Thr Pro Glu Cys Phe Lys Lys Phe Ala Glu
            770                 775                 780

Thr Ala Met Lys Cys Val Leu Asp Gln Gly Ile Glu Arg Pro Ser Met
785                 790                 795                 800

Gly Asp Val Leu Trp Asn Leu Glu Phe Ala Leu Gln Leu Gln Glu Ser
            805                 810                 815

Ala Glu Glu Asn Gly Lys Gly Val Cys Gly Asp Met Asp Met Asp Glu
            820                 825                 830

Ile Lys Tyr Asp Asp Gly Asn Cys Lys Gly Lys Asn Asp Lys Ser Ser
            835                 840                 845

Asp Val Tyr Glu Gly Asn Val Thr Asp Ser Arg Ser Ser Gly Ile Asp
            850                 855                 860

Met Ser Ile Gly Gly Arg Ser Leu Ala Ser Glu Asp Ser Asp Gly Leu
865                 870                 875                 880

Thr Pro Ser Ala Val Phe Ser Gln Ile Met Asn Pro Lys Gly Arg
            885                 890                 895

<210> SEQ ID NO 3
<211> LENGTH: 2789
<212> TYPE: DNA
<213> ORGANISM: Arabidopsis thaliana

<400> SEQUENCE: 3
atggtgttca caaaatcatt acttgttctt ctttggttcc tctcttgtta cactactact      60
acttcatcag ctttgtttaa tccgccagac aattacttga tctcttgtgg ctcatcacaa     120
aacataactt tccaaaacag aatctttgtt ccagattcac tccactcttc tcttgtactc     180
aaaatcggaa actcttctgt tgcaacatca actacttcca acaattcaac caattccatc     240
taccaaaccg ctcgtgtttt ctccagttta gcttcttaca gattcaaaat cacttcttta     300
ggtcgacatt ggatccgtct tcatttctca cctatcaaca actctacttg aacttaaacc     360
tctgcttcaa tcactgtcgt aacagaagac ttcgtgctct tgaacaactt ctccttcaac     420
aacttcaacg ttcttacat cttcaaagag tacacagtca atgtcacttc agagttcttg      480
actttaagtt tcattccttc aaacaattcg gtggtctttg tcaacgctat tgaagttgtc     540
tctgttccgg ataatcttat ccctgatcaa gctttggcgt taaacccttc aacaccattt     600
agtggtctct ctctgcttgc atttgaaaca gtctacagat taaatatggg aggaccattg     660
ttgacttctc aaaacgatac attggggaga caatgggata tgatgcaga gtatcttcat       720 gtgaacagct ctgttcttgt tgtaacggcg aatccttctt cgattaagta ctctccttct     780
gtgactcaag aaacagctcc taacatggtt tatgcaactg ctgatacaat gggtgatgct     840
aatgttgcga gtccaagttt taatgttact tgggttcttc ctgttgatcc agacttcagg     900
tactttgttc gtgttcattt ctgtgatatt gtgagtcaag ctttgaacac gcttgttttc     960
aatctttatg tgaatgatga tcttgctctt ggaagtcttg atctctctac gttgactaat    1020
ggtcttaaag ttccttactt taaggatttt atctccaatg ttctgttga atcttccggt     1080 gttttaaccg ttagcgttgg acctgattca caagctgata tcactaatgc gactatgaat    1140
```

```
gggttagagg ttttgaagat tagtaacgaa gctaagagct taagtggtgt ttcttcggtt    1200
aagtcgttac ttccgggagg atcaggttct aagagcaaga agaaggcagt gatcattggt    1260
tctttggttg gtgcggttac attgattctg ctgattgctg tttgttgcta ttgctgtttg    1320
gttgcttcaa ggaagcagag gtcgacgagt cctcaagaag gcggtaatgg acatccgtgg    1380
ttgccattac ctttatatgg actctctcag actcttacta aatcaaccgc ttctcacaag    1440
agtgccacag ctagttgcat tcattagct tctactcatc ttggacgttg ctttatgttt     1500
caagaaatca tggacgctac taataagttc gatgagagtt cgttgcttgg ggttggtgga    1560
tttggccgcg tttataaagg aactttagaa gacgggacta agtcgcggt taaaagaggt     1620 aacccgagat cagaacaagg tatggctgag ttcagaacag agattgaaat gctgtcaaaa    1680
ctcagacatc gacatctcgt ctctcttatc ggttactgcg acgagaggtc tgaaatgata    1740
ctggtctatg agtacatggc gaatggaccg ttgaggagtc atctatatgg agctgatctt    1800
cctccattgt cttggaaaca aagactcgag atttgcatcg gtgcagcgag aggattacat    1860
tatctacaca ccggtgcatc gcagagcatt atacaccgtg atgttaaaac cacgaatatc    1920
ttactcgacg agaatctagt cgccaaagtt gcagactttg gactatccaa accggccct    1980 tcgctcgatc aaacacacgt gagcacggcg gttaaggaa gctttggtta tctagacccg     2040
gaatacttca ggagacagca gttaacgag aaatcagacg tttattcgtt tggtgttgta    2100
ctaatggaag tactctgttg tagaccggct ttaaacccgg tattacctag agaacaagtg     2160
aacatagcgg aatgggcaat ggcgtggcag aaaaagggtc tgctagatca aatcatggac    2220
agtaacttaa ccgggaaggt gaaccctgcc tcgttgaaga aatttggaga aaccgcagag    2280
aaatgtttag cggaatacgg tgtgaccgg ccttctatgg gagatgtatt gtggaatttg     2340
gagtacgcgt tacagctaga agaaacatct tcggctttga tggagcctga tgacaatagt    2400
acaaaccaca ttccagggat tccaatggcg ccaatggaac cgtttgataa cagtatgagt    2460
ataatcgata gaggaggagt aaattcgggg accgggactg atgatgatgc ggaagacgcg    2520
actactagtg cggtgttttc gcagcttgtt catcctcgtg gaaggtagaa gaagaacaca    2580
tttggtgaaa acaacagcag agacagacat tgtttgtttt tgaaaaattt atagaaagaa    2640
agttatttat tgaagacttt tgggaacaaa caacaaaatg attcattcag catttatttt    2700
cgatttttta cggtgtattt gttttgtaat atagtgagta ctgatgtttt aaagcaaatc    2760
atgaatcaga atgtgattat atatcttaa                                       2789
```

<210> SEQ ID NO 4
<211> LENGTH: 855
<212> TYPE: PRT
<213> ORGANISM: Arabidopsis thaliana

<400> SEQUENCE: 4

```
Met Val Phe Thr Lys Ser Leu Leu Val Leu Leu Trp Phe Leu Ser Cys
1               5                   10                  15

Tyr Thr Thr Thr Thr Ser Ser Ala Leu Phe Asn Pro Pro Asp Asn Tyr
                20                  25                  30

Leu Ile Ser Cys Gly Ser Ser Gln Asn Ile Thr Phe Gln Asn Arg Ile
            35                  40                  45

Phe Val Pro Asp Ser Leu His Ser Ser Leu Val Leu Lys Ile Gly Asn
        50                  55                  60

Ser Ser Val Ala Thr Ser Thr Thr Ser Asn Asn Ser Thr Asn Ser Ile
65                  70                  75                  80
```

-continued

Tyr Gln Thr Ala Arg Val Phe Ser Ser Leu Ala Ser Tyr Arg Phe Lys
                85                  90                  95
Ile Thr Ser Leu Gly Arg His Trp Ile Arg Leu His Phe Ser Pro Ile
            100                 105                 110
Asn Asn Ser Thr Trp Asn Leu Thr Ser Ala Ser Ile Thr Val Val Thr
            115                 120                 125
Glu Asp Phe Val Leu Leu Asn Asn Phe Ser Phe Asn Asn Phe Asn Gly
    130                 135                 140
Ser Tyr Ile Phe Lys Glu Tyr Thr Val Asn Val Thr Ser Glu Phe Leu
145                 150                 155                 160
Thr Leu Ser Phe Ile Pro Ser Asn Asn Ser Val Val Phe Val Asn Ala
                165                 170                 175
Ile Glu Val Val Ser Val Pro Asp Asn Leu Ile Pro Asp Gln Ala Leu
            180                 185                 190
Ala Leu Asn Pro Ser Thr Pro Phe Ser Gly Leu Ser Leu Leu Ala Phe
            195                 200                 205
Glu Thr Val Tyr Arg Leu Asn Met Gly Gly Pro Leu Leu Thr Ser Gln
    210                 215                 220
Asn Asp Thr Leu Gly Arg Gln Trp Asp Asn Asp Ala Glu Tyr Leu His
225                 230                 235                 240
Val Asn Ser Ser Val Leu Val Thr Ala Asn Pro Ser Ser Ile Lys
                245                 250                 255
Tyr Ser Pro Ser Val Thr Gln Glu Thr Ala Pro Asn Met Val Tyr Ala
            260                 265                 270
Thr Ala Asp Thr Met Gly Asp Ala Asn Val Ala Ser Pro Ser Phe Asn
            275                 280                 285
Val Thr Trp Val Leu Pro Val Asp Pro Asp Phe Arg Tyr Phe Val Arg
    290                 295                 300
Val His Phe Cys Asp Ile Val Ser Gln Ala Leu Asn Thr Leu Val Phe
305                 310                 315                 320
Asn Leu Tyr Val Asn Asp Asp Leu Ala Leu Gly Ser Leu Asp Leu Ser
                325                 330                 335
Thr Leu Thr Asn Gly Leu Lys Val Pro Tyr Phe Lys Asp Phe Ile Ser
            340                 345                 350
Asn Gly Ser Val Glu Ser Ser Gly Val Leu Thr Val Ser Val Gly Pro
            355                 360                 365
Asp Ser Gln Ala Asp Ile Thr Asn Ala Thr Met Asn Gly Leu Glu Val
    370                 375                 380
Leu Lys Ile Ser Asn Glu Ala Lys Ser Leu Ser Gly Val Ser Ser Val
385                 390                 395                 400
Lys Ser Leu Leu Pro Gly Gly Ser Gly Ser Lys Ser Lys Lys Lys Ala
                405                 410                 415
Val Ile Ile Gly Ser Leu Val Gly Ala Val Thr Leu Ile Leu Leu Ile
            420                 425                 430
Ala Val Cys Cys Tyr Cys Cys Leu Val Ala Ser Arg Lys Gln Arg Ser
            435                 440                 445
Thr Ser Pro Gln Glu Gly Gly Asn Gly His Pro Trp Leu Pro Leu Pro
    450                 455                 460
Leu Tyr Gly Leu Ser Gln Thr Leu Thr Lys Ser Thr Ala Ser His Lys
465                 470                 475                 480
Ser Ala Thr Ala Ser Cys Ile Ser Leu Ala Ser Thr His Leu Gly Arg
                485                 490                 495

```
Cys Phe Met Phe Gln Glu Ile Met Asp Ala Thr Asn Lys Phe Asp Glu
                500                 505                 510

Ser Ser Leu Leu Gly Val Gly Phe Gly Arg Val Tyr Lys Gly Thr
        515                 520                 525

Leu Glu Asp Gly Thr Lys Val Ala Val Lys Arg Gly Asn Pro Arg Ser
        530                 535                 540

Glu Gln Gly Met Ala Glu Phe Arg Thr Glu Ile Glu Met Leu Ser Lys
545                 550                 555                 560

Leu Arg His Arg His Leu Val Ser Leu Ile Gly Tyr Cys Asp Glu Arg
                565                 570                 575

Ser Glu Met Ile Leu Val Tyr Glu Tyr Met Ala Asn Gly Pro Leu Arg
                580                 585                 590

Ser His Leu Tyr Gly Ala Asp Leu Pro Pro Leu Ser Trp Lys Gln Arg
        595                 600                 605

Leu Glu Ile Cys Ile Gly Ala Ala Arg Gly Leu His Tyr Leu His Thr
        610                 615                 620

Gly Ala Ser Gln Ser Ile Ile His Arg Asp Val Lys Thr Thr Asn Ile
625                 630                 635                 640

Leu Leu Asp Glu Asn Leu Val Ala Lys Val Ala Asp Phe Gly Leu Ser
                645                 650                 655

Lys Thr Gly Pro Ser Leu Asp Gln Thr His Val Ser Thr Ala Val Lys
        660                 665                 670

Gly Ser Phe Gly Tyr Leu Asp Pro Glu Tyr Phe Arg Gln Gln Leu
        675                 680                 685

Thr Glu Lys Ser Asp Val Tyr Ser Phe Gly Val Val Leu Met Glu Val
690                 695                 700

Leu Cys Cys Arg Pro Ala Leu Asn Pro Val Leu Pro Arg Glu Gln Val
705                 710                 715                 720

Asn Ile Ala Glu Trp Ala Met Ala Trp Gln Lys Gly Leu Leu Asp
                725                 730                 735

Gln Ile Met Asp Ser Asn Leu Thr Gly Lys Val Asn Pro Ala Ser Leu
                740                 745                 750

Lys Lys Phe Gly Glu Thr Ala Glu Lys Cys Leu Ala Glu Tyr Gly Val
        755                 760                 765

Asp Arg Pro Ser Met Gly Asp Val Leu Trp Asn Leu Glu Tyr Ala Leu
770                 775                 780

Gln Leu Glu Glu Thr Ser Ser Ala Leu Met Glu Pro Asp Asp Asn Ser
785                 790                 795                 800

Thr Asn His Ile Pro Gly Ile Pro Met Ala Pro Met Glu Pro Phe Asp
                805                 810                 815

Asn Ser Met Ser Ile Ile Asp Arg Gly Gly Val Asn Ser Gly Thr Gly
                820                 825                 830

Thr Asp Asp Asp Ala Glu Asp Ala Thr Thr Ser Ala Val Phe Ser Gln
                835                 840                 845

Leu Val His Pro Arg Gly Arg
        850                 855

<210> SEQ ID NO 5
<211> LENGTH: 2779
<212> TYPE: DNA
<213> ORGANISM: Arabidopsis thaliana

<400> SEQUENCE: 5
atgggtattg aaaagtttga aactttcatc ttgatttcaa cgatttcgat cttgctttgt     60
```

-continued

```
atctgccatg gattcacacc tgtggataat tacttgatca actgtggatc accaaccaat    120
ggaacactaa tgggtcgaat ctttctgtct gataagctct cttcgaagtt acttacttcg    180
tccaaagaga ttctcgcaag cgtaggcggt aactctggct cagacattta ccacacggca    240
agagtcttca ccgaagtctc tagctacaaa ttctcggtca ctcgtggtcg tcattgggtt    300
cgtctctatt tcaatccttt tgactaccaa aacttcaaaa tgggttcagc taaattcgcg    360
gtttcttcac aaagtcatgt ccttttgagt gatttcactg ttacgagttc aaaagttgtc    420
aaagagtact ctttgaacgt gactactaat gatttagtgc tcacctttac tccctctagt    480
ggttcgtttg cgtttgtgaa tgctatcgag gttatatcga ttccagatac tttgattact    540
ggtagtccaa ggtttgtagg caaccctgcg cagtttccgg atatgtcaat gcaaggtctt    600
gaaaccattc atagagtcaa catgggtggt ccgcttgttg cgtctaacaa cgatacgtta    660
acgagaactt gggtgcctga ctcggagttt ctgcttgaga agaatttagc taagagtatg    720
tctaagtttt caactgttaa ctttgttcca ggttatgcaa cagaggactc tgctccaaga    780
actgtctatg gtagttgtac tgagatgaat tccgctgata cccgaatag catttcaat    840 gtgacttggg agttcgatgt tgacccgggt tttcagtact atttccgctt tcatttctgc    900
gatatcgtta gcttgtcgtt aaaccagcta tatttcaatc tttatgttga ctcaatggtt    960
gctgctacgg atattgatct tagcactctt gtggataaca ctttggctgg tgcatattcg   1020
atggactttg tcacgcagac gccaaagggt agtaataaag tccgtgtgag catcggtccg   1080
tcgactgttc acaccgatta tccaaacgcg attgtgaatg gattggagat tatgaagatg   1140
aataactcta agggtcagtt aagcactggg acatttgtgc ctggtagtag ttcaagcagt   1200
aagagtaatc tcgggttgat tgtaggttca gccattggtt cgttgctcgc ggtagtcttc   1260
ttgggaagtt gctttgtgtt gtataagaag cggaacgtg ccaagacgg tcattcaaag   1320 acttggatgc cgttttcgat aaatggaact tcgatgggaa gcaaatactc caatggaact   1380
acgcttacaa gtataactac caatgccaat taccgtattc cctttgcagc ggttaaagac   1440
gctacaaata actttgacga gagccgcaac atcggtgtag gcggttttgg taaagtctac   1500
aaaggagagc ttaatgacgg tacaaaggta gctgtgaaaa gagggaaccc aaaatctcag   1560
caagggcttg cggaattcag gacagaaatc gagatgttat ctcagtttcg tcaccgccat   1620
ttggtttctc tgatcggtta ttgtgacgag aacaatgaga tgatactaat ttacgagtat   1680
atggagaatg gaacggtaaa gagtcatctt tatggctcag gtctacctag cttgacttgg   1740
aaacaacggc ttgagatctg cattggtgca gctagaggct tgcattacct tcacacgggt   1800
gactcgaaac cggtcattca cagagacgtg aaatctgcaa acatattgct tgacgagaac   1860
ttcatggcta agttgcaga cttttggactg tccaagactg gacccgagct tgatcagact   1920
catgtaagta ctgctgtcaa aggaagtttt ggttatcttg accccgagta cttcagaagg   1980
caacagctca cagataaatc cgatgtttat tccttcggag ttgttctctt cgaggtttta   2040
tgtgctagac ctgttataga cccaacactt ccaagagaga tggtgaatct tgcagaatgg   2100
gctatgaaat ggcagaagaa agggcaactg gatcagatca tcgaccagtc gcttcgcgga   2160
aatatcagac ccgattcgtt aaggaaattt gcggaaacag gtgagaaatg tttagcggat   2220
tatggagttg ataggccatc tatgggagat gtgttgtgga atcttgaata cgctctgcag   2280
cttcaagaag cagtcattga tggtgaacca gaagataata gcacgaatat gattggtgaa   2340
ttacctccgc agatcaataa tttcagtcag ggagacacta gtgttaacgt tccgggcaca   2400
gcggggcgat tcgaggaatc tagtattgat gatctctctg gcgtttccat gagtaaagta   2460
```

```
ttctcacaac tggtgaaatc tgaaggaaga tagtgaaaga tttgagcaat gcagtgccaa    2520
gaaaagccaa agatctgatc tttttgatag aaacagagca agcaaagtat gtaaccagga    2580
aaaaagcatc aggttatttt cagataggat ctttgtcttt gcttgatctg tttctactgc    2640 agattttca tcagtgatta aacggttact ttgaaaattt accttatttt gttcctctct     2700
cccttatcct gagtttgtat tttattgatg ttcattttga aattgtctga aatttgtttg    2760 ttcttttac tatatggat                                                   2779
```

<210> SEQ ID NO 6
<211> LENGTH: 830
<212> TYPE: PRT
<213> ORGANISM: Arabidopsis thaliana

<400> SEQUENCE: 6

```
Met Gly Ile Glu Lys Phe Glu Thr Phe Ile Leu Ile Ser Thr Ile Ser
1               5                   10                  15

Ile Leu Leu Cys Ile Cys His Gly Phe Thr Pro Val Asp Asn Tyr Leu
            20                  25                  30

Ile Asn Cys Gly Ser Pro Thr Asn Gly Thr Leu Met Gly Arg Ile Phe
        35                  40                  45

Leu Ser Asp Lys Leu Ser Ser Lys Leu Leu Thr Ser Ser Lys Glu Ile
    50                  55                  60

Leu Ala Ser Val Gly Gly Asn Ser Gly Ser Asp Ile Tyr His Thr Ala
65                  70                  75                  80

Arg Val Phe Thr Glu Val Ser Ser Tyr Lys Phe Ser Val Thr Arg Gly
                85                  90                  95

Arg His Trp Val Arg Leu Tyr Phe Asn Pro Phe Asp Tyr Gln Asn Phe
            100                 105                 110

Lys Met Gly Ser Ala Lys Phe Ala Val Ser Ser Gln Ser His Val Leu
        115                 120                 125

Leu Ser Asp Phe Thr Val Thr Ser Ser Lys Val Val Lys Glu Tyr Ser
    130                 135                 140

Leu Asn Val Thr Thr Asn Asp Leu Val Leu Thr Phe Thr Pro Ser Ser
145                 150                 155                 160

Gly Ser Phe Ala Phe Val Asn Ala Ile Glu Val Ile Ser Ile Pro Asp
                165                 170                 175

Thr Leu Ile Thr Gly Ser Pro Arg Phe Val Gly Asn Pro Ala Gln Phe
            180                 185                 190

Pro Asp Met Ser Met Gln Gly Leu Glu Thr Ile His Arg Val Asn Met
        195                 200                 205

Gly Gly Pro Leu Val Ala Ser Asn Asn Asp Thr Leu Thr Arg Thr Trp
    210                 215                 220

Val Pro Asp Ser Glu Phe Leu Leu Glu Lys Asn Leu Ala Lys Ser Met
225                 230                 235                 240

Ser Lys Phe Ser Thr Val Asn Phe Val Pro Gly Tyr Ala Thr Glu Asp
                245                 250                 255

Ser Ala Pro Arg Thr Val Tyr Gly Ser Cys Thr Glu Met Asn Ser Ala
            260                 265                 270

Asp Asn Pro Asn Ser Ile Phe Asn Val Thr Trp Glu Phe Asp Val Asp
        275                 280                 285

Pro Gly Phe Gln Tyr Tyr Phe Arg Phe His Phe Cys Asp Ile Val Ser
    290                 295                 300

Leu Ser Leu Asn Gln Leu Tyr Phe Asn Leu Tyr Val Asp Ser Met Val
```

```
             305                 310                 315                 320
Ala Ala Thr Asp Ile Asp Leu Ser Thr Leu Val Asp Asn Thr Leu Ala
                 325                 330                 335
Gly Ala Tyr Ser Met Asp Phe Val Thr Gln Thr Pro Lys Gly Ser Asn
                 340                 345                 350
Lys Val Arg Val Ser Ile Gly Pro Ser Thr Val His Thr Asp Tyr Pro
                 355                 360                 365
Asn Ala Ile Val Asn Gly Leu Glu Ile Met Lys Met Asn Asn Ser Lys
                 370                 375                 380
Gly Gln Leu Ser Thr Gly Thr Phe Val Pro Gly Ser Ser Ser Ser Ser
385                  390                 395                 400
Lys Ser Asn Leu Gly Leu Ile Val Gly Ser Ala Ile Gly Ser Leu Leu
                 405                 410                 415
Ala Val Val Phe Leu Gly Ser Cys Phe Val Leu Tyr Lys Lys Arg Lys
                 420                 425                 430
Arg Gly Gln Asp Gly His Ser Lys Thr Trp Met Pro Phe Ser Ile Asn
                 435                 440                 445
Gly Thr Ser Met Gly Ser Lys Tyr Ser Asn Gly Thr Thr Leu Thr Ser
                 450                 455                 460
Ile Thr Thr Asn Ala Asn Tyr Arg Ile Pro Phe Ala Ala Val Lys Asp
465                  470                 475                 480
Ala Thr Asn Asn Phe Asp Glu Ser Arg Asn Ile Gly Val Gly Gly Phe
                 485                 490                 495
Gly Lys Val Tyr Lys Gly Glu Leu Asn Asp Gly Thr Lys Val Ala Val
                 500                 505                 510
Lys Arg Gly Asn Pro Lys Ser Gln Gln Gly Leu Ala Glu Phe Arg Thr
                 515                 520                 525
Glu Ile Glu Met Leu Ser Gln Phe Arg His Arg His Leu Val Ser Leu
                 530                 535                 540
Ile Gly Tyr Cys Asp Glu Asn Asn Glu Met Ile Leu Ile Tyr Glu Tyr
545                  550                 555                 560
Met Glu Asn Gly Thr Val Lys Ser His Leu Tyr Gly Ser Gly Leu Pro
                 565                 570                 575
Ser Leu Thr Trp Lys Gln Arg Leu Glu Ile Cys Ile Gly Ala Ala Arg
                 580                 585                 590
Gly Leu His Tyr Leu His Thr Gly Asp Ser Lys Pro Val Ile His Arg
                 595                 600                 605
Asp Val Lys Ser Ala Asn Ile Leu Leu Asp Glu Asn Phe Met Ala Lys
                 610                 615                 620
Val Ala Asp Phe Gly Leu Ser Lys Thr Gly Pro Glu Leu Asp Gln Thr
625                  630                 635                 640
His Val Ser Thr Ala Val Lys Gly Ser Phe Gly Tyr Leu Asp Pro Glu
                 645                 650                 655
Tyr Phe Arg Arg Gln Gln Leu Thr Asp Lys Ser Asp Val Tyr Ser Phe
                 660                 665                 670
Gly Val Val Leu Phe Glu Val Leu Cys Ala Arg Pro Val Ile Asp Pro
                 675                 680                 685
Thr Leu Pro Arg Glu Met Val Asn Leu Ala Glu Trp Ala Met Lys Trp
                 690                 695                 700
Gln Lys Lys Gly Gln Leu Asp Gln Ile Ile Asp Gln Ser Leu Arg Gly
705                  710                 715                 720
Asn Ile Arg Pro Asp Ser Leu Arg Lys Phe Ala Glu Thr Gly Glu Lys
                 725                 730                 735
```

```
Cys Leu Ala Asp Tyr Gly Val Asp Arg Pro Ser Met Gly Asp Val Leu
            740                 745                 750
Trp Asn Leu Glu Tyr Ala Leu Gln Leu Gln Glu Ala Val Ile Asp Gly
        755                 760                 765
Glu Pro Glu Asp Asn Ser Thr Asn Met Ile Gly Glu Leu Pro Pro Gln
    770                 775                 780
Ile Asn Asn Phe Ser Gln Gly Asp Thr Ser Val Asn Val Pro Gly Thr
785                 790                 795                 800
Ala Gly Arg Phe Glu Glu Ser Ser Ile Asp Asp Leu Ser Gly Val Ser
                805                 810                 815
Met Ser Lys Val Phe Ser Gln Leu Val Lys Ser Glu Gly Arg
            820                 825                 830

<210> SEQ ID NO 7
<211> LENGTH: 2550
<212> TYPE: DNA
<213> ORGANISM: Arabidopsis thaliana

<400> SEQUENCE: 7
```

| | | | | |
|---|---|---|---|---|
| atgtcgaagc tgaggaaaaa gtatctggaa catcttctat gtgtgttgat tttctttact | 60 |
| tatgttattg ctatggagag agctcagtcc aagagcttcc ttgtagattg tggctcaaat | 120 |
| gctacaaccg aagtagatgg aagaacatgg gttggtgatt tatctcccaa caagagtgtg | 180 |
| accctgcaag gatttgatgc cattactgct tcgacatcga aaggaagttc tgtttacgct | 240 |
| gagatatata agactgctcg tgttttcgac gctgtgttga actatacatt gaaggtata | 300 |
| actcaaggga attactttgt taggctccat ttcagcccct tcgctattga aaaccacaat | 360 |
| gtgaatgagt cttctttcag cgtctttgcg gatggtctga gactgatgct tgacatcaac | 420 |
| atcgcgggag aaatcgcgca taagaatctc atcttggaaa gcactggtca aatgctact | 480 |
| gcctcttctt tggttaaaga gtttctgtta cctactggac caggaaaact ggttttaagt | 540 |
| ttcatcccgg agaaagggtc tttcgggttt gtcaatgcta ttgagatagt ctctgttgat | 600 |
| gataagcttt ttaaggaatc agttactaaa gttggtggaa gtgaagtgga gcttggtttg | 660 |
| ggtggacgag ggattgaaac tatgtataggg ctaaacgttg gtggtcccaa gctaggtcca | 720 |
| agcaaagatc ttaagcttta tagaacatgg gaaacagatt taagctacat ggtgattgag | 780 |
| aacgctggtg tagaagtcaa gaacagctca aatatcacat atgctttggc tgatgattct | 840 |
| cctgtggctc ctcttcttgt ttatgaaact gctaggatga tgtcaaacac tgaagtcttg | 900 |
| gagaaacggt tcaacatttc ttggaagttt gaagttgatc ctaattttcga ctacttggtt | 960 |
| aggcttcatt tctgtgagct tcttgttgat aagcaaaacc agaggatttt caggatatac | 1020 |
| ataaacaacc agacggctgc tggtaatttc gatatatttg ctcacgcggg cgggaagaac | 1080 |
| aaaggtatat atcaagatta cttggatccg gtctcctcta agaacgacgt tctctggatt | 1140 |
| caacttggac ctgactcatc tgttggtgct tctggagacg ctcttctgag tggtcttgag | 1200 |
| attttcaagc tcagcaaaaa tgggaatctt gctcatctca tcaggtttga ttcgactggt | 1260 |
| cactcggtaa gtgactcgaa gatgcggatt atttggatca gtgttggtgc tggtatagca | 1320 |
| attatcattt ttttcgtgtt cttgggaatc ttggtagtat gttatgcaa gaaaaggcga | 1380 |
| agcaaatcag atgagtcgaa aaacaatcct cccgggtggc gtccgttgtt tttgcatgtc | 1440 |
| aataacagta ctgcaaacgc caaagcaacg ggaggctcgc tgagactgaa cactcttgca | 1500 |
| gcatctacaa tgggaaggaa gtttacacta gccgagattc gtgcagcaac taagaacttt | 1560 |

-continued

```
gatgatggtt tagctattgg agttggaggg tttggtaagg tttacagagg agagcttgaa    1620
gatggaacac tcatagctat aaaacgagcc accccacatt ctcagcaagg gcttgctgaa    1680
ttcgaaaccg agatcgtgat gctctcaaga cttaggcata ggcatcttgt gtctttgatc    1740
gggttctgcg atgagcacaa tgagatgatc ttggtttatg aatacatggc aaatggaact    1800
ctcaggagtc atctctttgg aagcaacctt ccgccattat catggaagca acggcttgaa    1860
gcttgtatag gctctgcgag aggattgcat taccttcaca cagggtcaga gagaggaatc    1920
attcacagag atgtcaaaac aacaaacata ctattagacg agaactttgt ggcaaagatg    1980
tctgattttg ggctgtcgaa agctggaccg tccatggacc atactcatgt gagtacagct    2040
gtgaaaggaa gttttggtta tcttgatcct gaatacttta gaaggcaaca gttaacagag    2100
aagtcagatg tttactcttt tggtgttgtg ttgttcgaag ctgtttgtgc tcgagctgtt    2160
ataaacccaa ctttgcctaa agaccagatc aaccttgcgg aatgggcttt aagctggcaa    2220
aaacagagaa acctcgagtc catcatcgac tcaaatctga ggggaaacta cagtcctgaa    2280
tcgttggaga gtatgggga gatagcagag aagtgcttag cggatgaagg gaagaacagg    2340
ccaatgatgg gagaagtgtt atggagcttg gagtatgttt tgcagattca tgaagcttgg    2400
cttcgcaaac agaatggaga aaactcgttt tcgagcagcc aagcggtaga agaagcacca    2460
gagagcttta ctcttccagc ttgttccaat caagattcct cagaaactga gcagagccaa    2520
acaggatctg ctcttcacaa ttcggcttag                                    2550
```

<210> SEQ ID NO 8
<211> LENGTH: 849
<212> TYPE: PRT
<213> ORGANISM: Arabidopsis thaliana

<400> SEQUENCE: 8

```
Met Ser Lys Leu Arg Lys Lys Tyr Leu Glu His Leu Leu Cys Val Leu
1               5                   10                  15

Ile Phe Phe Thr Tyr Val Ile Gly Tyr Gly Glu Ala Gln Ser Lys Ser
            20                  25                  30

Phe Leu Val Asp Cys Gly Ser Asn Ala Thr Thr Glu Val Asp Gly Arg
        35                  40                  45

Thr Trp Val Gly Asp Leu Ser Pro Asn Lys Ser Val Thr Leu Gln Gly
    50                  55                  60

Phe Asp Ala Ile Thr Ala Ser Thr Ser Lys Gly Ser Ser Val Tyr Ala
65                  70                  75                  80

Glu Ile Tyr Lys Thr Ala Arg Val Phe Asp Ala Val Leu Asn Tyr Thr
                85                  90                  95

Phe Glu Gly Ile Thr Gln Gly Asn Tyr Phe Val Arg Leu His Phe Ser
            100                 105                 110

Pro Phe Ala Ile Glu Asn His Asn Val Asn Glu Ser Ser Phe Ser Val
        115                 120                 125

Phe Ala Asp Gly Leu Arg Leu Met Leu Asp Ile Asn Ile Ala Gly Glu
    130                 135                 140

Ile Ala His Lys Asn Leu Ile Leu Glu Ser Thr Gly His Asn Ala Thr
145                 150                 155                 160

Ala Ser Ser Leu Val Lys Glu Phe Leu Pro Thr Gly Pro Gly Lys
                165                 170                 175

Leu Val Leu Ser Phe Ile Pro Glu Lys Gly Ser Phe Gly Phe Val Asn
            180                 185                 190

Ala Ile Glu Ile Val Ser Val Asp Asp Lys Leu Phe Lys Glu Ser Val
```

```
            195                 200                 205
Thr Lys Val Gly Gly Ser Glu Val Glu Leu Gly Leu Gly Gly Arg Gly
210                 215                 220

Ile Glu Thr Met Tyr Arg Leu Asn Val Gly Gly Pro Lys Leu Gly Pro
225                 230                 235                 240

Ser Lys Asp Leu Lys Leu Tyr Arg Thr Trp Glu Thr Asp Leu Ser Tyr
                245                 250                 255

Met Val Ile Glu Asn Ala Gly Val Glu Val Lys Asn Ser Ser Asn Ile
            260                 265                 270

Thr Tyr Ala Leu Ala Asp Asp Ser Pro Val Ala Pro Leu Leu Val Tyr
        275                 280                 285

Glu Thr Ala Arg Met Met Ser Asn Thr Glu Val Leu Glu Lys Arg Phe
290                 295                 300

Asn Ile Ser Trp Lys Phe Glu Val Asp Pro Asn Phe Asp Tyr Leu Val
305                 310                 315                 320

Arg Leu His Phe Cys Glu Leu Leu Val Asp Lys Gln Asn Gln Arg Ile
                325                 330                 335

Phe Arg Ile Tyr Ile Asn Asn Gln Thr Ala Ala Gly Asn Phe Asp Ile
            340                 345                 350

Phe Ala His Ala Gly Gly Lys Asn Lys Gly Ile Tyr Gln Asp Tyr Leu
        355                 360                 365

Asp Pro Val Ser Ser Lys Asn Asp Val Leu Trp Ile Gln Leu Gly Pro
370                 375                 380

Asp Ser Ser Val Gly Ala Ser Asp Ala Leu Leu Ser Gly Leu Glu
385                 390                 395                 400

Ile Phe Lys Leu Ser Lys Asn Gly Asn Leu Ala His Leu Ile Arg Phe
                405                 410                 415

Asp Ser Thr Gly His Ser Val Ser Asp Ser Lys Met Arg Ile Ile Trp
            420                 425                 430

Ile Ser Val Gly Ala Gly Ile Ala Ile Ile Phe Phe Val Phe Leu
        435                 440                 445

Gly Ile Leu Val Val Cys Leu Cys Lys Lys Arg Arg Ser Lys Ser Asp
450                 455                 460

Glu Ser Lys Asn Asn Pro Pro Gly Trp Arg Pro Leu Phe Leu His Val
465                 470                 475                 480

Asn Asn Ser Thr Ala Asn Ala Lys Ala Thr Gly Gly Ser Leu Arg Leu
                485                 490                 495

Asn Thr Leu Ala Ala Ser Thr Met Gly Arg Lys Phe Thr Leu Ala Glu
            500                 505                 510

Ile Arg Ala Ala Thr Lys Asn Phe Asp Asp Gly Leu Ala Ile Gly Val
        515                 520                 525

Gly Gly Phe Gly Lys Val Tyr Arg Gly Glu Leu Glu Asp Gly Thr Leu
530                 535                 540

Ile Ala Ile Lys Arg Ala Thr Pro His Ser Gln Gln Gly Leu Ala Glu
545                 550                 555                 560

Phe Glu Thr Glu Ile Val Met Leu Ser Arg Leu Arg His Arg His Leu
                565                 570                 575

Val Ser Leu Ile Gly Phe Cys Asp Glu His Asn Glu Met Ile Leu Val
            580                 585                 590

Tyr Glu Tyr Met Ala Asn Gly Thr Leu Arg Ser His Leu Phe Gly Ser
        595                 600                 605

Asn Leu Pro Pro Leu Ser Trp Lys Gln Arg Leu Glu Ala Cys Ile Gly
610                 615                 620
```

```
Ser Ala Arg Gly Leu His Tyr Leu His Thr Gly Ser Glu Arg Gly Ile
625                 630                 635                 640

Ile His Arg Asp Val Lys Thr Thr Asn Ile Leu Leu Asp Glu Asn Phe
                645                 650                 655

Val Ala Lys Met Ser Asp Phe Gly Leu Ser Lys Ala Gly Pro Ser Met
            660                 665                 670

Asp His Thr His Val Ser Thr Ala Val Lys Gly Ser Phe Gly Tyr Leu
        675                 680                 685

Asp Pro Glu Tyr Phe Arg Arg Gln Gln Leu Thr Glu Lys Ser Asp Val
    690                 695                 700

Tyr Ser Phe Gly Val Val Leu Phe Glu Ala Val Cys Ala Arg Ala Val
705                 710                 715                 720

Ile Asn Pro Thr Leu Pro Lys Asp Gln Ile Asn Leu Ala Glu Trp Ala
            725                 730                 735

Leu Ser Trp Gln Lys Gln Arg Asn Leu Glu Ser Ile Ile Asp Ser Asn
            740                 745                 750

Leu Arg Gly Asn Tyr Ser Pro Glu Ser Leu Glu Lys Tyr Gly Glu Ile
        755                 760                 765

Ala Glu Lys Cys Leu Ala Asp Glu Gly Lys Asn Arg Pro Met Met Gly
770                 775                 780

Glu Val Leu Trp Ser Leu Glu Tyr Val Leu Gln Ile His Glu Ala Trp
785                 790                 795                 800

Leu Arg Lys Gln Asn Gly Glu Asn Ser Phe Ser Ser Ser Gln Ala Val
                805                 810                 815

Glu Glu Ala Pro Glu Ser Phe Thr Leu Pro Ala Cys Ser Asn Gln Asp
            820                 825                 830

Ser Ser Glu Thr Glu Gln Ser Gln Thr Gly Ser Ala Leu His Asn Ser
        835                 840                 845

Ala
```

MODULATION OF RECEPTOR-LIKE KINASES FOR PROMOTION OF PLANT GROWTH

CROSS-REFERENCE TO RELATED APPLICATIONS

This is a Continuation Application of U.S. Ser. No. 12/928,233 filed Dec. 7, 2010 (now abandoned), which application claims priority under 35 U.S.C. §119 to provisional application Ser. No. 61/283,674 filed Dec. 7, 2009, herein incorporated by reference in their entirety.

GRANT REFERENCE

This invention was made with Government Support from the National Science Foundation, NSF Grant No, IOS0546503. The government has certain rights in the invention.

FIELD OF THE INVENTION

The invention relates generally to the field of molecular biology.

BACKGROUND OF THE INVENTION

Plant growth and development are controlled by intrinsic growth regulators or hormones and environmental cues through interconnected signal transduction pathways. A single hormone can regulate many different processes and likewise different hormones can cooperate to control the same cellular process. Plant steroid hormones, brassinosteroids (BRs), regulate many growth and developmental processes such as cell elongation, senescence, vascular development, reproduction, and various stress responses. BRs signal through a membrane-localized, leucine-rich repeat (LRR) receptor kinase BRI1 and co-receptor BAK1 to regulate several intermediate signaling components. BR signaling eventually controls BES1 and BZR1 family transcription factors, which mediate the expression of many genes for various BR responses. Consistent with the main function of BRs in cell elongation, BRs promote the expression of a number of cell wall remodeling enzymes required for cell elongation. In addition, BRs also regulate a variety of other genes implicated in signal transduction including several receptor-like kinases (RLKs), which are postulated to be involved in communicating BR signals to other pathways.

Receptor like kinases (RLKs) are involved in transmission of extracellular signals into the cell. The RLK proteins have a modular structure, starting from the N-terminus with a secretion signal that gets processed, an extracellular domain, a single transmembrane domain and a cytoplasmic kinase domain. Receptor like kinases are postulated to form homodimers or heterodimers of two related kinases, similar as for animal receptor kinases (Torii, Curr. Opin. Plant Biol. 3, 361-367, 2000). Animal receptor-like kinases mostly have tyrosine kinase activity, whereas plant RLKs all have Ser/Thr kinase specificity, or may sometimes have a dual specificity. In animals, most of the RLKs act as growth factor receptors, whereas plant receptor like kinases may function in various processes, including development, hormone perception or pathogen responses. An overview of developmental functions of plant receptor like kinases such as meristem development, pollen-pistil interactions, hormone signaling, gametophyte development, cell morphogenesis and differentiation, organ shape, organ abscission and somatic embryogenesis is given by Becraft (Annu Rev. Cell Dev. Biol., 18, 163-192, 2002).

Receptor-like kinases may be grouped according to the structure of their extracellular domain (Shiu and Bleecker, Proc. Natl. Acad. Sci. USA 98, 10763-10768, 2001). The largest group was that of the Leucine Rich Repeat (LRR) containing RLKs; which may be split up in 13 subgroups (LRR I to LRR XIII) based on the organization of the LRR domains in the extracellular part of the RLK. The LRR units may be present in varying numbers and may be arranged in continuous or interrupted repeats.

WO 2004/007712 describes and characterizes a number of *Arabidopsis* RKS genes that encode LRR receptor-like kinases. It was postulated that modification of expression of the RKS genes would cause a modification of the brassinosteroid-signaling pathway. The data show that, depending on the specific RKS gene and the kind of expression (up- or downregulation of expression compared to wild type), results in various phenotypes. For example, RKS4 and RKS10 are reported to stimulate cell division. Overexpression of the RKS4 gene resulted in increased cell division and an altered plant phenotype, whereas modulation of RKS10 did change the cell number, but not plant or organ size. Overexpression of RKS10 also caused the formation of many generative meristems that did not end up in normally developed flowers. Both overexpression and down-regulated expression of RKS10 had a strong negative effect on pollen formation. Root length was negatively affected by overexpressing RKS10, while initiation and outgrowth of lateral roots was promoted. The same effects on root growth may be obtained by suppressing RKS1 expression. Also overexpression of the RKS3, RKS4 or RKS6 genes had positive effects on root length. Increased apical shoot meristem formation and outgrowth was obtained by overexpressing RKS0 but also by downregulating expression of RKS3, RKS4, RKS8 or RKS10. RKS4 overexpression was reported to result in larger seed size, but did not result in higher seed yield; no functional analysis was made of the RKS11 gene.

Accordingly, the ability to regulate the brassinosteroid induced pathways, and concomitant receptor like kinases, to influence many different agricultural traits of interest, is of considerable value to commercial agriculture. The present invention provides new mechanisms for plant growth, which are influenced somewhat by the brassinosteroid pathway, but also represent a separate and independent pathway involving several receptor like kinases that influences plant growth, cellular elongation and other yield related traits. These and other features will become apparent from the description of the invention which follows.

SUMMARY OF THE INVENTION

Applicants have identified a new pathway for plant growth, plane defense and cellular elongation, in plants that functions cooperatively with, but largely independent of the brassinosteroid pathway. As such methods are disclosed herein for improving plant growth, or plant host defense by modulating the activity of or the genes encoding one or more components of this pathway, which includes members of the family of CrRLK1L family of receptor like kinases. Methods are also disclosed for identifying other signaling components in this pathway.

According to the invention, applicants have found that the CrRLK1L receptor like kinases HERK1 (At3g46290) and HERK2 (At1g30570), THE1, and FER all function in a novel pathway of plant growth and their activity may be modulated in a plant to improve growth, cellular elongation, and other yield related traits when compared to a non modulated plant. Other family members such as At2g39360, At2g23200 and At5g24010, as well as analogues and homologs from other plant species will be expected to have similar affects.

HERK1:
Rice: Os03g17300 (http://www.ncbi.nlm.nih.gov/protein/108707517)
Soybean: FJ014780 (http://www.ncbi.nlm.nih.gov/nuccore/223452411)
Maize: BT067506 (http://www.ncbi.nlm.nih.gov/nuccore/224030654)

HERK2:
Rice: Os07g05370 (http://www.ncbi.nlm.nih.gov/nuccore/32990914)
Soybean: FJ014717 (http://www.ncbi.nlm.nih.gov/nuccore/223452308)
Maize: BT060758 (http://www.ncbi.nlm.nih.gov/nuccore/223942742)

THE1:
Rice: Os03g55210 (http://www.ncbi.nlm.nih.gov/protein/108711198)
Soybean: FJ014773 (http://www.ncbi.nlm.nih.gov/nuccore/223452397)
Maize: DQ403195 (http://www.ncbi.nlm.nih.gov/nuccore/89329659)

FER: Rice: Os01g56330 (http://www.ncbi.nlm.nih.gov/nuccore/32986984)
Soybean: FJ014770 (http://www.ncbi.nlm.nih.gov/nuccore/223452392)
Maize: BT033507 (http://www.ncbi.nlm.nih.gov/nuccore/194688855)

Thus, the invention in one aspect provides a method for enhancing yield-related traits such as plant growth and cellular elongation in plants relative to control plants, comprising modulating the activity or expression in a plant of a nucleic acid encoding a HERK1, HERK2, THE1, or FER protein, or a part thereof. Applicants here report for the first time the involvement of HERK1 and HERK2 in promoting cellular elongation in plants and as such their activity or expression may be modulated to affect the same.

THE1 and FER had previously been identified as having cellular elongation inhibiting affects in response to cell damage, and in pollen tube elongation leading to eruption of the pollen tip and release of sperm. Quite surprisingly, applicants have found that these proteins have the opposite affect for a non-wounded plant in vegetative growth and that they may be up regulated to increase plant growth and cellular elongation. In fact, all four proteins HERK1, HERK2, FER and THE1 were found to work together to improve growth, as deleterious mutants of all four resulted in dwarf plants. Such plants may also be used to identify other signaling molecules from this pathway. Thus the invention also includes modulating the activity of FER and THE1 in healthy plant vegetative growth situations and in a preferred embodiment modulation of all three together to optimize plant growth, cellular elongation and other plant yield characteristics.

The present invention therefore provides methods for enhancing yield-related traits in plants relative to control plants, comprising preferentially modulating the activity of a CrRLK1L receptor like kinases HERK1, HERK2, THE1 or FER or a combination thereof or modulating the expression in a plant or plant parts of a nucleic acid encoding one or more CrRLK1L receptor like kinases HERK1, HERK2, THE1 or FER or a combination thereof.

To the extent that this pathway is influenced by brassinosteroids, applicants have further found that the transcription factor BEST (BRI1-EMS-SUPPRESSOR 1); a regulator of the brassinosteroid pathway up regulates HERK1, HERK2, THE1, and FER. The invention in another aspect provides a method for enhancing yield-related traits such as plant growth and cellular elongation in plants relative to control plants, comprising modulating the activity of a BES1 protein or modulating the expression in a plant of a nucleic acid encoding a BES1 transcription factor protein, or a part thereof.

In other embodiments, different steps along this novel plant growth or signaling pathway could be modulated. For example, BES1 or other brassinosteroid components found to affect this pathway could be modulated, as could substrates, or signaling molecules associated with the CrRLK1L receptor like kinases including HERK1, HERK2, THE1 or FER could be modulated. The invention allows the identification of other signaling components that function in the HERK1/HERK2/THE/FER pathway to regulate plant growth and other processes. These components can be identified as proteins, peptides or small molecules that interact with these receptor-like kinases by immunoprecipitation and/or yeast two-hybrid screens. These other signaling components can be also identified by screening for genetic modifiers (suppressors and enhancers) of mutants of these receptor-like kinase genes.

In yet another embodiment, the method of modulating CrRLK1L receptor like kinase activity including HERK1, HERK2, THE1 or FER includes a HERK1, HERK2, THE1 or FER encoding polynucleotide which comprises, e.g., at least about 70%, at least about 75%, at least about 80%, at least about 85%, at least about 90%, at least about 95%, at least about 99%, at least about 99.5% or more sequence identity to SEQ ID NO:1 (HERK1), SEQ ID NO:3 (HERK2), SEQ ID NO:5 (THE1) or SEQ ID NO:7 (FER). Many plant CrRLK1L receptor like kinases including HERK1, HERK2, THE1 or FER from *Arabidopsis* and other plants are known to those of skill in the art and are readily available through sources such as GENBANK, and by isolation and characterization of homologues by methods disclosed herein.

In another embodiment, the invention relates to methods for improving plant yield traits such as growth, cell elongation and the like by providing an isolated or recombinant modified plant cell comprising at least one modification that modulates CrRLK1L receptor like kinase activity including HERK1, HERK2, THE1 or FER.

In one embodiment, the methods involving a modification in the plant cell include introducing at least one polynucleotide sequence comprising a CrRLK1L receptor like kinases including HERK1, HERK2, THE1 or FER nucleic acid sequence, or subsequence thereof, into a plant cell, such that the at least one polynucleotide sequence is operably linked to a promoter, and where the at least one polynucleotide sequence comprises, e.g., at least about 70%, at least about 75%, at least about 80%, at least about 85%, at least about 90%, at least about 95%, at least about 99%, about 99.5% or more sequence identity to SEQ ID NOS:1, 3, 5, or 7 or a subsequence thereof, or a complement thereof.

In certain embodiments, a plant cell resulting from the methods of the invention is from a dicot or monocot. In another aspect, the plant cell is in a plant comprising a sterility phenotype, e.g., a male sterility phenotype.

In yet another embodiment, the present invention is directed to a transgenic plant or plant cells with improved yield traits including plant growth, or cellular elongation, containing the nucleic acids described herein. Preferred plants grown from the methods of the present invention include but are not limited to maize, *Arabidopsis*, soybean, sunflower, sorghum, canola, wheat, alfalfa, cotton, oat, rice, barley, tomato, cacao and millet. In another embodiment, the transgenic plant is a maize plant or plant cells. Plants produced according to the invention can have at least one of the following phenotypes as compared to a non-modified control plant, including but not limited to: increased plant height, increased root length, increased leaf size, increased ear size, increased seed size, increased endosperm size, or increased plant size when compared to a non-modified plant under similar conditions.

Detection of expression products is performed either qualitatively (by detecting presence or absence of one or more product of interest) or quantitatively (by monitoring the level of expression of one or more product of interest). Aspects of the invention optionally include monitoring an expression level or activity of a nucleic acid, polypeptide or chemical as noted herein for detection of the same in a plant or in a population of plants.

In a further aspect, the present invention relates to a polynucleotide amplified from *Oryza sativa, Zea mays* or *Glycine max* nucleic acid library using primers which selectively hybridize, under stringent hybridization conditions, to loci within polynucleotides of the present invention.

DEFINITIONS

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "antibody" includes reference to antigen binding forms of antibodies (e.g., Faba, F (ab) 2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain FV, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., Science 246: 1275-1281 (1989); and Ward, et al., Nature 341: 544-546 (1989); and Vaughan et al., Nature Biotech. 14: 309-314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W.H. Freeman and Company.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein. When the nucleic acid is prepared or altered synthetically, advantage can be taken of known codon preferences of the intended host where the nucleic acid is to be expressed.

For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477-498 (1989)). Thus, the maize preferred codon for a particular amino acid may be derived from known gene sequences from maize. Maize codon usage for 28 genes from maize plants is listed in Table 4 of Murray et al., supra.

As used herein "full-length sequence" in reference to a specified polynucleotide or its encoded protein means having the entire amino acid sequence of, a native (nonsynthetic), endogenous, biologically active form of the specified protein. Methods to determine whether a sequence is full-length are well known in the art including such exemplary techniques as northern or western blots, primer extension, S 1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, Antibodies, A Laboratory Manual, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by nonnaturally occurring means to a locus of the genome not native to that nucleic acid. Nucleic acids which are "isolated" as defined herein, are also referred to as "heterologous" nucleic acids.

Unless otherwise stated, the term "HERK1, HERK2, FER or THE1 nucleic acid" means a nucleic acid comprising a polynucleotide (an "HERK1, HERK2, FER, or THE1 polynucleotide") encoding an HERK1, HERK2, FER, or THE1 polypeptide with HERK1, HERK2, FER, or THE1 activity and includes all conservatively modified variants, homologs paralogs and the like. An "HERK1, HERK2, FER, THE1 gene" is a gene of the present invention and refers to a heterologous genomic form of a full-length HERK1, HERK2, FER, or THE1 polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning-A Laboratory Manual, 2nd ed., Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of post translation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "HERK1, HERK2, FER, or THE1 polypeptide" is a polypeptide which has HERK1, HERK2, FER, or THE1 activity and refers to one or more amino acid sequences, in glycosylated or non-glycosylated form. The term is also inclusive of fragments, variants, homologs, alleles or precursors (e.g., preproproteins or proproteins) thereof which retain activity. An "HERK1, HERK2, FER, or THE1 protein" comprises a HERK1, HERK2, FER, or THE1 polypeptide. "HERK1, HERK2, FER, or THE1 activity" means that the polypeptide is capable of Ser/Thr kinase activity as measured by any number of available assays.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a s other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample. Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 MNaCl, 1% SDS (sodium dodecyl sulphate) at 37° C., and a wash in 1× to 2×SSC (20×SSC=3.0 MNaCl/0.3 M trisodium citrate) at 50° to 55° C. Exemplary moderate stringency conditions include hybridization in 40 to 45% formamide, 1 MNaCl, 1% SDS at 37° C., and a wash in <RTI 0.5× to 1×SSC at 55° to 60° C. Exemplary high stringency conditions include hybridization in 50% formamide, 1 MNaCl, 1% SDS at 37° C., and a wash in 0.1×SSC at 60° to 65° C. Specificity is typically the function of post-hybridization washes, the critical factors being the ionic strength and temperature of the final wash solution. For DNA/DNA hybrids, the Tm can be approximated from the equation of Meinkoth and Wahl, Anal. Biochem., 138: 267-284 (1984): Tm=81.5 C+16.6 (log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a)"reference sequence", (b)"comparison window", (c) "sequence identity", and (d)"percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the GCG Wisconsin Genetics Software Package, Version 10 (available from Accelrys Inc., 9685 Scranton Road, San Diego, Calif., USA). The CLUSTAL program is well described by Higgins and Sharp, Gene 73:237-244 (1988); Higgins and Sharp, CABIOS 5:151-153 (1989); Corpet, et al., Nucleic Acids Research 16: 10881-90 (1988); Huang, et al., Computer Applications in the Biosciences 8:155-65 (1992), and Pearson, et al., Methods in Molecular Biology 24:307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215:403-410 (1990); and, Altschul et al., Nucleic Acids Res. 25:3389-3402 (1997).

Software for performing BLAST analyses is publicly available, e.g., through the National Center for Biotechnology Information www at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). One measure of similarity provided by the BLAST algorithm is the smallest sum probability (P(N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters can be employed alone or in combination.

Unless otherwise stated, nucleotide and protein identity/ similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (J. Mol. Biol. 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Multiple alignment of the sequences can be performed using the CLUSTAL method of alignment (Higgins and Sharp (1989) CABIOS. 5:151-153) with the default parameters (GAPPENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

DETAILED DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows that HERK1, THE1 and FER are related receptor-like kinases are induced by BRs. (1A) The expression of HERK1, THE1 and FER is induced by BL treatment in 10-day-old seedlings and 4-week-old adult plants. Triplicate biological samples were used to prepare RNA for quantitative RT PCR. The relative expression levels compared to UBQ5 gene were used to determine the BL-induction levels of each gene. The averages and standard deviations from three biological repeats are shown. (1B) HERK1, THE1 and FER are up-regulated in bes1-D and down-regulated in bri1. Ten-day-old seedlings were used to prepare RNA for qRT-PCR as described in (1A). (1C-E) HERK1 cellular localization: A HERK1-GFP (1C) or BES1-D-GFP (1D) construct was introduced into protoplasts or transgenic plants (1E). HERK1 is mostly localized at the plasma membrane (1C and 1E), while BES1-D is primarily in the nucleus (1D). The bars represent 10 m in C and D. (1F) HERK1 displayed kinase activity. Recombinant proteins fused with MBP representing the wild-type HERK1 kinase domain (WT), and a mutant version with disrupted kinase activity (mutant), were used in kinase assay. Autophosphorylation was detected by phosphorimaging, and the proteins were detected by SYPRO RUBY staining (1G-1I) The expression patterns of HERK1, THE1 and FER in 10-day-old seedlings (1G and 1H) or 3-week-old adult leaves (1I) as revealed by GUS reporter gene. The bars in 1G/1H and 1I represent 2.5 and 10 mm, respectively.

Figure 2:
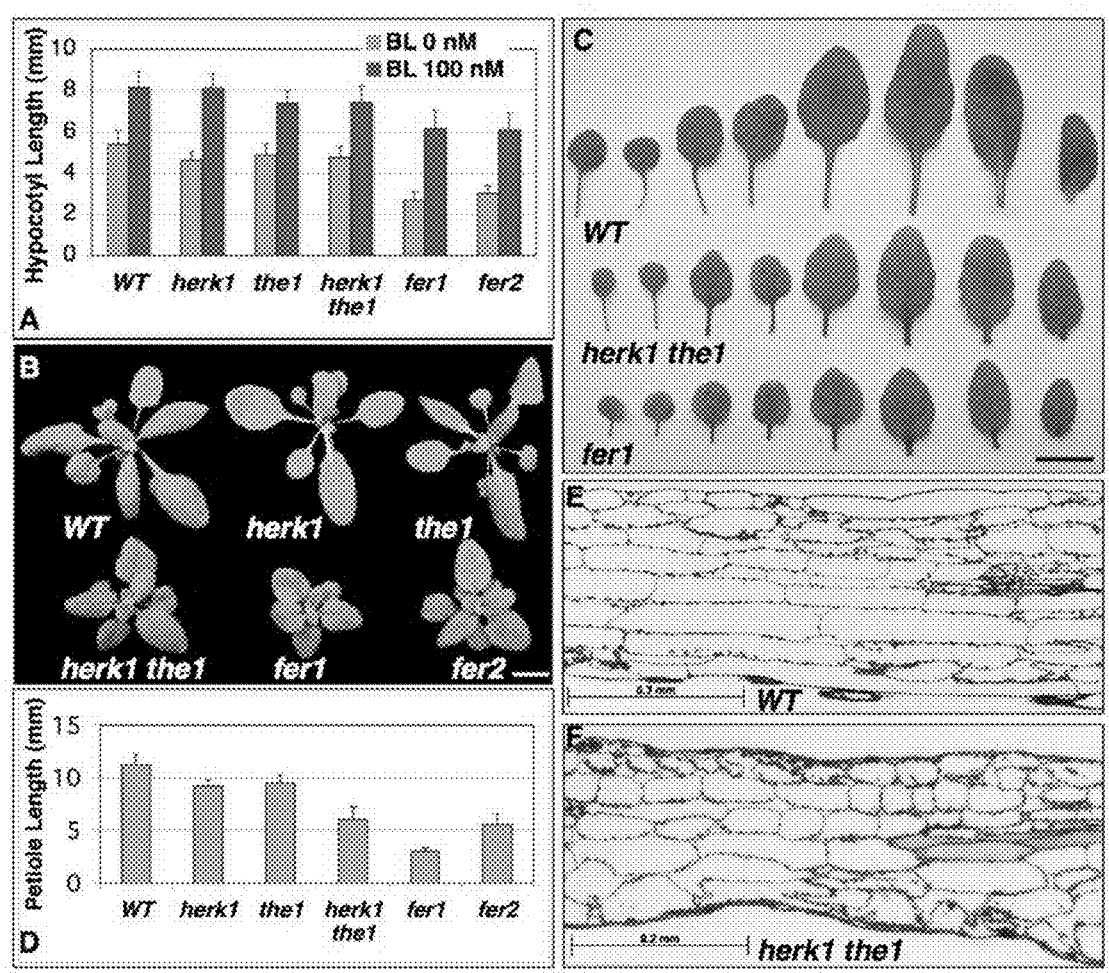

FIG. 2 shows that HERK1, THE1 and FER are required for cell elongation. (2A) BR responses of the herk1, the1 and fer mutants at the seedling stage. The seeds were germinated in ½ MS media containing the indicated concentrations of brassinolide (BL) and grown under the light for 10 days. 20-30 hypocotyls were measured, and the average hypocotyl lengths and standard deviations are presented. (2B) Shoot phenotypes of 24-day-old adult plants. The bar represents 10 mm. (2C) The leaves of the WT, herk1 the1 double and fer1 mutants, showing the reduced lengths in leaf blades and leaf petioles. The bar represents 10 mm. (2D) Quantification of petiole lengths of the sixth leaf in WT and mutants. Averages and standard deviations from 10 plants are shown. (2E and 2F) The herk1 the1 double mutant plants have reduced cell elongation. The petioles of the WT (2E) and herk1 the1 double mutant (2F) plants were fixed, stained with toluidine blue, and embedded. Longitudinal sections were examined under a bright-field light microscope and photographed. The sections shown are midway along the length of the petioles and cut through the center (traces of vascular tissues can be seen on both WT and mutant sections on the right side).

Figure 3:
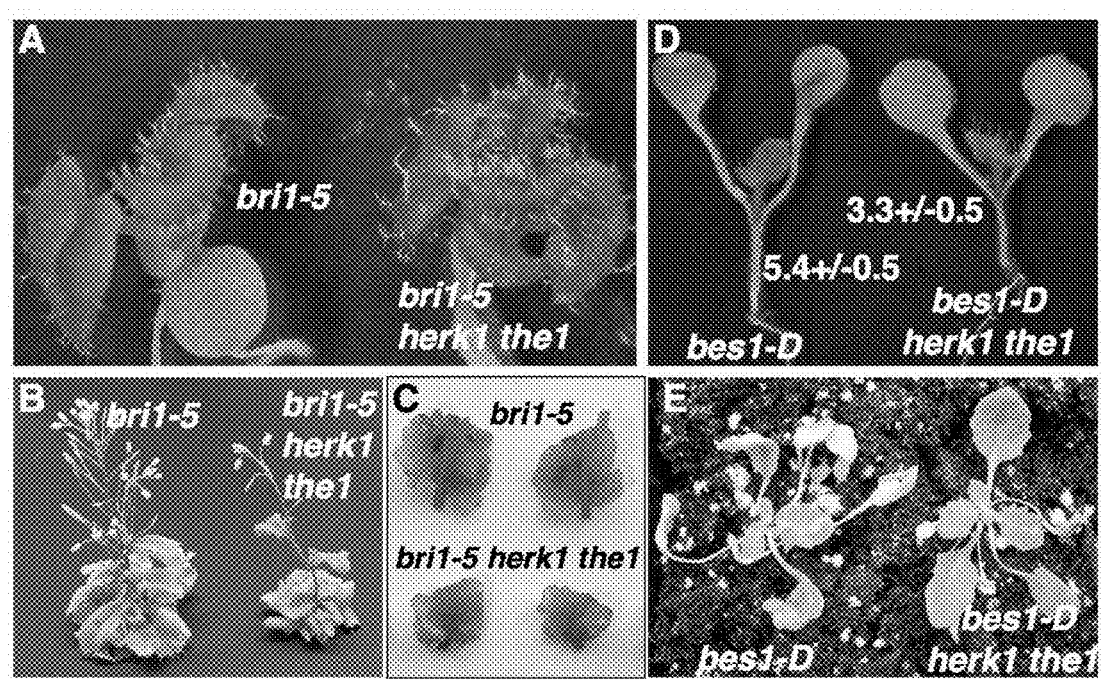

FIG. 3 shows that herk1 the1 double mutant enhances bri1-5 and suppresses bes1-D mutant phenotypes. (3A) Two-week-old seedlings. (3B) Adult plants (about 35-day-old). (3C) Fifth and sixth leaves. (3D) Nine-day-old seedlings. (3E) Adult plants (about 24-day-old). Note that one of the leaves from the bes1-D herk1 the1 plant was removed for genotyping.

Figure 4:
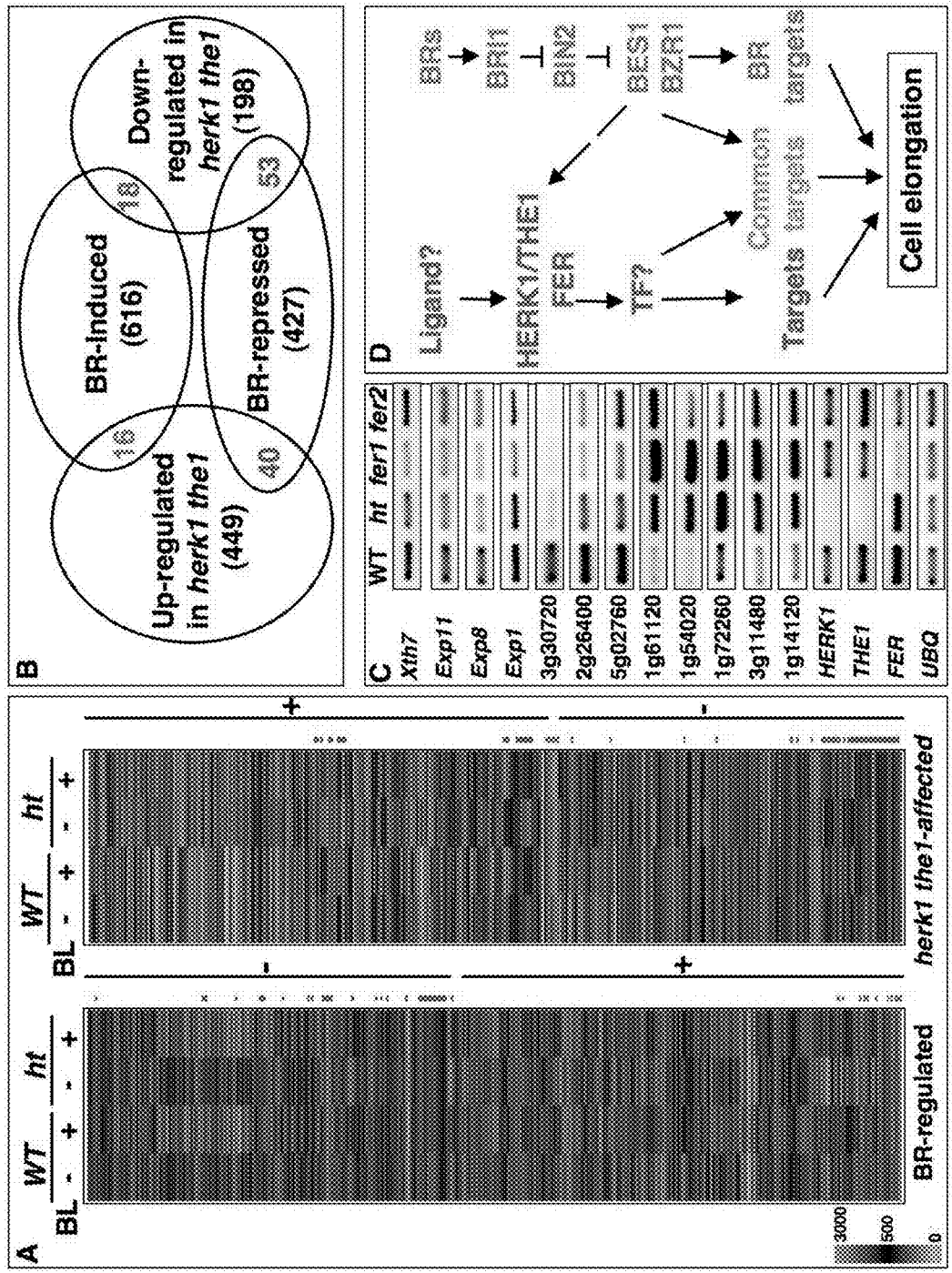

FIG. 4 shows that HERK1/THE1/FER and BR pathways affect independent genes with some overlap. (4A) Cluster analysis of BR-regulated genes in WT and mutant plants. The majority of BL-repressed genes (marked by −) and BL-induced genes (marked by +) are not affected in herk1 the1 double mutant (ht). Likewise, the majority of genes down-regulated (−) or up-regulated (+) in herk1 the1 double mutant are not regulated by BRs. The overlap between BR- and HERK1/THE1-affected genes are indicated by colored bars corresponding to the colored numbers in the overlaps shown in FIG. 4B. (4B) A diagram showing the overlap of BR- and HERK1/THE1-regulated genes. Lists of the genes represented in this diagram are presented in Supplementary Table S1-4. (4C) Semi-quantitative PCR with primers from indicated genes to confirm the microarray data in the herk1 the1 double mutant (ht) and to examine the expression levels in fer1 and fer2 mutants. Genes either down- or up-regulated in the herk1 the1 double mutant as well as the 3 receptor genes were tested. (4D) A model for the BR- and HERK1/THE1-pathways in the regulation of cell elongation. See text for details. TF stands for putative transcription factor.

Figure 5:
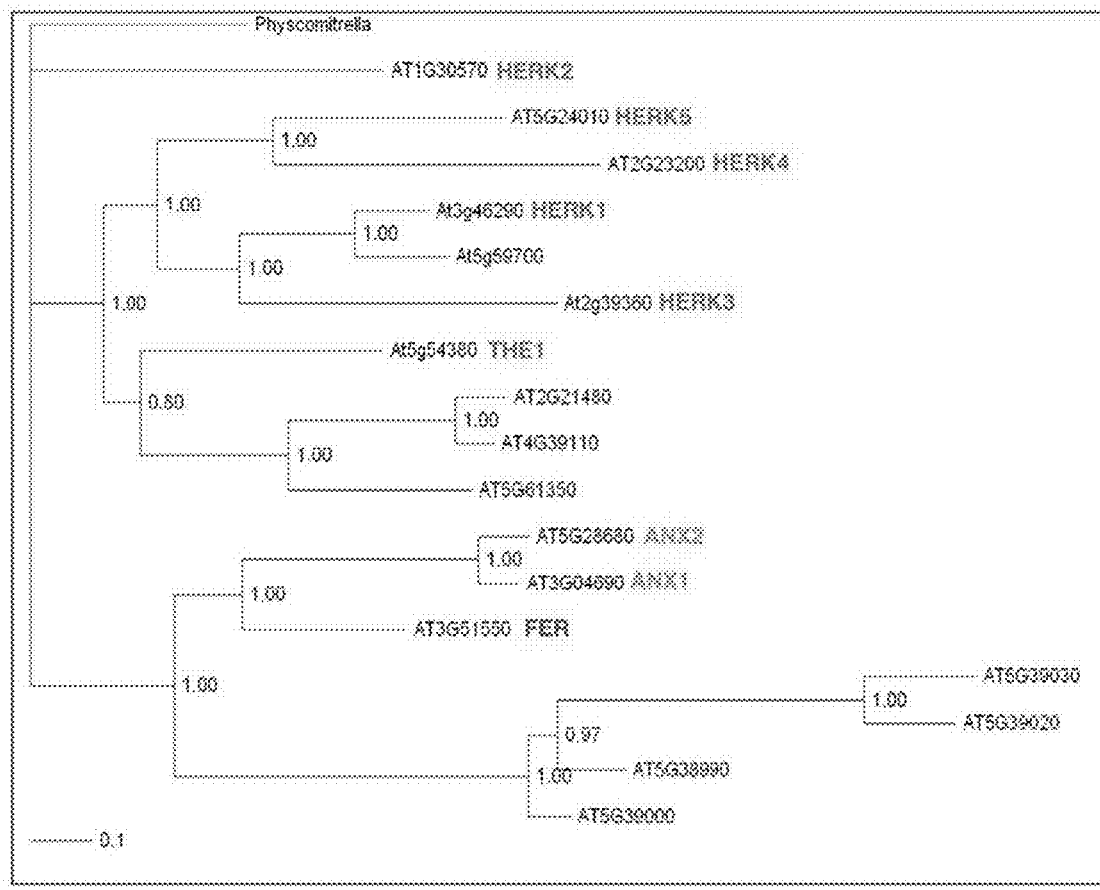

FIG. 5 shows that *Arabidopsis* HERK1, THE1 and FER are related RLKs in the CrRLK family. We obtained all protein sequences from NCBI, which were then aligned by ClustalX 2.0 (http://bips.u-strasbg.fr/fr/Documentation/ClustalX/). Mrbayes program (http://mrbayes.csit.fsu.edu/index.php) was used to reconstruct the evolutionary tree of 17 CrRLK proteins and the tree was viewed by TreeViewX (http://darwin.zoology.gla.ac.uk/~rpage/treeviewx/). A CrRLK homolog in *Physcomitrella patens* (XP_001760700) was used as the outgroup during the analysis. After 500,000 iterations in Mrbayes, the split frequency reached as low as 0.005, which indicates high confidence that convergence occurred. The numbers on the tree indicated the posterior probability of each Glade (bigger posterior probability indicates higher confidence).

Figure 6:
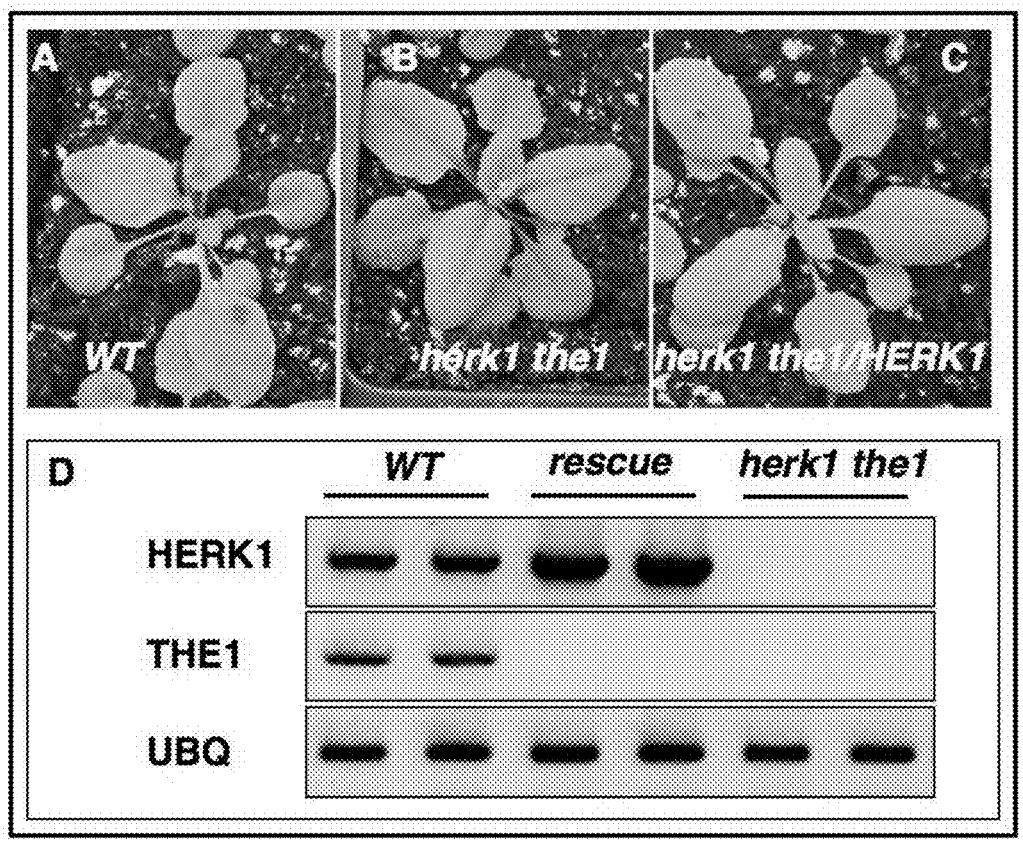

FIG. 6 demonstrates that the expression of HERK1 in herk1 the1 mutant background rescued the mutant phenotype. A full-length genomic clone of HERK1 was transformed into the double mutant plants by floral-dip method. (A-C) Four-week-old wild-type (WT, A), herk1 the1 mutant (B) and one of the representative rescued T2 plant lines (C) are shown. (D) RNAs prepared from these plant lines were used in RT-PCR to detect the expression of HERK1 and THE1. UBQ5 gene was used as a control.

Figure 7:
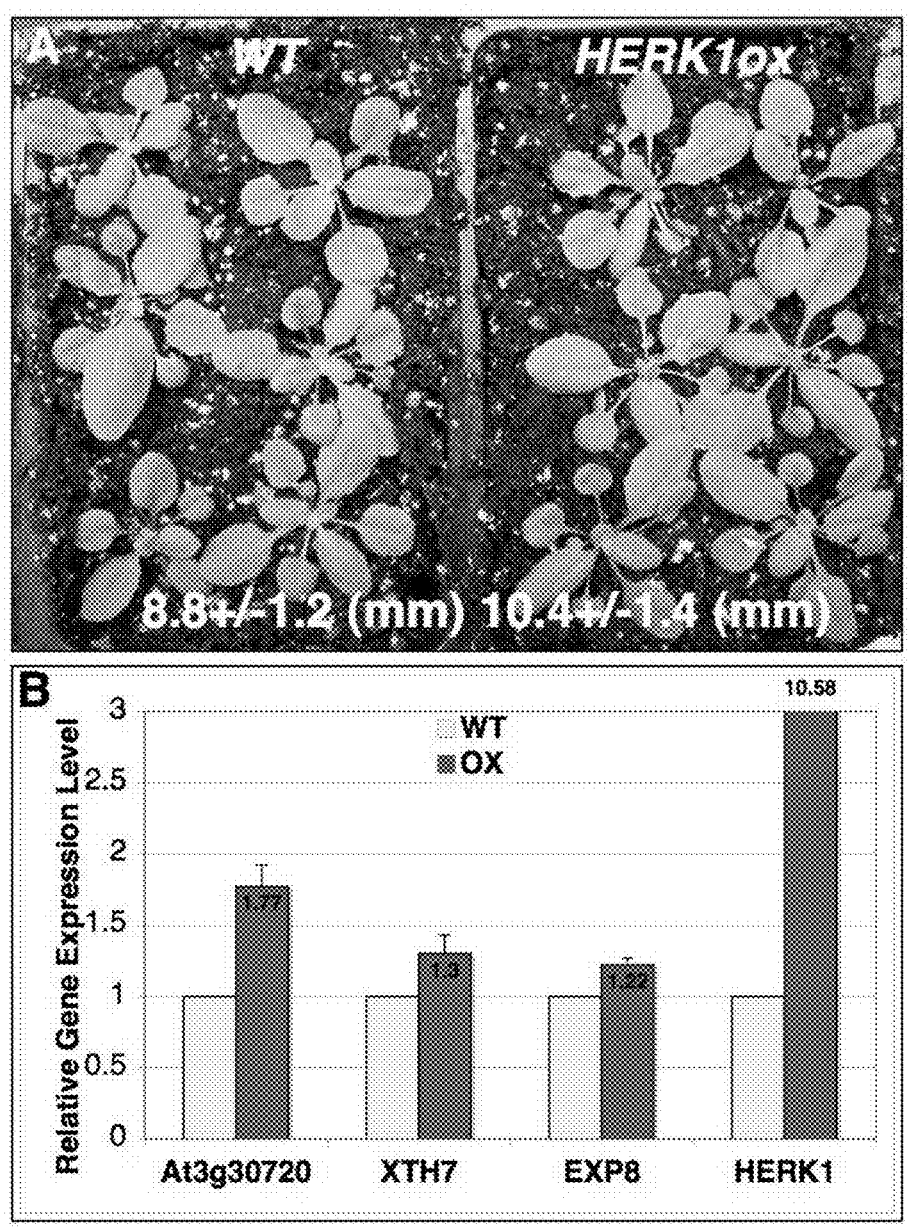

FIG. 7 shows a HERK1 Overexpression phenotype. (7A) The image showed 22-day-old plants of WT and a HERK1 overexpression line (HERK1ox). The overexpression lines were identified from transgenic plants carrying the HERK1 genomic clone including the promoter. As indicated in the figure, overexpression transgenic plants have slightly increased petiole lengths compared to WT (average and standard deviations from 10 transgenic plants). The difference was significant according to student's t-test (p<0.1). (7B) Several genes down-regulated in herk1 the1 mutant (FIG. 4) are increased in HERK1 overexpression plants. The relatively subtle phenotype of the HERK1 overexpression lines (despite the fact the gene was overexpressed 10 times with its native promoter) suggests that other components in the HERK pathway (such as ligand, co-receptor and/or downstream signaling components) are likely more rate-limiting.

Figure 8:
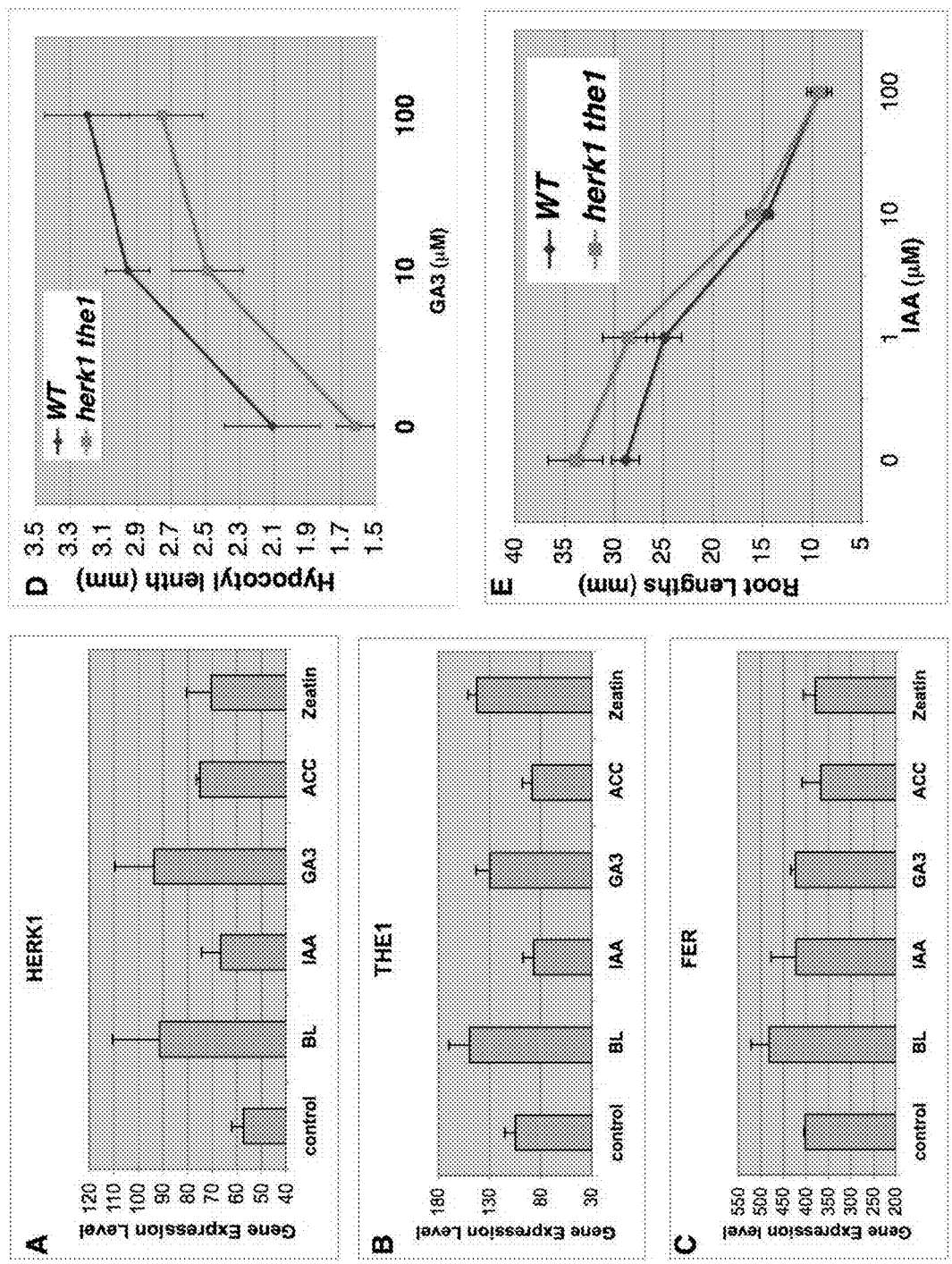

FIG. 8 shows the regulation of CrRLK genes and Gibberellin (GA)/Auxin Responses of herk1 the1 Double Mutant. (8A) Regulation of HERK1, THE1 and FER as well as other CrRLK family members by BL. The data are derived from microarray experiments with light-growing seedlings treated with 10 nM BL for 3 hr, which is published in a public website (http://bbc.botany.utoronto.ca/efp/cgi-bin/efpWeb.cgi). (8B) Regulation of HERK1, THE1 and FER by GA3 and auxin (IAA) in 10-day-old seedlings as revealed by qRT-PCR. The averages and standard deviations for 2 biological replicates are shown. (8C) the herk1 the1 double mutant has a normal GA response in a hypocotyl elongation assay. The seeds were germinated in ½ MS media containing the indicated concentrations of GA3 and grown under the light for 10 days. (8D) herk1 the1 double mutants had a slightly increased response to auxin in root elongation assay. Seeds were germinated and grown in media with the indicated concentration of IAA in vertical plates for 11 days. The increased sensitivity to IAA may be due to reduced BR response in herk1 the1 double mutant since BR loss-of-function mutants also display hypersensitivity to auxin in root elongation assays (1). The averages and standard deviations are derived from 20-30 samples for both GA and IAA response experiments. (Ephritikhine G, Fellner M, Vannini C, Lapous D, Barbier-Brygoo H (1999) The sax dwarf mutant of *Arabidopsis thaliana* shows altered sensitivity of growth responses to abscisic acid, auxin, gibberellins and ethylene and is partially rescued by exogenous brassinosteroid. *Plant J* 18: 303-314).

Figure 9:
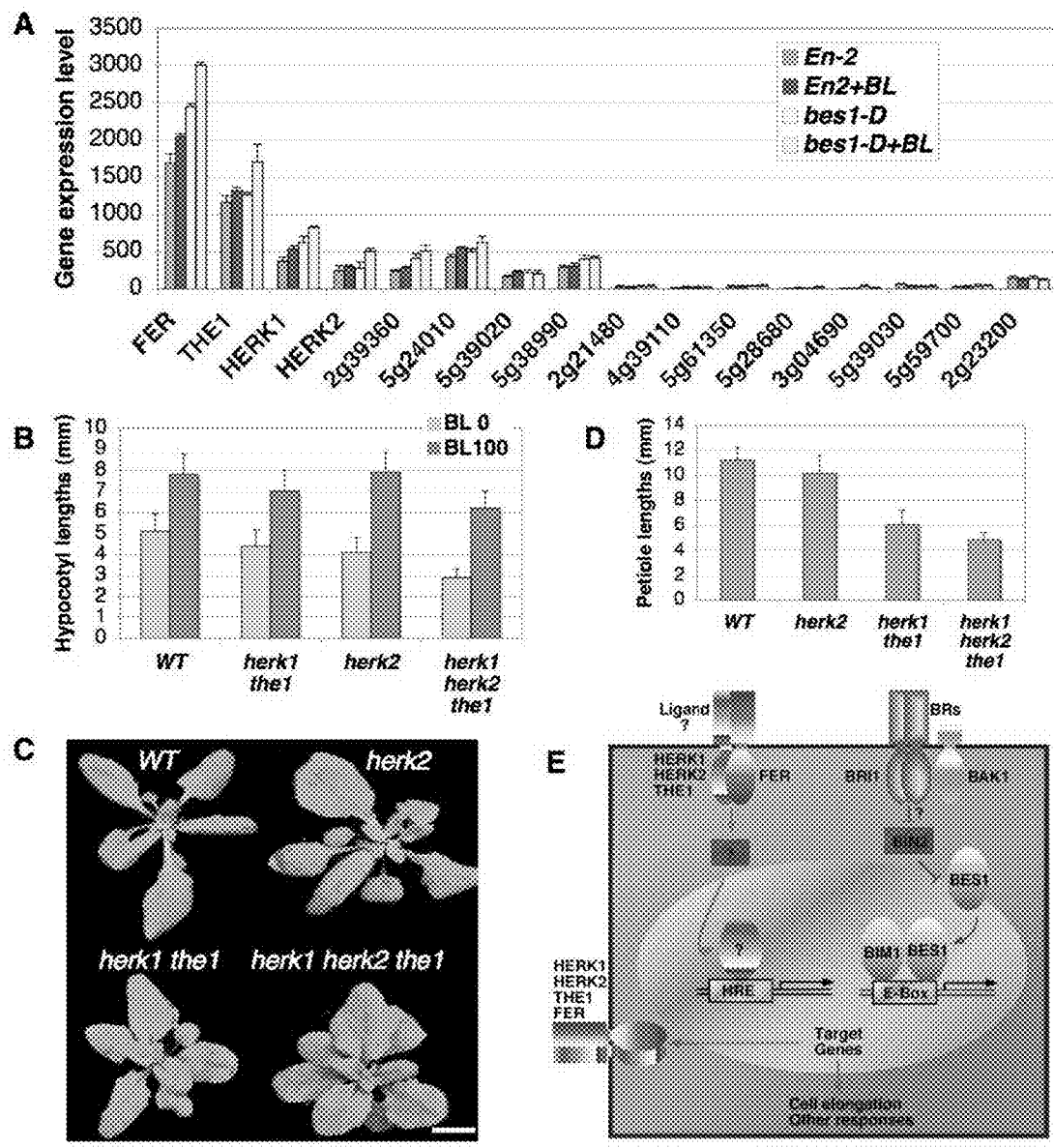

FIG. 9 demonstrates that HERK1, HERK2, THE1 and FER are regulated by BL/BES1 and are required for cell elongation. (9A) The expression of CrRLK family RLKs by BL in WT and bes1-D mutant. Microarrays were performed with 2-week-old seedlings with or without BL treatment (1 uM, 3 hr). At5g38990 and At5g39000 have the same probe set in Affymetrix ATH1 Genome arrays, so only the former is shown. (9B) BR responses of the indicated mutants at the seedling stage, performed as described. (9C) Plant phenotypes of 24-day-old adult plants. The bar represents 10 mm. (9D) Petiole lengths of the sixth leaf in WT and mutants. Averages and standard deviations from 10 plants are shown. (E) A model for HERK signaling and its crosstalk with BR pathway.

Figure 10:
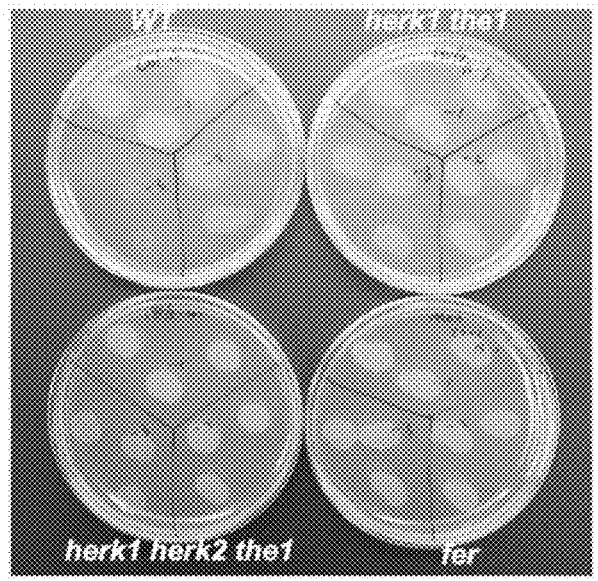

FIG. 10 shows that herk1 the1, herk1 herk2 the1 and fer mutants accumulate more bacteria of *Pseudomonas syringae*. Same amount of bacteria were infiltrated to one-month-old wild-type (WT) and mutant plant leaves. Two-day after the inoculation, same amount of leaf tissues were ground in water and diluted 10, 100 and 1000 times (indicated as −1, −2, and −3). The bacterial amounts were determined by spotting 100 ul of each of the dilutions onto bacterial plates. The bacterial plates were grown at 30 C for two days. The results were confirmed by quantifications, which indicate that the mutants usually accumulate 5-10 times more bacteria than the WT.

Figure 11:
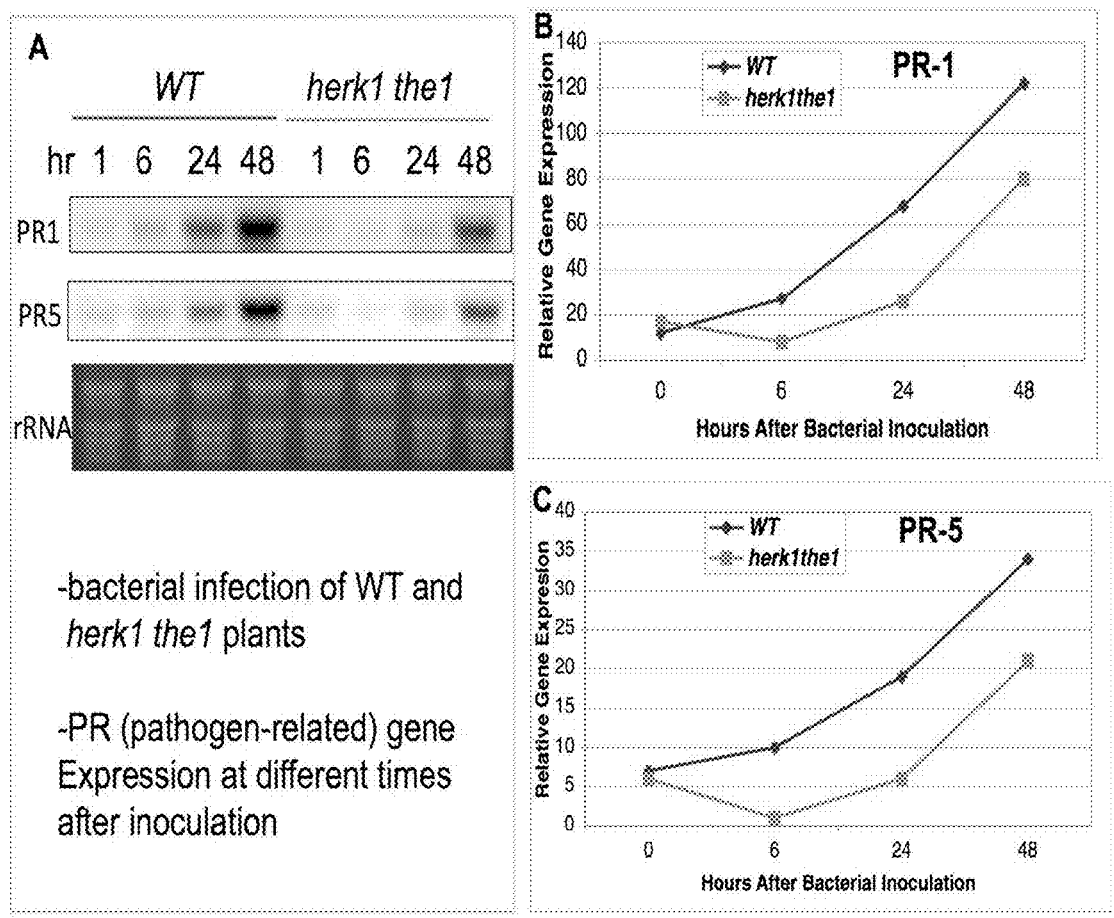

FIG. 11 shows that Pathogen-related (PR) gene expression is compromised in herk1 the1 mutant. WT and herk1 the1 plants were infiltrated with *Pseudomonas syringae*. RNA were prepared from infected plants after indicated times. Northern blotting was performed with PR1 and PR5 genes (A). The loading of RNA was indicated by ribosomal RNA (rRNA). The expression of PR1 (B) and PR5 (C) in WT and herk1 the1 were quantified and plotted.

DETAILED DESCRIPTION OF THE INVENTION

The invention comprises the discovery of a new pathway for plant growth and cellular elongation in plants. As such methods are disclosed for improving plant growth by modulating the activity of one or more components of this pathway, including members of the family of CrRLK1L family of receptor like kinases which have been identified herein as within this pathway. Methods are also disclosed for identifying other signaling components in this pathway.

According to the invention, applicants have found that the CrRLK1L receptor like kinases HERK1 (At3g46290) and HERK2 (At1g30570), THE1, and FER all function in a novel pathway of plant growth and their activity may be modulated in a plant to improve growth, cellular elongation, and other yield related traits when compared to a non modulated plant. Other family members such as At2g39360 and At5g24010, as well as analogues and homologues from other receptor like kinases and other plant species will be expected to have similar affects.

Thus, the invention in one aspect provides a method for enhancing yield-related traits such as plant growth and cellular elongation in plants relative to control plants, comprising modulating the activity or expression in a plant of a nucleic acid encoding a HERK1, HERK2, THE1, or FER protein, or a part thereof. THE1 and FER had previously been identified as having cellular elongation inhibiting affects in response to cell damage, and in pollen tube elongation leading to eruption of the pollen tip and release of sperm. Quite surprisingly, applicants have found that these proteins have the opposite affect for a non-wounded plant in vegetative growth and that they may be up regulated to increase plant growth and cellular elongation. In fact, all three proteins HERK1, FER and THE1 were found to work together to improve growth, as deleterious mutants of all three resulted in dwarf plants. Such plants may also be used to identify other signaling molecules from this pathway. Thus the invention also includes modulating the activity of FER and THE1 in healthy plant vegetative growth situations and in a preferred embodiment modulation of all three together to optimize plant growth, cellular elongation and other plant yield characteristics.

The present invention therefore provides methods for enhancing yield-related traits in plants relative to control plants, comprising preferentially modulating the activity of a CrRLK1L receptor like kinases HERK1, HERK2, THE1 or FER or a combination thereof or modulating the expression in a plant seed or seed parts of a nucleic acid encoding one or more CrRLK1L receptor like kinases HERK1, HERK2, THE1 or FER or a combination thereof.

To the extent that this pathway is influenced by brassinosteroids, applicants have further found that the transcription factor BEST (BRIT-EMS-SUPPRESSOR 1); a regulator of the brassinosteroid pathway up regulates HERK1, HERK2, THE1, and FER. The invention in another aspect provides a method for enhancing yield-related traits such as plant growth and cellular elongation in plants relative to control plants, comprising modulating the activity of a BES1 protein or modulating the expression in a plant of a nucleic acid encoding a BES1 transcription factor protein, or a part thereof.

In other embodiments, other steps along this novel plant growth or signaling pathway could be modulated. For example, BES1 or other brassinosteroid components found to affect this pathway could be modulated, as could substrates, or signaling molecules associated with the CrRLK1L receptor like kinases including HERK1, HERK2, THE1 or FER could be modulated. The invention allows the identification of other signaling components that function in the HERK1/HERK2/THE/FER pathway to regulate plant growth and other processes. These components can be identified as proteins, peptides or small molecules that interact with these receptor-like kinases by immunoprecipitation and/or yeast two-hybrid screens. These other signaling components can be also identified by screening for genetic modifiers (suppressors and enhancers) of mutants of these receptor-like kinase genes.

In another embodiment, the method of modulating CrRLK1L receptor like kinase activity including HERK1, HERK2, THE1 or FER includes a HERK1, HERK2, THE1 or FER encoding polynucleotide which comprises, e.g., at least about 70%, at least about 75%, at least about 80%, at least about 85%, at least about 90%, at least about 95%, at least about 99%, at least about 99.5% or more sequence identity to SEQ ID NO:1 (HERK1), SEQ ID NO:3 (HERK2), SEQ ID NO:5 (THE1) or SEQ ID NO:7 (FER). Many plant CrRLK1L receptor like kinases including HERK1, HERK2, THE1 or FER from *Arabidopsis* and other plants are known to those of skill in the art and are readily available through sources such as GENBANK, and by isolation and characterization of homologues by methods disclosed herein.

In another embodiment, the invention relates to methods for improving plant yield traits such as growth, cell elongation and the like by providing an isolated or recombinant modified plant cell comprising at least one modification that modulates CrRLK1L receptor like kinase activity including HERK1, HERK2, THE1 or FER.

In one embodiment, the methods involving a modification in the plant cell include introducing at least one polynucleotide sequence comprising a CrRLK1L receptor like kinases including HERK1, HERK2, THE1 or FER nucleic acid sequence, or subsequence thereof, into a plant cell, such that the at least one polynucleotide sequence is operably linked to a promoter, and where the at least one polynucleotide sequence comprises, e.g., at least about 70%, at least about 75%, at least about 80%, at least about 85%, at least about 90%, at least about 95%, at least about 99%, about 99.5% or more sequence identity to SEQ ID NOS:1, 3, 5, or 7 or a subsequence thereof, or a complement thereof.

In certain embodiments, a plant cell resulting from the methods of the invention is from a dicot or monocot. In another aspect, the plant cell is in a plant comprising a sterility phenotype, e.g., a male sterility phenotype.

In yet another embodiment, the present invention is directed to a transgenic plant or plant cells with improved yield traits including plant growth, or cellular elongation, containing the nucleic acids described herein. Preferred plants grown from the methods of the present invention include but are not limited to maize, *Arabidopsis*, soybean, sunflower, sorghum, canola, wheat, alfalfa, cotton, oat, rice, barley, tomato, cacao and millet. In another embodiment, the transgenic plant is a maize plant or plant cells. Plants produced according to the invention can have at least one of the following phenotypes as compared to a non-modified control plant, including but not limited to: increased plant height, increased root length, increased leaf size, increased ear size, increased seed size, increased endosperm size, or increased plant size when compared to a non-modified plant under similar conditions.

Detection of expression products is performed either qualitatively (by detecting presence or absence of one or more product of interest) or quantitatively (by monitoring the level of expression of one or more product of interest). Aspects of the invention optionally include monitoring an expression level or activity of a nucleic acid, polypeptide or chemical as noted herein for detection of the same in a plant or in a population of plants.

In a further aspect, the present invention relates to a polynucleotide amplified from a *Zea mays* or *Glycine max* nucleic acid library using primers which selectively hybridize, under stringent hybridization conditions, to loci within polynucleotides of the present invention.

Methods of the invention may be practiced using a number of known techniques, many of which are set forth below.

Nucleic Acids

The present invention provides, inter alia, isolated nucleic acids of RNA, DNA, homologs, paralogs and orthologs and/or chimeras thereof, comprising CrRLK polynucleotides which function in a new plant growth signaling pathway. This includes naturally occurring as well as synthetic variants and homologs of the sequences.

Sequences homologous, i.e., that share significant sequence identity or similarity, to those provided herein derived *Arabidopsis thaliana* or from other plants of choice, are also an aspect of the invention. Homologous sequences can be derived from any plant including monocots and dicots and in particular agriculturally important plant species, including but not limited to, crops such as soybean, wheat, corn (maize), potato, cotton, rice, rape, oilseed rape (including canola), sunflower, alfalfa, clover, sugarcane, and turf; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts, and kohlrabi). Other crops, including fruits and vegetables, whose phenotype can be changed and which comprise homologous sequences include barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, and sweet potato; and beans. The homologous sequences may also be derived from woody species, such pine, poplar and eucalyptus, or mint or other labiates. In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (*maize*).

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al. (1994) Nucleic Acids Res. 22:4673-4680; Higgins et al. (1996) Methods Enzymol. 266:383-402). Groups of similar genes can also be identified with pair-wise BLAST analysis (Feng and Doolittle (1987) J. Mol. Evol. 25:351-360).

For example, a Glade of very similar MADS domain transcription factors from *Arabidopsis* all share a common function in flowering time (Ratcliffe et al. (2001) Plant Physiol. 126: 122-132), and a group of very similar AP2 domain transcription factors from *Arabidopsis* are involved in tolerance of plants to freezing (Gilmour et al. (1998) Plant J. 16:433-442). Analysis of groups of similar genes with similar function that fall within one Glade can yield subsequences that are particular to the Glade. These subsequences, known as consensus sequences, can not only be used to define the sequences within each Glade, but define the functions of these genes; genes within a Glade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Variant Nucleotide Sequences in the Non-Coding Regions

The CrRLK polynucleotides (HERK1, HERK2, THE, FER) which function in the new plant growth signaling pathway are used to generate variant nucleotide sequences having the nucleotide sequence of the 5'-untranslated region, 3'-untranslated region, or promoter region that is approximately 70%, 75%, 80%, 85%, 90% and 95% identical to the original nucleotide sequence of the corresponding SEQ ID NO: 1, 3, 5 or 7. These variants are then associated with natural variation in the germplasm for component traits related to cellular elongation and plant growth. The associated variants are used as marker haplotypes to select for the desirable traits.

Variant Amino Acid Sequences of Polypeptides

Variant amino acid sequences of the CrRLK (HERK1, HERK2, THE, FER polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined herein is followed. Variants having about 70%, 75%, 80%, 85%, 90% and 95% nucleic acid sequence identity are generated using this method. These variants are then associated with natural variation in the germplasm for component traits related to plant growth and cellular elongation. The associated variants are used as marker haplotypes to select for the desirable traits.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The CrRLK polynucleotides (HERK1, HERK2, THE, FER) comprise isolated polynucleotides which are inclusive of:

(a) a polynucleotide encoding a HERK1, HERK2, THE, FER polypeptide and conservatively modified and polymorphic variants thereof;

(b) a polynucleotide having at least 70% sequence identity with polynucleotides of (a) or (b);

(c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20):1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066.

Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30); and maize H3 histone (Lepetit, et al., (1992) *Mol. Gen. Genet.* 231:276-85; and Atanassvoa, et al., (1992) *Plant Journal* 2(3):291-300); ALS promoter, as described in PCT Application No. WO 96/30530; and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50; and An, et al., (1989) *Plant Cell* 1:115-22); and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell. Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, *The Maize Handbook*, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) Gene 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference), or signal peptides which target proteins to the plastids such as that of rapeseed enoyl-Acp reductase (Verwaert, et al., (1994) *Plant Mol. Biol.* 26:189-202) are useful in the invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al. (1987), *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger, et al., (1989) *Proc. Natl. Acad. Sci. USA,* 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7$^{th}$ ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol.* 45:773-81 (1983)). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the HERK1, HERK2, THE, FER gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert CrRLK polynucleotides which function in applicant's plant growth signaling pathway into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., *Science* 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in *Methods in Plant Molecular Biology and Biotechnology, supra*, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722), and ballistic particle acceleration (see, for example, Sanford, et al., U.S. Pat. No. 4,945,050; WO 91/10725; and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas (1984) *Nature* (London) 311:763-764; Bytebierm, et al., (1987) *Proc. Natl. Acad. Sci. USA* 84:5345-5349 (Liliaceae); De Wet, et al., (1985) *In The Experimental Manipulation of Ovule Tissues*, ed. G. P. Chapman, et al., pp. 197-209. Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. Pat. No. 913,914, filed Oct. 1, 1986, as referenced in U.S. Pat. No. 5,262,306, issued Nov. 16, 1993; and Simpson, et al., (1986) *Plant Mol. Biol.* 6:403-15 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theon. Appl. Genet.* 69:235-40; U.S. Pat. No. 4,658,082; Simpson, et al., supra; and U.S. Pat. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 µm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) *Abstracts of the VIIth Intl. Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Increasing the Activity and/or Level of a HERK1, HERK2, THE, FER Polypeptide

Methods are provided to increase the activity and/or level of the HERK1, HERK2, THE, FER polypeptides to increase cellular elongation and plant growth. An increase in the level and/or activity of the HERK1, HERK2, THE, FER polypeptide can be achieved by providing to the plant a HERK1, HERK2, THE, FER polypeptide. The HERK1, HERK2, THE, FER polypeptide can be provided by introducing the amino acid sequence encoding the HERK1, HERK2, THE, FER polypeptide into the plant, introducing into the plant a nucleotide sequence encoding a HERK1, HERK2, THE, FER polypeptide or alternatively by modifying a genomic locus encoding the HERK1, HERK2, THE, FER polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having enhanced nitrogen utilization activity. It is also recognized that the methods of the invention may employ a polynucleotide that is not capable of directing, in the transformed plant, the expression of a protein or an RNA. Thus, the level and/or activity of a HERK1, HERK2, THE, FER polypeptide may be increased by altering the gene encoding the HERK1, HERK2, THE, FER polypeptide or its promoter. See, e.g., Kmiec, U.S. Pat. No. 5,565,350; Zarling, et al., PCT/US93/03868. Therefore mutagenized plants that carry mutations in HERK1, HERK2, THE, FER genes, where the mutations increase expression of the HERK1, HERK2, THE, FER gene or increase the HERK1, HERK2, THE, FER activity of the encoded HERK1, HERK2, THE, FER polypeptide are provided.

Reducing the Activity and/or Level of a HERK1, HERK2, THE, FER Polypeptide

Methods are provided to reduce or eliminate the activity of a HERK1, HERK2, THE, FER polypeptide of the invention by transforming a plant cell with an expression cassette that expresses a polynucleotide that inhibits the expression of the HERK1, HERK2, THE, FER polypeptide. The polynucleotide may inhibit the expression of the HERK1, HERK2, THE, FER polypeptide directly, by preventing transcription or translation of the HERK1, HERK2, THE, FER messenger RNA, or indirectly, by encoding a polypeptide that inhibits the transcription or translation of an HERK1, HERK2, THE, FER gene encoding HERK1, HERK2, THE, FER polypeptide. Methods for inhibiting or eliminating the expression of a gene in a plant are well known in the art, and any such method may be used in the present invention to inhibit the expression of HERK1, HERK2, THE, FER polypeptide.

In accordance with the present invention, the expression of HERK1, HERK2, THE, FER polypeptide is inhibited if the protein level of the HERK1, HERK2, THE, FER polypeptide is less than 70% of the protein level of the same HERK1, HERK2, THE, FER polypeptide in a plant that has not been genetically modified or mutagenized to inhibit the expression of that HERK1, HERK2, THE, FER polypeptide. In particular embodiments of the invention, the protein level of the HERK1, HERK2, THE, FER polypeptide in a modified plant according to the invention is less than 60%, less than 50%, less than 40%, less than 30%, less than 20%, less than 10%, less than 5%, or less than 2% of the protein level of the same HERK1, HERK2, THE, FER polypeptide in a plant that is not a mutant or that has not been genetically modified to inhibit the expression of that HERK1, HERK2, THE, FER polypeptide. The expression level of the HERK1, HERK2, THE, FER polypeptide may be measured directly, for example, by assaying for the level of HERK1, HERK2, THE, FER polypeptide expressed in the plant cell or plant, or indirectly, for example, by measuring the phenotypic changes in the plant. Methods for performing such assays are described elsewhere herein.

In other embodiments of the invention, the activity of the HERK1, HERK2, THE, FER polypeptide is reduced or eliminated by transforming a plant cell with an expression cassette comprising a polynucleotide encoding a polypeptide that inhibits the activity of a HERK1, HERK2, THE, FER polypeptide. The HERK1, HERK2, THE, FER activity of a HERK1, HERK2, THE, FER polypeptide is inhibited according to the present invention if the activity of the HERK1, HERK2, THE, FER polypeptide is less than 70% of the activity of the same HERK1, HERK2, THE, FER polypeptide in a plant that has not been modified to inhibit the HERK1, HERK2, THE, FER activity of that polypeptide. In particular embodiments of the invention, the HERK1, HERK2, THE, FER activity of the HERK1, HERK2, THE, FER polypeptide in a modified plant according to the invention is less than 60%, less than 50%, less than 40%, less than 30%, less than 20%, less than 10%, or less than 5% of the HERK1, HERK2, THE, FER activity of the same polypeptide in a plant that that has not been modified to inhibit the expression of that HERK1, HERK2, THE, FER polypeptide. The HERK1, HERK2, THE, FER activity of a HERK1, HERK2, THE, FER polypeptide is "eliminated" according to the invention when it is not detectable by the assay methods described elsewhere herein. Methods of determining the alteration of nitrogen utilization activity of a HERK1, HERK2, THE, FER polypeptide are described elsewhere herein.

In other embodiments, the activity of a HERK1, HERK2, THE, FER polypeptide may be reduced or eliminated by disrupting the gene encoding the HERK1, HERK2, THE, FER polypeptide. The invention encompasses mutagenized plants that carry T-DNA insertions or mutations in HERK1, HERK2, THE, FER genes, where the mutations reduce expression of the HERK1, HERK2, THE, FER gene or inhibit the nitrogen utilization activity of the encoded HERK1, HERK2, THE, FER polypeptide.

Thus, many methods may be used to reduce or eliminate the activity of a HERK1, HERK2, THE, FER polypeptide. In addition, more than one method may be used to reduce the activity of a single HERK1, HERK2, THE, FER polypeptide.

EXAMPLES

Example 1

Three Related Receptor-Like Kinases are Required for Optimal Cell Elongation in *Arabidopsis thaliana*

In this study, we found that three related receptor-like kinases (RLKs), HERCULES1, THESEUS1 and FERONIA, are transcriptionally induced by BRs and are down-regulated in the loss-of-function BR mutant bri1 and up-regulated in the constitutive BR-response mutant bes1-D. These RLKs belong to the CrRLK family that has 17 members in *Arabidopsis*. Although two of the RLKs were recently found to mediate male-female interaction during pollen tube reception (FERONIA) and to sense cell wall integrity THESEUS1), our genetic studies demonstrated that they are required for cell elongation during vegetative growth as herk1 the1 double and fer RNAi mutants displayed striking dwarf phenotypes. The herk1 the1 double mutant enhances the dwarf phenotype of bri1 and partially suppresses bes1-D phenotype, supporting a role of HERK1/THE1 in BR-mediated cell elongation. Microarray experiments demonstrated that these RLKs control the expression of a unique set of genes including those implicated in cell elongation and 16% of the genes affected in herk1 the1 are regulated by BRs. Our results, therefore, identify a previously unknown pathway that functions cooperatively with, but largely independent of the BR pathway to regulate cell elongation. The work establishes a platform to identify other signaling components in this important pathway for plant growth and provides a paradigm to study the coordination of independent pathways in the regulation of a common biological process.

In this study, we report on the characterization of three related genes, HERCULES1 Receptor Kinase 1 (HERK1, At3g46290), THESEUS1 (THE1, At5g54380) and FERONIA (FER, At3g51550), all of which are induced by BRs.

These three RLKs belong to CrRLK family that has 17 members in *Arabidopsis* (18, 19). During the course of characterizing these genes, THE1 and FER were reported by others to repress cell elongation in various systems (18). Loss-of-function mutations in THE1 were shown to suppress the hypocotyl elongation defect of a cellulose-deficient mutant cesA6 in dark-growing seedlings. Therefore, THE1 was proposed to be a sensor of cell wall integrity—inhibiting cell elongation when the cell wall is damaged (20). On the other hand, FER was found to be involved in male-female interaction during pollen tube reception in *Arabidopsis* (21). More specifically, FER, which is expressed in synergid cells of female gametophytes, was proposed to receive a signal from incoming pollen tubes and to inhibit pollen tube elongation, leading to eruption of the pollen tip and release of sperm cells to fertilize the egg cell (21, 22). In complete loss-of-function mutants of FER, feronia (fer) and sirene (sir), pollen tubes continued to grow without fertilizing the egg cell (21, 23, 24).

The broad expression patterns of FER, THE1, and HERK1, especially during vegetative growth (18), imply additional functions for these RLKs. Our genetic studies demonstrated that the HERK1/THE1/FER pathway is required for optimal cell elongation and interacts with the BR pathway. Microarray experiments indicated that most of the genes affected in the mutants are not BR target genes. We therefore conclude that HERK1/THE1/FER are components of a newly recognized pathway that functions cooperatively, but largely independent of the BR pathway to promote cell elongation.

Results

HERK1, THE1 and FER are Induced by BRs and Modulated in BR Mutants

In our effort to identify and characterize BR regulated genes, we found that HERK1, THE1 and FER are induced by BRs as revealed by both published (15) and publicly available microarray data summarized in FIG. 8A world wide web at bbc.botany.utoronto.ca/efp/cgi-bin/efpWeb.cgi). HERK1, THE1 and FER are the most highly induced genes by BL and, therefore, were chosen for further study. Our quantitative RT-PCR experiments confirmed that brassinolide (BL), the most active BR, up-regulated these RLKs by about 20-80% in seedlings and/or adult plants (FIG. 1A). The expression changes are significant as demonstrated by student's t-test (p<0.01). In addition, the expression levels of the RLK genes were reduced in the loss-of-function mutant bri1 and increased in the constitutive BR-response mutant bes1-D (FIG. 1B). The close relationship of these three RLKs in the phylogenetic tree, especially between HERK1 and THE1 (FIG. 5) as well as their induction by BRs suggest an involvement in BR-regulated processes.

We first determined the cellular localization of HERK1 by fluorescence microscopy. Similar to FER (21) and THE1 (20), the HERK1-GFP fusion localized to the plasma membrane when expressed in *Arabidopsis* protoplasts and plants (FIGS. 1C and E). The kinase activity of HERK1 was tested with recombinant proteins expressed and purified from *E. coli*. The wild-type kinase domain of HERK1 was autophosphorylated, while a mutant form, in which a conserved lysine was mutated to arginine (K513R), lost its kinase activity in vitro (FIG. 1F). Taken together, these results demonstrate that HERK1, like its homologs THE1 and FER, is a plasma membrane-localized receptor kinase.

HERK1, THE1 and FER are universally expressed in most vegetative tissues, including leaves, stems and roots as revealed by our promoter-GUS (-glucuronidase) reporter gene studies (FIG. 1G-I) and by studies carried out by others (20, 21). The expression is particularly strong in the regions undergoing cell elongation, such as in hypocotyls and leaf petioles. Combined with the fact that HERK1, THE1 and FER are regulated by BRs and modulated in BR mutants, we hypothesize that HERK1, THE1 and FER have a more general role in cell elongation processes, in addition to the function of THE1 in sensing cell wall integrity and FER in pollen tube and female gametophyte interactions.

HERK1, THE1 and FER are Required for Cell Elongation During Vegetative Growth

T-DNA insertion mutants were identified for both HERK1 and THE1, designated as herk1-1 and the1-4, which had the T-DNA insertions in the kinase domains in both genes. Both mutants are null since transcripts were not detected in mutant plants (FIG. 4C, and data not shown). The close homology and overlapping expression patterns of HERK1 and THE1 prompted us to test whether these two genes function redundantly. Toward that end, we constructed a herk1-1 the1-4 double mutant, referred to hereafter as herk1 the1. Because there are no T-DNA insertion mutants available for FER and also because the null allele offer was embryonic lethal due to failed fertilization, we used an artificial microRNA, or amiRNA (25) to knockdown the FER gene to determine its function during vegetative growth. An amiRNA specifically targeting FER was cloned into an expression vector driven by the strong, constitutive BRI1 gene promoter (26). More than 80% of the transgenic lines displayed a reduced growth phenotype (FIG. 2B). Two transgenic lines, designated as fer1 and fer2, with different degrees of FER reduction, were chosen for further studies.

We first determined the BR response of the mutants by measuring hypocotyl lengths in the absence or presence of BL, the most active BR. BRs stimulate cell elongation in the light-grown seedlings, and hypocotyl elongation has been widely used as a measure BR activity. herk1, the1 and herk1 the1 double mutants have somewhat shorter hypocotyls compared to wildtype without BL treatment, while fer1 and fer2 have shorter hypocotyls than wildtype with or without BL treatment (FIG. 2A). Interestingly, the BR response was largely unchanged in the mutants (FIG. 2A). We therefore concluded that HERK1, THE1 and particularly, FER, are required for hypocotyl elongation mostly in a BR-independent manner at the seedling stage.

At the adult stage, while herk1 and the1 single mutants are indistinguishable from wild type, herk1 the1 double mutants were clearly stunted in growth (FIG. 2B). The elongation of both leaves and leaf petioles was affected (FIGS. 2C-D). We focused on leaf petioles that were most severely affected in the mutants. While the elongation of petioles was slightly affected in herk1 and the1 single mutants, the petioles were reduced to half the length of the wildtype in herk1 the1 double mutants (FIGS. 2C-D). To determine the basis for the stunted growth phenotypes, we examined the cells in the leaf petioles. Most cells in the mutant leaf petioles were shorter than the corresponding cell types in wild type (FIG. 2E-F and data not shown).

To confirm that the mutant phenotype is caused by T-DNA knockout, a genomic clone of HERK1 under the control of its native promoter was transformed back into the herk1 the1 double mutant. From more than 10 transgenic lines recovered, about half of them showed clear rescue of the mutant phenotype (FIGS. 6A-C). The level of the HERK1 transcript was higher in the transgenic plants with rescued phenotype (FIG. 6D). We conclude that HERK1 and THE1 function redundantly to promote cell elongation, especially in adult plants.

Both fer1 and fer2 adult plants have almost the same phenotypes as the herk1 the1 double mutant, with a more severe cell elongation defect in fer1 (FIGS. 2B-D). The fertility in both lines was also reduced, presumably due to impaired FER function in pollen tube-female gametophyte interaction. The extent of both vegetative and reproductive phenotypes correlated well with the reduction in expression of the FER gene (FIGS. 2B-D, FIG. 4C and unpublished observation).

To determine the gain-of-function phenotype for the RLKs, we identified several transgenic plant lines overexpressing the HERK1 gene under its own promoter, aided by CAMV 35S enhancer elements. Of these, we characterized one representative line that accumulated about 10 times more HERK1 RNA than wild-type (FIG. 7). Overexpression of HERK1 appeared to increase petiole length by about 15-20% (FIG. 7A). Consistent with the phenotype, several HERK1/THE1 regulated genes (see next) were up-regulated by about 20-70% (FIG. 7B). Taken together, our results demonstrate that in addition to their established roles in sensing cell wall-integrity (20) and pollen and female gametophyte interaction (21), HERK1/THE1/FER RLKs play a major role in promoting cell elongation during vegetative growth.

Genetic Interactions Between BR and HERK Pathways

Triple mutants of bri1-5 herk1 the1 and bes1-D herk1 the1 were constructed to investigate the genetic interactions between BRI1 and HERK signaling (FIG. 3). bri1-5 is a weak loss-of-function allele of the BR receptor gene, BRI1, that displays a semi-dwarf phenotype (27). The herk1 the1 double mutant enhanced the bri1-5 dwarf phenotype (FIGS. 3A-C). On the other hand, bes1-D is a gain-of-function mutant that displays constitutive BR responses including excessive cell elongation (13). The herk1 the1 double mutant partially suppressed the cell elongation phenotype of bes1-D (FIGS. 3D-E). These genetic studies suggest that HERK1 and THE1 cooperate with the BR pathway and mediate part of BR-regulated cell elongation.

Most of the HERK1/THE1/FER Affected Genes are not Regulated by BRs

Despite similar defects in cell elongation, the herk1 the1 double or fer mutants differ from BR mutants. BR mutants have epinastic and dark green leaves that were not observed in herk1 the1 double or fer mutants (FIG. 2 and unpublished observation). We asked whether the cell elongation phenotype of herk1 the1 double mutant was due to changes in BR-regulated gene expression. To that end, the global gene expression patterns of herk1 the1 double mutant, in the absence and presence of BL during the adult stages, were first determined by microarray analysis (FIGS. 4A and B, Table 1 and Table S1-S4). In adult plants, while BL induces and represses the expression of 650 and 520 genes respectively, 269 and 505 genes were down- or up-regulated, respectively, in herk1 the1 double mutant compared to wild-type control. Using GeneSpring world wide web at (http://www.chem.agilent.com/enUS/Products/software/lifesciencesinformatics/genespringgx/Pages/default.aspx), we performed cluster analysis of BR- and HERK1/THE1-regulated genes and found that the majority of BR-regulated genes were not affected in the mutant, and likewise, the majority of HERK1/THE1 regulated genes were not clearly regulated by BL (FIGS. 4A and B). It appears that only about 10% of BR-regulated genes were affected in the herk1 the1 double mutant or 16% genes affected in herk1 the1 double mutant are regulated by BRs (FIG. 4B). These results suggest that the HERK pathway is largely independent of the BR pathway with a subset of overlapping genes.

Consistent with the similar phenotypes between fer1, fer2 and herk1 the1 double mutant, 12 out of 16 randomly chosen genes affected in herk1 the1 double mutant are similarly affected in fer1 and fer2 mutants (FIG. 4C). The gene expression changes correlate well with the mutant phenotypes, i.e. the genes are reduced or increased more in fer1 than in fer2 and herk1 the1 double mutant. The results support the conclusion that HERK1/THE1 and FER likely affect a similar set of genes and, therefore, function in a common pathway.

To gain a better understanding of how the BR and HERK/THE pathways function to regulate similar processes, we further examined genes implicated in cell elongation (Table 1). It is well established that BRs promote cell elongation by inducing the expression of the genes involved in cell wall-loosening enzymes, such as xyloglucan endotransglycosylase/hydrolase (XTH) and Pectin Lyase-like (PLL) as well as expansins (EXP) (28-30). Consistent with its major function in promoting cell elongation, BRs induce the expression of seven XTHs, two PLLs and seven EXPs in adult plants. Similarly, HERK1/THE1 is also required for the expression of six cell elongation genes, including one XTH, and five EXPs. Interestingly, two genes (EXP1 and EXP8) are induced by both pathways and are likely to be common targets. These results indicated that while BR and HERK induce different sets of genes for cell elongation, there are some common target genes that may integrate signals from both pathways. Because only two out of sixteen BR-induced genes implicated in cell elongation are reduced in herk1 the1 double mutant, it seems unlikely that the mutant phenotype is solely due to the changes in BR target gene expression.

Discussion

Based on our results, we propose a working model for the HERK1/THE1/FER pathway and its relationship with the BR pathway in the regulation of cell elongation (FIG. 4D). While BRs function through BRI1 and BIN2 to regulate the BES1/BZR1 family transcription factors and, therefore, modulate the expression of target genes including those required for cell elongation, HERK1, THE1 and FER function in an independent pathway to regulate different genes including those implicated in cell elongation. The regulation of common targets may represent crosstalk between these two pathways.

Our study, therefore, identified an important pathway required for plant growth. Plant cell elongation is regulated by environmental cues such as light and several plant hormones, including BRs, auxin and gibberellin (31, 32). Our qRT-PCR information and the public microarray data revealed that while BRs induce the expression of all three RLKs (FIG. 1 and FIG. 8), other hormones, including auxin, gibberellin, ethylene and cytokinin that are known to regulate cell elongation or division, modulate individual RLKs would wide web at bbc.botany.utoronto.ca/efp/cgi-bin/efp-Web.cgi). For example, our qRT-PCR analysis indicated that GA3 up-regulates the expression of HERK1, THE1, and FER while IAA appears to induce HERK1 (FIG. 8B). However, the herk1 the1 double mutant responds normally to gibberellin in hypocotyl elongation assays and to auxin in root elongation assays (FIGS. 8C & D), implying that HERK/THE1/FER RLKs are unlikely involved in gibberellin or auxin perception. It is more likely that different hormones can modulate the expression of HERK1/THE1/FER to regulate plant growth. By comparison to other hormone-regulated genes (33), we found that among 774 herk1 the1 affected genes, 61, 7, 41, and 37 genes are known to be regulated by auxin (789 genes), gibberellin (122 genes), ethylene (532 genes) and cytokinin (491 genes), respectively (our unpublished observation). The observation further supports the notion that HERK1/THE1 and FER represent another pathway required for optimal cell elongation. The dwarf mutant phenotypes of HERK1/THE1 and FER at adult stage should greatly facilitate the identification of other signaling components for this important family of RLKs.

What is the relationship of HERK1, THE1 and FER? The fact that fer1 and fer2 showed almost identical phenotypes and affected similar genes to the herk1 the1 double mutant suggests that HERK1/THE1 and FER function in the same pathway. For example, FER could serve as a co-receptor for HERK1/THE1 such that a knockdown of FER has the same effect as a knockout of both HERK1 and THE1. It's worth noting that several other members in the family, such as At2g39360, At5g24010, At1g30570, At5g38990/At5g39000 and At5g39020 are slightly induced by BL (FIG. 8A). They may function in other processes including cell elongation. It's possible that different combinations of members regulate growth in different tissues or organs at different developmental stages.

HERK1/THE1/FER signaling apparently interacts with the BR pathway. First, BRs induce the expression of HERK1, THE1 and FER through BRI1 and BES1 (FIGS. 1A-B). Second, herk1 the1 double mutants enhance bri1 and suppress bes1-D mutant phenotypes (FIG. 3). Third, the two pathways regulate a common set of 127 target genes, including those involved in cell elongation (FIG. 4, Table 1). It's possible that functional cooperation between effectors in each pathway (i.e., BES1 and its counterpart in the RLK pathway) accounts for the expression of the common target genes. Identification of downstream effector protein(s) in the HERK1/THE1/FER pathway can help test the hypothesis.

Our study provides significant new insight into the function of CrRLK family of RLKs. HERK1, THE1, and FER are members of the CrRLK family RLKs in *Arabidopsis*. Two members of the family, FER and THE, were found recently to inhibit cell elongation in two different contexts (18). In contrast, we observed that knockout of both the HERK1 and THE1 genes or the reduction of FER led to reduced cell elongation. Meanwhile, overexpression of HERK1 resulted in upregulation of some HERK target genes and slightly enhanced petiole elongations (FIG. 7). Therefore, our results suggest a role of the RLK family in promoting cell elongation. Several possibilities can explain the seemingly opposite functions. First, the pathways may have different outputs in different tissues/organs at different developmental stages. Second, like many signaling pathways, different signaling intensities can lead to opposite biological effects. For example, while exogenously applied BRs promote hypocotyl elongation in light-grown seedlings, they inhibit hypocotyl growth in the dark where cell elongation is already very active.

Finally, our results extend the role of FER from female: male interaction to vegetative growth. Interestingly, BRs, which are well established for their role in vegetative growth, function in reproduction as well. BRs are required for pollen tube growth, as demonstrated by the fact that BR mutants are defective in pollen tube elongation and have reduced fertility (17, 34). Since FER functions to block further pollen tube growth once the tube reaches synergid cells, it is apparent that while BRs and FER have similar functions in vegetative tissue, they have opposite roles in pollen tube growth. The identification of other signaling components is needed to fully understand the functional divergence of the HERK1/THE1/FER pathway.

In summary, this study has identified novel signaling components that regulate an important plant growth process, cell elongation. The established phenotypes and target genes will help identify the ligand(s) and other signaling components. In addition, the apparent interactions between BR and HERK pathways provide a paradigm for the way in which different signaling pathways contribute to the regulation of a similar process, a general theme for growth and development.

Materials and Methods:

Plant Materials and Growth Conditions:

*Arabidopsis thaliana* ecotype Col-0 was the wild type. Seeds were geminated and grown on ½ MS medium with 1% sucrose under 15 hr light/9 hr dark cycle at 22° C. Two-week-old seedlings were usually transferred to soil and grown in growth rooms under same conditions.

HERK1 Localization and Kinase Activity

A HERK1-GFP or BES1-GFP construct was introduced to protoplasts derived from 5-day-old seedlings grown in liquid culture by PEG-mediated transfection and culture for 16 hr (35). The BRI1::HERK1-GFP was also introduced into *Arabidopsis* plants by floral dip method (36). Transgenic plants were identified by screening T1 seeds in ½ MS containing 50 mg/L Kanamycin. Protoplasts or hypocotyls cells from 3-day-old transgenic lines (T2) grown in the dark were observed under an Olympus fluorescence microscope with a filter for GFP visualization. For the in vitro kinase assay, wild-type HERK1 kinase domain (WT), and a mutant version (K513R), were cloned into a MBP (Maltose Binding Protein) fusion vector and expressed in *E. coli*. Recombinant proteins were purified using amylase resin (New England Biolabs) and used in kinase assay in 50 mM Tris-HCl, 150 mM NaCl, 1 mM $MaCl_2$, 0.1 mM ATP, pH 7.5, plus 2 ul $^{32}$P-ATP (Perkin Emer, 3000 Ci/mmol), room temperature, for 0.5 hr. Autophosphorylation was detected following protein gel electrophoresis and phosphorimaging with a Typhoon 9400 (GE Healthcare). Protein was visualized by SYPRO RUBY protein gel stain (Invitrogen).

Transgenic Studies:

The promoters of HERK1 (−2114/−19 relative to the translational start site) and FER (−1193/−27) were amplified from BAC DNA, and THE1 (−2222/−43) was amplified from genomic DNA, and cloned to the pBI101 with the -glucuronidae (GUS) gene (Clontech). A 5.3 kb HERK1 genomic fragment was cloned into pMN20 that harbors 4 copies of CaMV 35S enhancer (37). The constructs were transfected into *Agrobacterium* strain GV3101, which were used to transform *Arabidopsis*. T2 or T3 transgenic plants were used to detect reporter gene expression by GUS assay (38) or phenotypic analysis.

Identification of T-DNA Knockout Mutants and Creation of Artificial microRNA (amiRNA) Mutants The T-DNA knockout seeds, herk1 (SALK_008043) and the1-4 (CS829966), were obtained from ABRC (http://www.arabidopsis.org/). Homozygous plants were identified by PCR genotyping with primers listed in Table S5. Double mutants were constructed by cross single homozygous mutants and F2 plants were genotyped for double homozygous plants. The amiRNA system was used to knockdown FER. A set of four primers (Table S5) were designed using the tools found at http://wmd.weigelworld.org/cgi-bin/mirnatools.pl and used to amplify an amiRNA fragment (25), which was cloned into a binary vector under the control of BRI1 promoter.

Characterization of Growth Phenotype

For BR response experiments, brassinolide (BL, from Wako Chemicals USA Inc, Richmond Va.) was added to the medium after autoclaving and cooling to 50° C. The seeds were treated at 4° C. for 4 days and germinated and grown for 10 days before measuring hypocotyl lengths. For adult phenotypes, wild-type and mutant plants were grown side-by-side in a growth flat. The 24-day-old mature plants were examined for the growth phenotype and photographed. The petiole lengths of the sixth leaves, from 10 independent plants, were measured. The average and standard deviations were calculated. To examine the cell lengths, leaf petioles were fixed with 2% glutaraldehyde (w/v) and 2% paraformaldehyde (w/v) in 0.1M cacodylate buffer (pH 7.2) for 48 hours at 4° C. Samples were rinsed in 0.1M cacodylate buffer and dehydrated in a graded ethanol series, infiltrated and embedded using LR White resin (Electron Microscopy Sciences, Ft. Washington, Pa.). Resin blocks were polymerized for 48 hours at 60° C. Thick sections were made using a Reichert UC6 ultramicrotome (Leeds Precision Instruments, Minneapolis, Minn.). Sections were stained with 1% toluidine blue in 1% borax and images were taken using a Zeiss Axioplan II compound microscope with a MRC digital camera and Axiovision software (Carl Zeiss Inc., Thornwood, N.Y.).

Gene Expression Studies:

Microarray experiments were performed with 24-day-old adult plants. The whole plants were sprayed with either water or 1 M BL and incubate for 2.5 hours. The plants were pooled into three groups as triplicates (8 plants per group). Total RNA was prepared with RNeasy Plant Mini Kit (QIAGEN) and used to make probes for microarray experiments with Affymetrix *Arabidopsis* Genomic arrays. The probe labeling, hybridization, and scanning were performed according to manufacture's instructions. Microarray data was normalized by the MAS 5.0 method implemented in the R package affy and the linear model was applied to two sample comparison (samples with and without BL treatment or WT compared to mutant) using the limma package (39, 40). Genes with an adjusted p-value $\leq$0.01 were considered to be differentially expressed. The BR-induced genes, HERK1/THE regulated genes were used for clustering analysis with the GENESPRING program (Silicon Genetics) using Pearson Correlation.

For reverse transcription-polymerase chain reaction (RT-PCR), 2 μg total RNA was reverse-transcribed to cDNA by SuperScript II Reverse Transcriptase (Invitrogen). For real-time quantitative RT-PCR, the primers were designed so that the products are between 200-300 bps. The SYBR Green PCR Master mix (Applied Biosystems) was used and the PCR reactions were run on the Mx4000® multiplex quantitative PCR system (Stratagene). Two or three biological replicates were each analyzed with 2-3 RT-PCR reactions. For semi-quantitative RT-PCR, the same amount of cDNA was used for each PCR reaction. The primers used are listed in Table S5, and the UBQ5 gene was the control. PCR reactions were stopped in the linear range of the amplification and were repeated for 2 times. Very similar results were obtained with both sets of samples.

REFERENCES

1. Chory J, Wu D (2001) Weaving the complex web of signal transduction. *Plant Physiol* 125: 77-80.
2. Muller B, Sheen J (2008) Cytokinin and auxin interaction in root stem-cell specification during early embryogenesis. *Nature* 453: 1094-1097.
3. Hardtke C S (2007) Transcriptional auxin-brassinosteroid crosstalk: who's talking?*Bioessays* 29: 1115-1123.
4. Li J, Jin H (2007) Regulation of brassinosteroid signaling. *Trends Plant Sci* 12: 37-41.
5. Gendron J M, Wang Z Y (2007) Multiple mechanisms modulate brassinosteroid signaling. *Curr Opin Plant Biol* 10: 436-441.
6. Belkhadir Y, Chory J (2006) Brassinosteroid signaling: a paradigm for steroid hormone signaling from the cell surface. *Science* 314: 1410-1411.
7. Clouse S, Sasse J (1998) Brassinosteroids: Essential regulators of plant growth and development. *Annu. Rev. Plant Physiol. Plant Mol. Biol.* 49: 427-451.
8. Wang X, Kota U, He K, Blackburn K, Li J, Goshe M B, Huber S C, Clouse S D (2008) Sequential transphosphorylation of the BRI1/BAK1 receptor kinase complex impacts early events in brassinosteroid signaling. *Dev Cell* 15: 220-235.
9. Tang W, Kim T W, Oses-Prieto J A, Sun Y, Deng Z, Zhu S, Wang R, Burlingame A L, Wang Z Y (2008) BSKs mediate signal transduction from the receptor kinase BRI1 in *Arabidopsis*. *Science* 321: 557-560.
10. Wang X, Chory J (2006) Brassinosteroids regulate dissociation of BKI1, a negative regulator of BRI1 signaling, from the plasma membrane. *Science* 313: 1118-1122.
11. Yin Y, Vafeados D, Tao Y, Yokoda T, Asami T, Chory J (2005) A new class of transcription factors mediate brassinosteroid-regulated gene expression in *Arabidopsis*. *Cell* 120: 249-259.
12. He J X, Gendron J M, Sun Y, Gampala S S, Gendron N, Sun C Q, Wang Z Y (2005) BZR1 is a transcriptional repressor with dual roles in brassinosteroid homeostasis and growth responses. *Science* 307: 1634-1638.
13. Yin Y, Wang Z Y, Mora-Garcia S, Li J, Yoshida S, Asami T, Chory J (2002) BES1 accumulates in the nucleus in response to brassinosteroids to regulate gene expression and promote stem elongation. *Cell* 109: 181-191.
14. Wang Z Y, Nakano T, Gendron J, He J, Chen M, Vafeados D, Yang Y, Fujioka S, Yoshida S, Asami T, Chory J (2002) Nuclear-localized BZR1 mediates brassinosteroid-induced growth and feedback suppression of brassinosteroid biosynthesis. *Dev Cell* 2: 505-513.
15. Nemhauser J L, Mockler T C, Chory J (2004) Interdependency of brassinosteroid and auxin signaling in *Arabidopsis*. *PLoS Biol* 2: E258.
16. Goda H, Sawa S, Asami T, Fujioka S, Shimada Y, Yoshida S (2004) Comprehensive comparison of auxin-regulated and brassinosteroid regulated genes in *Arabidopsis*. *Plant Physiol* 134: 1555-1573.
17. Clouse S D (1996) Molecular genetic studies confirm the role of brassinosteroids in plant growth and development. *Plant J* 10:1-8.
18. Hematy K, Hofte H (2008) Novel receptor kinases involved in growth regulation. *Curr Opin Plant Biol* 11: 321-328.
19. Shiu S H, Bleecker A B (2003) Expansion of the receptor-like kinase/Pelle gene family and receptor-like proteins in *Arabidopsis*. *Plant Physiol* 132: 530-543.
20. Hematy K, Sado P E, Van Tuinen A, Rochange S, Desnos T, Balzergue S, Pelletier S, Renou J P, Hofte H (2007) A receptor-like kinase mediates the response of *Arabidopsis* cells to the inhibition of cellulose synthesis. *Curr Biol* 17: 922-931.
21. Escobar-Restrepo J M, Huck N, Kessler S, Gagliardini V, Gheyselinck J, Yang W C, Grossniklaus U (2007) The FERONIA receptor-like kinase mediates male-female interactions during pollen tube reception. *Science* 317: 656-660.
22. McCormick S (2007) Plant science. Reproductive dialog. *Science* 317: 606-607.
23. Rotman N, Rozier F, Boavida L, Dumas C, Berger F, Faure J E (2003) Female control of male gamete delivery during fertilization in *Arabidopsis thaliana*. *Curr Biol* 13: 432-436.
24. Huck N, Moore J M, Federer M, Grossniklaus U (2003) The *Arabidopsis* mutant feronia disrupts the female gametophytic control of pollen tube reception. *Development* 130: 2149-2159.
25. Schwab R, Ossowski S, Riester M, Warthmann N, Weigel D (2006) Highly specific gene silencing by artificial microRNAs in *Arabidopsis*. *Plant Cell* 18: 1121-1133.
26. Li J, Chory J (1997) A putative leucine-rich repeat receptor kinase involved in brassinosteroid signal transduction. *Cell* 90: 929-938.
27. Noguchi T, Fujioka S, Choe S, Takatsuto S, Yoshida S, Yuan H, Feldmann K A, Tax F E (1999) Brassinosteroid-insensitive dwarf mutants of *Arabidopsis* accumulate brassinosteroids. *Plant Physiol* 121: 743-752.
28. Palusa S G, Golovkin M, Shin S B, Richardson D N, Reddy A S (2007) Organ-specific, developmental, hormonal and stress regulation of expression of putative pectate lyase genes in *Arabidopsis*. *New Phytol* 174: 537-550.
29. Becnel J, Natarajan M, Kipp A, Braam J (2006) Developmental expression patterns of *Arabidopsis* XTH genes reported by transgenes and Genevestigator. *Plant Mol Biol* 61: 451-467.
30. Darley C P, Forrester A M, McQueen-Mason S J (2001) The molecular basis of plant cell wall extension. *Plant Mol Biol* 47: 179-195.
31. Chory J, Chatterjee M, Cook R K, Elich T, Fankhauser C, Li J, Nagpal P, Neff M, Pepper A, Poole D, Reed J, Vitart V (1996) From seed germination to flowering, light controls plant development via the pigment phytochrome. *Proc Natl Acad Sci USA* 93: 12066-12071.
32. De Grauwe L, Vandenbussche F, Tietz O, Palme K, Van Der Straeten D (2005) Auxin, ethylene and brassinosteroids: tripartite control of growth in the *Arabidopsis* hypocotyl. *Plant Cell Physiol* 46: 827-836.
33. Nemhauser J L, Hong F, Chory J (2006) Different plant hormones regulate similar processes through largely non-overlapping transcriptional responses. *Cell* 126: 467-475.
34. Szekeres M, Nemeth K, Koncz-Kalman Z, Mathur J, Kauschmann A, Altmann T, Rédei G P, Nagy F, Schell J, Koncz C (1996) Brassinosteroids rescue the deficiency of CYP90, a cytochrome P450, controlling cell elongation and de-etiolation in *Arabidopsis*. *Cell* 85: 171-182.
35. Yoo S D, Cho Y H, Sheen J (2007) *Arabidopsis* mesophyll protoplasts: a versatile cell system for transient gene expression analysis. *Nat Protoc* 2: 1565-1572.
36. Clough S J, Bent A F (1998) Floral dip: a simplified method for *Agrobacterium*-mediated transformation of *Arabidopsis thaliana*. *Plant J* 16: 735-743.

37. Weigel D, Ahn J H, Blazquez M A, Borevitz J O, Christensen S K, Fankhauser C, Ferrandiz C, Kardailsky I, Malancharuvil E J, Neff M M, Nguyen J T, Sato S, Wang Z Y, Xia Y, Dixon R A, Harrison M J, Lamb C J, Yanofsky M F, Chory J (2000) Activation tagging in Arabidopsis. *Plant Physiol* 122: 1003-1013.
38. Jefferson R A, Kavanagh T A, Bevan M W (1987) GUS fusions: beta-glucuronidase as a sensitive and versatile gene fusion marker in higher plants. *EMBO J* 6: 3901-3907.
39. Smyth G K, Michaud J, Scott H S (2005) Use of within-array replicate spots for assessing differential expression in microarray experiments. *Bioinformatics* 21: 2067-2075.
40. Gautier L, Cope L, Bolstad B M, Irizarry R A (2004) affy—analysis of Affymetrix GeneChip data at the probe level. *Bioinformatics* 20: 307-315.

designated as HERCULES2 (HERK2), functions redundantly with HERK1 and THE1 to promote stem elongation Our results, together with those from others, provide compelling evidence that the CrRLK1L family members play important role in plant growth.

HERK1 (At3g46290), THE1 (At5g54380) and FER (At3g51550) belong to the CrRLK1L (named after the founding member identified in *Catharanthus roseus*) family RLKs that has 17 members in Arabidopsis[1, 2]. Several elegant work demonstrated that FER and THE1 function to repress cellular growth in several processes[3]. FER is involved in male-female interaction during fertilization[4, 5]. In wild-type plants, FER is localized in the plasma membrane of synergid cells and was proposed to perceive an unknown signal from the incoming pollen tube and to inhibit its further growth. In loss-of-function mutants of FER gene, pollen tubes overgrow and thus cannot fertilize the egg cells,

TABLE 1

The regulation of genes implicated in cell elongation by BRs and HERK1/THE1

| | Gene No. | WT-BL | WT + BL | herk1 the1-BL | herk1 the1 + BL | Annotation |
|---|---|---|---|---|---|---|
| BL | AT5G57560 | 2277 | 7344 | 2728 | 7941 | XTH22 |
| | AT1G10550 | 47 | 223 | 48 | 191 | XTH33 |
| | AT1G11545 | 453 | 1178 | 357 | 1249 | XTH8 |
| | At2g06850 | 7247 | 13455 | 5096 | 11194 | XTH4 |
| | At4g30290 | 153 | 297 | 162 | 259 | XTH19 |
| | At1g65310 | 137 | 214 | 95 | 302 | XTH17 |
| | At3g23730 | 559 | 819 | 636 | 1069 | XTH16 |
| | At3g07010 | 427 | 939 | 325 | 829 | PLL20 |
| | At1g04680 | 2466 | 3402 | 1982 | 2932 | PLL26 |
| | At4g38400 | 188 | 433 | 151 | 381 | EXPL2 |
| | At3g45970 | 581 | 1339 | 529 | 970 | EXPL1 |
| | At2g37640 | 384 | 641 | 340 | 594 | EXP3 |
| | At3g45960 | 24 | 92 | 18 | 44 | EXPL3 |
| | At1g20190 | 141 | 395 | 35 | 225 | EXP11 |
| BL/herk1 | At2g40610 | 1006 | 2407 | 437 | 1586 | EXP8 |
| the1 | At1g69530 | 6798 | 8465 | 3595 | 6462 | EXP1 |
| herk1 the1 | At2g20750 | 295 | 198 | 161 | 157 | EXPB1 |
| | At2g28950 | 3287 | 2524 | 2074 | 1919 | EXP6 |
| | At3g29030 | 2323 | 2112 | 1523 | 1848 | EXP5 |
| | At4g37800 | 2899 | 3419 | 1831 | 2864 | XTH7 |

Table Legends
Table 1: Affymetrix *Arabidopsis* Genomic Arrays were used to detect gene expression. BL-regulated or herk1 the1-affected genes implicated in cell elongation are included. Average of the gene expression level from three biological replicates are shown. Note that several BL-induced genes appeared to be reduced in herk1 the1 double mutant, but did not pass the statistical test.

Example 2

A Family of Receptor-Like Kinases are Regulated by BES1 and Involved in Plant Growth in *Arabidopsis thaliana*

Plant growth is dictated by both developmental and environmental cues, many of which are perceived by receptor-like kinases (RLKs). In *Arabidopsis*, there are more than 600 RLKs; but the functions of most of them are unknown. We recently found that several members of CrRLK1L family RLKs are regulated by plant steroid hormone Brassinosteroids (BRs). Two of the RLKs, FERONIA (FER) and THESEUS1 (THE1) have been previously found to inhibit cell elongation during pollen tube/synergid cell recognition and in sensing cell wall integrity after damage, respectively. However, we found that HERCULES1 (HERK1), another member in the family, as well as THE1 and FER, are regulated by BRs and required for cell elongation during vegetative growth. Here we provide additional evidence for the regulation of the family members by BR effector protein BES1. We also show that another member in the family, resulting in infertility and embryonic lethality[5-7]. THE1 was identified in a suppressor screen for cellulose-deficient mutant cesA6. Loss-of-function mutations in THE1 suppressed the dwarf phenotype of cesA6 and several other cell wall mutants; THE1 was therefore proposed to inhibit cell elongation when cell wall is damaged[8]. In contrast to the reported inhibitory effects on cellular growth in different contexts, we recently found that HERK1, THE1 and FER are actually required for optimal cell elongation during vegetative growth[9].

BRs function to regulate cell elongation and many other processes[10-13]. BRs signal through a membrane-localized receptor kinase BRI1 and other signaling components[10, 14-16] to control BES1 and BZR1 family transcription factors, which mediate the expression of many genes for BR responses[17-20]. In an effort to identify and characterize BR target genes, we found that three CrRLK1L family members, HERK1, THE1 and FER, are induced by BRs[9]. In addition, the herk1 the1 double and fer single mutants displayed a similar stunted growth phenotype due to defect in cell elongation. Public microarray data revealed that several other members in the family are also induced by Brassinolide (BL), the most active BR (world wide web at bbc.botany.utoronto.ca/efp/cgi-bin/efpWeb.cgi). To further confirm that these RLK genes are modulated by BRs and/or BES1, we performed a microarray experiment with bes-D mutant[19], a constitutive BR response mutant due to highly accumulated BES1 protein, with En-2 as wild-type control (L.L. & Y.Y. in preparation). The expression of all CrRLK1L members is examined (FIG. 5A). At least 6 of the family members, including FER, THE1, HERK1, At1g30570 (HERK2, see next), At2g39360, and At5g24010, are slightly upregulated by BL treatment in the wild-type and are more clearly increased in bes1-D mutant, especially in the presence of BL. The results suggest that at least these 6 genes in the CrRLK1L family are modulated by BR pathway through BES1.

To test whether other BR-regulated members are also involved in plant growth, we obtained a T-DNA knockout line for HERK2 from ABRC (SALK_105055, herk2), constructed herk1 herk2 the1 triple mutant and examined their growth phenotypes (FIG. 1B-D). At the young seedling stage, while either herk2 or herk1 the1 has only slightly reduced growth, herk1 herk2 the1 triple mutant has clearly reduced hypocotyl elongation (FIG. 9B). Similarly, herk1 herk2 the1 adult plants also have reduced petiole lengths compared to herk1 the1 double mutant (FIG. 9C-D). Taken together, we conclude that HERK2 functions redundantly with HERK1 and THE1 to promote stem (hypocotyl and leaf petiole) elongation. Although herk1 heck 2 the1 triple mutant has similar hypocotyl lengths compared to fer mutant at seedling stage, its adult has less stunted growth phenotype than strong fer mutant[9]. It's possible that other family members, such as At2g39360 and At5g24010, function somewhat redundantly with HERK1, HERK2 and THE1 in promoting plant growth. Further construction of multiple mutant should address the possibility.

Similar to herk1 the1 double mutant, herk1 herk2 the1 appears to respond to BL normally (FIG. 9B), which support our previous conclusion that HERK family RLKs define a signaling pathway that cooperates with, but is largely independent of the BR pathway in controlling plant growth. Since these RLKs are also modulated by many other plant hormones and environmental conditions world wide web bbc.botany.utoronto.ca/efp/cgi-bin/efpWeb.cgi), it's possible that these RLKs function to integrate multiple signals to regulate plant growth and other responses.

In summary, BRs function through BES1 to regulate the expression of HERK1, HERK2, THE1 and FER genes. Since knockdown of FER displays very strong growth phenotype[9], which is similar to herk1 herk2 the1 triple mutant (FIG. 9C), FER may function as a heterodimer partner for other RLKs. HERK1/HERK2/THE1/FER may perceive unidentified ligand(s) and signal through intermediate components to regulate genes for plant growth and other responses (FIG. 9E). With all the available mutants, it is now feasible to further investigate the functions of this family of RLKs, to identify their ligand(s) and additional components in the signal transduction pathway.

REFERENCES

1. Shiu S H, Bleecker A B. Expansion of the receptor-like kinase/Pelle gene family and receptor-like proteins in *Arabidopsis*. Plant Physiol 2003; 132:530-43.
2. Schulze-Muth P, Irmler S, Schroder G, Schroder J. Novel type of receptor-like protein kinase from a higher plant (*Catharanthus roseus*). cDNA, gene, intramolecular autophosphorylation, and identification of a threonine important for auto- and substrate phosphorylation. J Biol Chem 1996; 271:26684-9.
3. Hematy K, Hofte H. Novel receptor kinases involved in growth regulation. Curr Opin Plant Biol 2008; 11:321-8.
4. McCormick S. Plant science. Reproductive dialog. Science 2007; 317:606-7.
5. Escobar-Restrepo J M, Huck N, Kessler S, Gagliardini V, Gheyselinck J, Yang W C, et al. The FERONIA receptor-like kinase mediates male-female interactions during pollen tube reception. Science 2007; 317:656-60.
6. Rotman N, Rozier F, Boavida L, Dumas C, Berger F, Faure J E. Female control of male gamete delivery during fertilization in *Arabidopsis thaliana*. Curr Biol 2003; 13:432-6.
7. Huck N, Moore J M, Federer M, Grossniklaus U. The *Arabidopsis* mutant feronia disrupts the female gametophytic control of pollen tube reception. Development 2003; 130:2149-59.
8. Hematy K, Sado P E, Van Tuinen A, Rochange S, Desnos T, Balzergue S, et al. A receptor-like kinase mediates the response of *Arabidopsis* cells to the inhibition of cellulose synthesis. Curr Biol 2007; 17:922-31.
9. Guo H, Li L, Ye H, Yu X, Algreen A, Yin Y. Three related receptor-like kinases are required for optimal cell elongation in *Arabidopsis thaliana*. Proc Natl Acad Sci USA 2009; 106:7648-53.
10. Li J, Jin H. Regulation of brassinosteroid signaling. Trends Plant Sci 2007; 12:37-41.
11. Gendron J M, Wang Z Y. Multiple mechanisms modulate brassinosteroid signaling. Curr Opin Plant Biol 2007; 10:436-41.
12. Belkhadir Y, Chory J. Brassinosteroid signaling: a paradigm for steroid hormone signaling from the cell surface. Science 2006; 314:1410-1.
13. Clouse S, Sasse J. Brassinosteroids: Essential regulators of plant growth and development. Annu Rev Plant Physiol Plant Mol Biol 1998; 49:427-51.
14. Wang X, Kota U, He K, Blackburn K, Li J, Goshe M B, et al. Sequential transphosphorylation of the BRI1/BAK1 receptor kinase complex impacts early events in brassinosteroid signaling. Dev Cell 2008; 15:220-35.
15. Tang W, Kim T W, Oses-Prieto J A, Sun Y, Deng Z, Zhu S, et al. BSKs mediate signal transduction from the receptor kinase BRI1 in *Arabidopsis*. Science 2008; 321: 557-60.
16. Wang X, Chory J. Brassinosteroids regulate dissociation of BKI1, a negative regulator of BRI1 signaling, from the plasma membrane. Science 2006; 313:1118-22.
17. Yin Y, Vafeados D, Tao Y, Yokoda T, Asami T, Chory J. A new class of transcription factors mediate brassinosteroid-regulated gene expression in *Arabidopsis*. Cell 2005; 120:249-59.
18. He J X, Gendron J M, Sun Y, Gampala S S, Gendron N, Sun C Q, et al. BZR1 is a transcriptional repressor with dual roles in brassinosteroid homeostasis and growth responses. Science 2005; 307:1634-8.
19. Yin Y, Wang Z Y, Mora-Garcia S, Li J, Yoshida S, Asami T, et al. BEST accumulates in the nucleus in response to brassinosteroids to regulate gene expression and promote stem elongation. Cell 2002; 109:181-91.
20. Wang Z Y, Nakano T, Gendron J, He J, Chen M, Vafeados D, et al. Nuclear-localized BZR1 mediates brassinosteroid-induced growth and feedback suppression of brassinosteroid biosynthesis. Dev Cell 2002; 2:505-13.

Example 3

HERK1, THE1 and FER are Implicated in Plant Defense Response Against Bacterial Infection Our gene expression studies on herk1 the1 mutant suggest that HERK1, THE1 and FER are potentially involved in plant defense responses. To test the hypothesis, we infiltrated wild-type, herk1 the1, herk1 herk2 the1 and fer mutant plants with bacterium *Pseudomonas syringae*. The bacterial accumulations in plants were determined two days after inoculation. As shown in FIG. 1, all the mutants accumulated more bacteria than the wild-type control. The result suggests that HERK1, HERK2, THE1 and FER are normally required for plant defense against bacterial infection.

We then determined the expression of Pathogen-Related genes, PR1 and PR5, in herk1 the1 mutant. PR1 and PR5 are induced in wild-type after bacterial infection, but the inductions of both genes are compromised in herk1 the1 double mutant (FIG. 2). Taken together, our results demonstrated that HERK1, HERK2, THE1 and FER1 control pathogen-related gene expression after bacterial infection and therefore regulate plant defense against bacteria.

FIG. 10. The herk1 the1, herk1 herk2 the1 and fer Mutants Accumulate More Bacteria of *Pseudomonas syringae*.

Same amount of bacteria were infiltrated to one-month-old wild-type (WT) and mutant plant leaves. Two-day after the inoculation, same amount of leaf tissues were ground in water and diluted 10, 100 and 1000 times (indicated as −1, −2, and −3). The bacterial amounts were determined by spotting 100 ul of each of the dilutions onto bacterial plates. The bacterial plates were grown at 30 C for two days. The results were confirmed by quantifications, which indicate that the mutants usually accumulate 5-10 times more bacteria than the WT.

FIG. 11. Pathogen-Related (PR) Gene Expression is Compromised in herk1 the1 Mutant.

WT and herk1 the1 plants were infiltrated with *Pseudomonas syringae*. RNA were prepared from infected plants after indicated times. Northern blotting was performed with PR1 and PR5 genes (A). The loading of RNA was indicated by ribosomal RNA (rRNA). The expression of PR1 (B) and PR5 (C) in WT and herk1 the1 were quantified and plotted.

Example 4

```
Arabidopsis thaliana FER (FERONIA); kinase/ protein kinase (FER) mRNA,
complete cds
LOCUS       NM_115014    3123 bp    mRNA    linear    PLN 21-AUG-2009
DEFINITION  Arabidopsis thaliana FER (FERONIA); kinase/ protein kinase (FER)
            mRNA, complete cds.
ACCESSION   NM_115014
VERSION     NM_115014.4  GI:186510924
KEYWORDS    .
SOURCE      Arabidopsis thaliana (thale cress)
  ORGANISM  Arabidopsis thaliana
            Eukaryota; Viridiplantae; Streptophyta; Embryophyta; Tracheophyta;
            Spermatophyta; Magnoliophyta; eudicotyledons; core eudicotyledons;
            rosids; eurosids II; Brassicales; Brassicaceae; Arabidopsis.
COMMENT     REVIEWED REFSEQ: This record has been curated by TAIR. The
            reference sequence was derived from AT3G51550.1.
            On Apr 24, 2008 this sequence version replaced gi:145339368.
FEATURES             Location/Qualifiers
     source          1..3123
                     /organism="Arabidopsis thaliana"
                     /mol_type="mRNA"
                     /db_xref="taxon:3702"
                     /chromosome="3"
                     /ecotype="Columbia"
     gene            1..3123
                     /gene="FER"
                     /locus_tag="AT3G51550"
                     /gene_synonym="FERONIA"
                     /function="Encodes a synergid-expressed, plasma-membrane
                     localized receptor-like kinase that accumulates
                     asymmetrically in the synergid membrnane at the filiform
                     apparatus and mediates male-female gametophyte
                     interactions during pollen tube reception."
                     /db_xref="GeneID:824318"
                     /db_xref="TAIR:AT3G51550"
     CDS             143..2830
                     /gene="FER"
                     /locus_tag="AT3G51550"
                     /gene_synonym="FERONIA"
                     /note="FERONIA (FER); FUNCTIONS IN: protein kinase
                     activity, kinase activity; INVOLVED IN: pollen tube
                     reception, protein amino acid autophosphorylation; LOCATED
                     IN: filiform apparatus, plasma membrane, membrane;
                     EXPRESSED IN: 28 plant structures; EXPRESSED DURING: 13
                     growth stages; CONTAINS InterPro DOMAIN/s: Protein kinase,
                     ATP binding site (InterPro:IPR017441), Protein kinase,
                     core (InterPro:IPR000719), Serine/threonine protein
                     kinase-related (InterPro:IPR017442), Protein kinase-like
                     (InterPro:IPR011009), Serine/threonine protein kinase,
                     active site (InterPro:IPR008271); BEST Arabidopsis
                     thaliana protein match is: protein kinase family protein
```

-continued (TAIR:AT3G04690.1); Has 81933 Blast hits to 81006 proteins
in 3073 species: Archae - 46; Bacteria - 7093; Metazoa -
36361; Fungi - 6132; Plants - 18396; Viruses - 372; Other
Eukaryotes - 13533 (source: NCBI BLink)."
/codon_start=1
/product="FER (FERONIA); kinase/ protein kinase"
/protein_id="NP_190723.1"
/db_xref="GI:15230520"
/db_xref="GeneID:824318"
/db_xref="TAIR:AT3G51550"
/translation=

SEQ ID NO: 2
"MKITEGRFRLSLLLLLLISAATLISAADYSPTEKILLNCGGGA

SNLTDTDNRIWISDVKSKFLSSSSEDSKTSPALTQDPSVPEVPYMTARVFRSPFTYTF

PVASGRKFVRLYFYPNSYDGLNATNSLFSVSFGPYTLLKNFSASQTAEALTYAFIIKE

FVVNVEGGTLNMTFTPESAPSNAYAFVNGIEVTSMPDMYSSTDGTLTMVGSSGSVTID

NSTALENVYRLNVGGNDISPSADTGLYRSWYDDQPYIFGAGLGIPETADPNMTIKYPT

GTPTYVAPVDVYSTARSMGPTAQINLNYNLTWIFSIDSGFTYLVRLHFCEVSSNITKI

NQRVFTIYLNNQTAEPEADVIAWTSSNGVPFHKDYVVNPPEGNGQQDLWLALHPNPVN

KPEYYDSLLNGVEIFKMNTSDGNLAGTNPIPGPQVTADPSKVLRPTTRKSKSNTAIIA

GAASGAVVLALIIGFCVFGAYRRRKRGDYQPASDATSGWLPLSLYGNSHSAGSAKTNT

TGSYASSLPSNLCRHFSFAEIKAATKNFDESRVLGVGGFGKVYRGEIDGGTTKVAIKR

GNPMSEQGVHEFQTEIEMLSKLRHRHLVSLIGYCEENCEMILVYDYMAHGTMREHLYK

TQNPSLPWKQRLEICIGAARGLHYLHTGAKHTIIHRDVKTTNILLDEKWVAKVSDFGL

SKTGPTLDHTHVSTVVKGSFGYLDPEYFRRQQLTEKSDVYSFGVVLFEALCARPALNP

TLAKEQVSLAEWAPYCYKKGMLDQIVDPYLKGKITPECFKKFAETAMKCVLDQGIERP

SMGDVLWNLEFALQLQESAEEENGKGVCGDMDMDEIKYDDGNCKGKNDKSSDVYEGNVT

DSRSSGIDMSIGGRSLASEDSDGLTPSAVFSQIMNPKGR"

ORIGIN
SEQ ID NO: 1
```
   1 actcattaat tgattttctc tctctctccc ccaaaatatc tctgtcttct ccaaaaactc
  61 tctccgattt catcgcttag ggtttcttcc ccgattcttc agatctgaga agaagatctt
 121 cccggagaag tgctcttgat cgatgaagat cacagaggga cgattccgtc tctctcttct
 181 tcttcttctt cttctcatat ctgcagcaac tttaatctca gctgctgatt actctccaac
 241 agagaaaatc ctattgaatt gcggtggtgg tgcttctaat ctaaccgaca cagataaccg
 301 tatatggatc tccgatgtca aatcaaaatt cttatcatct tcctctgaag actctaaaac
 361 atcaccagcg ttaacacaag atccttccgt tcccgaagtt ccttacatga cggcgagagt
 421 tttccgatct cctttcactt acactttccc tgtagcatca ggtcgtaaat tgtgcgtct
 481 ctacttctac ccaaactcgt acgacggtct caacgctacc aactcgttat tctccgtctc
 541 ctttggtcct tacactcttc tcaagaattt cagtgcttct cagacggcgg aggcgttgac
 601 ttacgctttc atcatcaagg agtttgttgt caacgttgaa ggtggaacgt tgaacatgac
 661 gtttacaccg gaatcagctc cgtctaatgc gtatgcgttt gttaatggga ttgaggttac
 721 ttcaatgcct gatatgtata gtagtactga tgggactttg actatggttg gatcatctgg
 781 ctctgttact attgataaca gtactgctct tgagaatgtg tataggctca atgttggagg
 841 gaatgatatc tcgccttccg cggatacggg tttgtatagg tcgtggtatg atgatcagcc
 901 ttatatattt ggtgcaggac ttggtattcc agagactgct gatcccaaca tgacgattaa
 961 gtatcctacg gggactccta cttatgttgc tcctgtggat gtttattcaa ccgcgaggtc
1021 tatgggtcca acagctcaga tcaatctcaa ctacaatctt acttggattt tcagcattga
```

-continued

```
1081 ctctggtttc acttaccttg ttagacttca tttctgtgag gtttcttcga atatcactaa 1141 gatcaaccaa cgggtgttta caatctacct caacaatcaa actgctgagc ctgaagctga 1201 tgtgattgct tggactagtt caaacggggt tccgtttcac aaggattacg tggtgaatcc 1261 tccagaggga aatggacagc aagatttgtg gcttgctctt catcctaacc cagttaacaa 1321 gccggagtat tatgattctc ttcttaatgg agtggagata ttcaagatga atacttctga 1381 tggtaatctg gctggtacca atcctatacc tggtccacag gtgactgctg atccatctaa 1441 agtcctacgc ccgactacta ggaaatcgaa aagcaatacg gctattattg caggcgcagc 1501 cagtggtgca gttgttctgg cccttatcat tgggttttgt gtgtttggtg cttaccgcag 1561 acgtaagcgt ggtgattacc agcctgctag tgatgcaaca tcagggtggc ttccactatc 1621 tctgtatgga aactcacatt ctgctggctc ggcgaagaca aacacaacag gaagttatgc 1681 ctcgtccctt ccgtcaaatc tttgccgtca cttctcgttt gctgagatca aagctgccac 1741 taaaaacttt gatgagtccc gggtgcttgg tgttggtggt tcggcaagg tttacagagg 1801 agagattgat ggcggaacta caaaggtagc catcaagaga ggcaacccaa tgtccgagca 1861 aggtgtacat gagttccaga ctgagattga aatgcttttca aagcttagac atcgtcatct 1921 tgtgtccttg attggatact gtgaagagaa ctgcgaaatg atcttagtct atgattacat 1981 ggctcatggt acaatgaggg agcatctcta caaaacccag aatccttctc ttccatggaa 2041 gcaacgtctt gagatatgca ttggagcagc ccgaggttta cactatctac acactggtgc 2101 aaaacacaca atcatccata gagatgtgaa gacaacaaac attctattgg atgagaaatg 2161 ggtggccaag gtctctgatt ttggtctatc gaagactggt cctacactag accacacaca 2221 cgtaagcaca gttgtgaaag gaagtttcgg ttatcttgac ccagagtatt tcagacggca 2281 gcaactgact gagaaatccg atgtctactc ctttggcgtt gttctattcg aagctctatg 2341 cgctcgtcca gccttgaacc caacacttgc aaaggaacaa gtgagcttag ctgagtgggc 2401 accatactgc tacaagaaag gcatgctaga tcaaatcgtt gatccctacc tcaagggcaa 2461 gatcacacca gaatgcttca aaaagtttgc tgaaaccgcg atgaagtgtg ttctagacca 2521 gggcattgag agaccatcaa tgggagatgt tctgtggaac ttagaatttg cgttgcagct 2581 ccaggaaagc gcagaagaga acggaaaagg agtatgcggt gacatggaca tggatgagat 2641 taagtacgat gatggaaact gtaaaggaaa gaacgacaag agttctgatg tgtatgaagg 2701 gaatgtgacg gactcgagga gcagtggaat agatatgagc atcggtggta ggagtttggc 2761 cagcgaagat tcagatggac tcactccaag tgctgtgttt tctcagatca tgaatccaaa 2821 gggacgttag agaagtctta taacacggta caacactact acctttctaa accggctcca 2881 tccaaaggag accggttcgt ttctcttttt tatattttt ttcctcttaa ctatttatta 2941 ttattctctt tgctgttatt tatttagaat tttggatttg tgtatttgat gccacgatgg 3001 agagtgtaaa aaataatgta ttttttttc ttctttctac aaaaacatta aacatgaatc 3061 gcgtcaatgt actatttggt ttgttatcta taacgttttt ggtaattgtt gcatctttac 3121 tct
```

*Arabidopsis thaliana* THE1 (THESEUS1); kinase; protein kinase (THE1) mRNA, complete cds
LOCUS       NM_124818               2789 bp    mRNA    linear   PLN 21-AUG-2009
DEFINITION  *Arabidopsis thaliana* THE1 (THESEUS1); kinase/ protein kinase (THE1)
            mRNA, complete cds.
ACCESSION   NM_124818
VERSION     NM_124818.3  GI:42568527

```
KEYWORDS   .
SOURCE     Arabidopsis thaliana (thale cress)
 ORGANISM  Arabidopsis thaliana
           Eukaryota; Viridiplantae; Streptophyta; Embryophyta; Tracheophyta;
           Spermatophyta; Magnoliophyta; eudicotyledons; core eudicotyledons;
           rosids; eurosids II; Brassicales; Brassicaceae; Arabidopsis.
COMMENT    REVIEWED REFSEQ: This record has been curated by TAIR. The
           reference sequence was derived from AT5G54380.1.
           On Feb 17, 2004 this sequence version replaced gi:30696448.
FEATURES          Location/Qualifiers
  source          1..2789
                  /organism="Arabidopsis thaliana"
                  /mol_type="mRNA"
                  /db_xref="taxon:3702"
                  /chromosome="5"
                  /ecotype="Columbia"
  gene            1..2789
                  /gene="THE1"
                  /locus_tag="AT5G54380"
                  /gene_synonym="GA469.3; GA469_3; THE1; THESEUS1"
                  /db_xref="GeneID:835526"
                  /db_xref="TAIR:AT5G54380"
  CDS             1..2568
                  /gene="THE1"
                  /locus_tag="AT5G54380"
                  /gene_synonym="GA469.3; GA469_3; THE1; THESEUS1"
                  /note="THESEUS1 (THE1); FUNCTIONS IN: protein kinase
                  activity, kinase activity; INVOLVED IN: protein amino acid
                  autophosphorylation; LOCATED IN: plasma membrane;
                  EXPRESSED IN: 26 plant structures; EXPRESSED DURING: 13
                  growth stages; CONTAINS InterPro DOMAIN/s: Protein kinase,
                  ATP binding site (InterPro:IPR017441), Protein kinase,
                  core (InterPro:IPR000719), Serine/threonine protein
                  kinase-related (InterPro:IPR017442), Protein kinase-like
                  (InterPro:IPR011009), Serine/threonine protein kinase,
                  active site (InterPro:IPR008271); BEST Arabidopsis
                  thaliana protein match is: protein kinase, putative
                  (TAIR:AT3G46290.1); Has 83452 Blast hits to 82490 proteins
                  in 3283 species: Archae - 46; Bacteria - 7218; Metazoa -
                  37262; Fungi - 6478; Plants - 18497; Viruses - 351; Other
                  Eukaryotes - 13600 (source: NCBI BLink)."
                  /codon_start=1
                  /product="THE1 (THESEUS1); kinase/ protein kinase"
                  /protein_id="NP_200249.1"
                  /db_xref="GI:15239630"
                  /db_xref="GeneID:835526"
                  /db_xref="TAIR:AT5G54380"
                  /translation=
SEQ ID NO: 4
"MVFTKSLLVLLWFLSCYTTTTSSALFNPPDNYLISCGSSQNITF

QNRIFVPDSLHSSLVLKIGNSSVATSTTSNNSTNSIYQTARVFSSLASYRFKITSLGR

HWIRLHFSPINNSTWNLTSASITVVTEDFVLLNNFSFNNFNGSYIFKEYTVNVTSEFL

TLSFIPSNNSVVFVNAIEVVSVPDNLIPDQALALNPSTPFSGLSLLAFETVYRLNMGG

PLLTSQNDTLGRQWDNDAEYLHVNSSVLVVTANPSSIKYSPSVTQETAPNMVYATADT

MGDANVASPSFNVTWVLPVDPDFRYFVRVHFCDIVSQALNTLVFNLYVNDDLALGSLD

LSTLTNGLKVPYFKDFISNGSVESSGVLTVSVGPDSQADITNATMNGLEVLKISNEAK

SLSGVSSVKSLLPGGSGSKSKKKAVIIGSLVGAVTLILLIAVCCYCCLVASRKQRSTS

PQEGGNGHPWLPLPLYGLSQTLTKSTASHKSATASCISLASTHLGRCFMFQEIMDATN

KFDESSLLGVGGFGRVYKGTLEDGTKVAVKRGNPRSEQGMAEFRTEIEMLSKLRHRHL

VSLIGYCDERSEMILVYEYMANGPLRSHLYGADLPPLSWKQRLEICIGAARGLHYLHT

GASQSIIHRDVKTTNILLDENLVAKVADFGLSKTGPSLDQTHVSTAVKGSFGYLDPEY

FRRQQLTEKSDVYSFGVVLMEVLCCRPALNPVLPREQVNIAEWAMAWQKKGLLDQIMD

SNLTGKVNPASLKKFGETAEKCLAEYGVDRPSMGDVLWNLEYALQLEETSSALMEPDD

NSTNHIPGIPMAPMEPFDNSMSIIDRGGVNSGTGTDDDAEDATTSAVFSQLVHPRGR"

ORIGIN
SEQ ID NO: 3
```

-continued

```
   1 atggtgttca caaaatcatt acttgttctt ctttggttcc tctcttgtta cactactact
  61 acttcatcag ctttgtttaa tccgccagac aattacttga tctcttgtgg ctcatcacaa
 121 aacataactt tccaaaacag aatctttgtt ccagattcac tccactcttc tcttgtactc
 181 aaaatcggaa actcttctgt tgcaacatca actacttcca acaattcaac caattccatc
 241 taccaaaccg ctcgtgtttt ctccagttta gcttcttaca gattcaaaat cacttcttta
 301 ggtcgacatt ggatccgtct tcatttctca cctatcaaca actctacttg aacttaacc
 361 tctgcttcaa tcactgtcgt aacagaagac ttcgtgctct tgaacaactt ctccttcaac
 421 aacttcaacg gttcttacat cttcaaagag tacacagtca atgtcacttc agagttcttg
 481 actttaagtt tcattccttc aaacaattcg gtggtctttg tcaacgctat tgaagttgtc
 541 tctgttccgg ataatcttat ccctgatcaa gctttggcgt taaacccttc aacaccattt
 601 agtggtctct ctctgcttgc atttgaaaca gtctacagat taaatatggg aggaccattg
 661 ttgacttctc aaaacgatac attggggaga caatgggata atgatgcaga gtatcttcat
 721 gtgaacagct ctgttcttgt tgtaacggcg aatccttctt cgattaagta ctctccttct
 781 gtgactcaag aaacagctcc taacatggtt tatgcaactg ctgatacaat gggtgatgct
 841 aatgttgcga gtccaagttt taatgttact tgggttcttc ctgttgatcc agacttcagg
 901 tactttgttc gtgttcattt ctgtgatatt gtgagtcaag ctttgaacac gcttgttttc
 961 aatctttatg tgaatgatga tcttgctctt ggaagtcttg atctctctac gttgactaat
1021 ggtcttaaag ttccttactt taaggatttt atctccaatg gttctgttga atcttccggt
1081 gttttaaccg ttagcgttgg acctgattca caagctgata tcactaatgc gactatgaat
1141 gggttagagg ttttgaagat tagtaacgaa gctaagagct aagtggtgt ttcttcggtt
1201 aagtcgttac ttccgggagg atcaggttct aagagcaaga agaaggcagt gatcattggt
1261 tctttggttg gtgcggttac attgattctg ctgattgctg tttgttgcta ttgctgtttg
1321 gttgcttcaa ggaagcagag gtcgacgagt cctcaagaag gcggtaatgg acatccgtgg
1381 ttgccattac ctttatatgg actctctcag actcttacta aatcaaccgc ttctcacaag
1441 agtgccacag ctagttgcat tcattagct tctactcatc ttggacgttg ctttatgttt
1501 caagaaatca tggacgctac taataagttc gatgagagtt cgttgcttgg ggttggtgga
1561 tttggccgcg tttataaagg aactttagaa gacgggacta aagtcgcggt taaagaggt
1621 aacccgagat cagaacaagg tatggctgag ttcagaacag agattgaaat gctgtcaaaa
1681 ctcagacatc gacatctcgt ctctcttatc ggttactgcg acgagaggtc tgaaatgata
1741 ctggtctatg agtacatggc gaatggaccg ttgaggagtc atctatatgg agctgatctt
1801 cctccattgt cttggaaaca aagactcgag atttgcatcg gtgcagcgag aggattacat
1861 tatctacaca ccggtgcatc gcagagcatt atacaccgtg atgttaaaac cacgaatatc
1921 ttactcgacg agaatctagt cgccaaagtt gcagactttg gactatccaa accggccct
1981 tcgctcgatc aaacacacgt gagcacggcg gttaaggaa gctttggtta tctagacccg
2041 gaatacttca ggagacagca gttaacagag aaatcagacg tttattcgtt tggtgttgta
2101 ctaatggaag tactctgttg tagaccggct ttaaacccgg tattacctag agaacaagtg
2161 aacatagcgg aatgggcaat ggcgtggcag aaaaagggtc tgctagatca aatcatggac
2221 agtaacttaa ccggaaggt gaaccctgcc tcgttgaaga aatttggaga accgcagag
2281 aaatgtttag cggaatacgg tgtggaccgg ccttctatgg agatgtatt gtggaatttg
2341 gagtacgcgt tacagctaga agaaacatct tcggctttga tggagcctga tgacaatagt
2401 acaaaccaca ttccagggat tccaatggcg ccaatggaac cgtttgataa cagtatgagt
```

```
2461 ataatcgata gaggaggagt aaattcgggg accgggactg atgatgatgc ggaagacgcg 2521 actactagtg cggtgttttc gcagcttgtt catcctcgtg gaaggtagaa gaagaacaca 2581 tttggtgaaa acaacagcag agacagacat tgtttgtttt tgaaaaattt atagaaagaa 2641 agttatttat tgaagacttt tgggaacaaa caacaaaatg attcattcag catttatttt 2701 cgattttta cggtgtattt gttttgtaat atagtgagta ctgatgtttt aaagcaaatc 2761 atgaatcaga atgtgattat atatcttaa
//
```

HERK I
LOCUS NM_114497 2779 bp mRNA linear PLN 21-AUG-2009
DEFINITION Arabidopsis thaliana protein kinase, putative
(AT3G46290) mRNA,
    complete cds.
ACCESSION NM_114497
VERSION NM_114497.2 GI:30692702
KEYWORDS .
SOURCE Arabidopsis thaliana (thale cress)
 ORGANISM Arabidopsis thaliana
    Eukaryota; Viridiplantae; Streptophyta; Embryophyta; Tracheophyta;
    Spermatophyta; Magnoliophyta; eudicotyledons; core eudicotyledons;
    rosids; eurosids II; Brassicales; Brassicaceae; Arabidopsis.
COMMENT REVIEWED REFSEQ: This record has been curated by TAIR. The
    reference sequence was derived from AT3G46290.1.
    On May 13, 2003 this sequence version replaced gi: 18408176.
FEATURES       Location/Qualifiers
  source    1..2779
        /organism="Arabidopsis thaliana"
        /mol_type="mRNA"
        /db_xref="taxon:3702"
        /chromosome="3"
        /ecotype="Columbia"
  gene     1..2779
        /locus_tag="AT3G46290"
        /db_xref="GeneID:823774"
        /db_xref="TAIR:AT3G46290"
  CDS      1..2493
        /locus_tag="AT3G46290"
        /note="protein kinase, putative; FUNCTIONS IN: kinase
        activity; INVOLVED IN: protein amino acid phosphorylation;
        LOCATED IN: plasma membrane; EXPRESSED IN: 24 plant
        structures; EXPRESSED DURING: 12 growth stages; CONTAINS
        InterPro DOMAIN/s: Protein kinase, ATP binding site
        (InterPro:IPR017441), Protein kinase, core
        (InterPro:IPR000719), Tyrosine protein kinase
        (InterPro:IPR001245), Protein kinase-like
        (InterPro:IPR011009), Serine/threonine protein kinase,
        active site (InterPro:IPR008271); BEST Arabidopsis
        thaliana protein match is: protein kinase, putative
        (TAIR:AT5G59700.1); Has 84021 Blast hits to 83080 proteins
        in 3289 species: Archae - 46; Bacteria - 7437; Metazoa -
        37100; Fungi - 6558; Plants - 18598; Viruses - 354; Other
        Eukaryotes - 13928 (source: NCBI BLink)."
        /codon_start=1
        /product="protein kinase, putative"
        /protein_id=" NP_190214.1"
        /db_xref="GI:15231393"
        /db_xref="GeneID: 823774"
        /db_xref="TAIR:AT3G46290"
        /translation=
SEQ ID NO: 6
"MGIEKFETFILISTISILLCICHGFTPVDNYLINCGSPTNGTLM

GRIFLSDKLSSKLLTSSKEILASVGGNSGSDIYHTARVFTEVSSYKFSVTRGRHWVRL

YFNPFDYQNPFKMGSAKFAVSSQSHVLLSDFTVTSSKVVKEYSLNVTTNDLVLTFTPSS

GSFAFVNAIEVISIPDTLITGSPRFVGNPAQFPDMSMQGLETIHRVNMGGPLVASNND

TLTRTWVPDSEFLLEKNLAKSMSKFSTVNFVPGYATEDSAPRTVYGSCTEMNSADNPN

SIFNVTWEFDVDPGFQYYFRFHFCDIVSLSLNQLYFNLYVDSMVAATDIDLSTLVDNT

LAGAYSMDFVTQTPKGSNKVRVSIGPSTVHTDYPNAIVNGLEIMKMNNSKGQLSTGTF

-continued

VPGSSSSSKSNLGLIVGSAIGSLLAVVFLGSCFVLYKKRKRGQDGHSKTWMPFSINGT
SMGSKYSNGTTLTSITTNANYRIPFAAVKDATNNFDESRNIGVGGFGKVYKGELNDGT
KVAVKRGNPKSQQGLAEFRTEIEMLSQFRHRHLVSLIGYCDENNEMILIYEYMENGTV
KSHLYGSGLPSLTWKQRLEICIGAARGLHYLHTGDSKPVIHRDVKSANILLDENFMAK
VADFGLSKTGPELDQTHVSTAVKGSFGYLDPEYFRRQQLTDKSDVYSFGVVLFEVLCA
RPVIDPTLPREMVNLAEWAMKWQKKGQLDQIIDQSLRGNIRPDSLRKFAETGEKCLAD
YGVDRPSMGDVLWNLEYALQLQEAVIDGEPEDNSTNMIGELPPQINNFSQGDTSVNVP
GTAGRFEESSIDDLSGVSMSKVFSQLVKSEGR"

```
ORIGIN
SEQ ID NO: 5
    1 atgggtattg aaaagtttga aactttcatc ttgatttcaa cgatttcgat cttgctttgt
   61 atctgccatg gattcacacc tgtggataat tacttgatca actgtggatc accaaccaat
  121 ggaacactaa tgggtcgaat ctttctgtct gataagctct cttcgaagtt acttacttcg
  181 tccaaagaga ttctcgcaag cgtaggcggt aactctggct cagacattta ccacacggca
  241 agagtcttca ccgaagtctc tagctacaaa ttctcggtca ctcgtggtcg tcattgggtt
  301 cgtctctatt tcaatccttt tgactaccaa aacttcaaaa tgggttcagc taaattcgcg
  361 gtttcttcac aaagtcatgt cctttgagt gatttcactg ttacgagttc aaaagttgtc
  421 aaagagtact ctttgaacgt gactactaat gatttagtgc tcacctttac ccctctagt
  481 ggttcgtttg cgtttgtgaa tgctatcgag gttatatcga ttccagatac tttgattact
  541 ggtagtccaa ggtttgtagg caaccctgcg cagtttccgg atatgtcaat gcaaggtctt
  601 gaaaccattc atagagtcaa catgggtggt ccgcttgttg cgtctaacaa cgatacgtta
  661 acgagaactt gggtgcctga ctcggagttt ctgcttgaga gaatttagc taagagtatg
  721 tctaagtttt caactgttaa ctttgttcca ggttatgcaa cagaggactc tgctccaaga
  781 actgtctatg gtagttgtac tgagatgaat ccgctgata acccgaatag cattttcaat
  841 gtgacttggg agttcgatgt tgacccgggt tttcagtact atttccgctt tcatttctgc
  901 gatatcgtta gcttgtcgtt aaaccagcta tatttcaatc tttatgttga ctcaatggtt
  961 gctgctacgg atattgatct tagcactctt gtggataaca ctttggctgg tgcatattcg
 1021 atggactttg tcacgcagac gccaaagggt agtaataaag tccgtgtgag catcggtccg
 1081 tcgactgttc acaccgatta tccaaacgcg attgtgaatg gattggagat tatgaagatg
 1141 aataactcta agggtcagtt aagcactggg acatttgtgc ctggtagtag ttcaagcagt
 1201 aagagtaatc tcgggttgat tgtaggttca gccattggtt cgttgctcgc ggtagtcttc
 1261 ttgggaagtt gcttttgtgtt gtataagaag cggaaacgtg gccaagacgg tcattcaaag
 1321 acttggatgc cgttttcgat aaatggaact tcgatgggaa gcaaatactc caatggaact
 1381 acgcttacaa gtataactac caatgccaat taccgtattc cctttgcagc ggttaaagac
 1441 gctacaaata actttgacga gagccgcaac atcggtgtag cggttttgg taaagtctac
 1501 aaaggagagc ttaatgacgg tacaaaggta gctgtgaaaa gagggaaccc aaaatctcag
 1561 caagggcttg cggaattcag gacagaaatc gagatgttat ctcagtttcg tcaccgccat
 1621 ttggtttctc tgatcggtta ttgtgacgag aacaatgaga tgatactaat ttacgagtat
 1681 atggagaatg gaacggtaaa gagtcatctt tatggctcag gtctacctag cttgacttgg
 1741 aaacaacggc ttgagatctg cattggtgca gctagaggct tgcattacct tcacacgggt
 1801 gactcgaaac cggtcattca cagagacgtg aaatctgcaa acatattgct tgacgagaac
```

-continued

```
1861 ttcatggcta aagttgcaga ctttggactg tccaagactg gacccgagct tgatcagact 1921 catgtaagta ctgctgtcaa aggaagtttt ggttatcttg accccgagta cttcagaagg 1981 caacagctca cagataaatc cgatgtttat tccttcggag ttgttctctt cgaggtttta 2041 tgtgctagac ctgttataga cccaacactt ccaagagaga tggtgaatct tgcagaatgg 2101 gctatgaaat ggcagaagaa agggcaactg gatcagatca tcgaccagtc gcttcgcgga 2161 aatatcagac ccgattcgtt aaggaaattt gcggaaacag gtgagaaatg tttagcggat 2221 tatggagttg ataggccatc tatgggagat gtgttgtgga atcttgaata cgctctgcag 2281 cttcaagaag cagtcattga tggtgaacca gaagataata gcacgaatat gattggtgaa 2341 ttacctccgc agatcaataa tttcagtcag ggagacacta gtgttaacgt tccgggcaca 2401 gcggggcgat tcgaggaatc tagtattgat gatctctctg gcgtttccat gagtaaagta 2461 ttctcacaac tggtgaaatc tgaaggaaga tagtgaaaga tttgagcaat gcagtgccaa 2521 gaaaagccaa agatctgatc tttttgatag aaacagagca agcaaagtat gtaaccagga 2581 aaaaagcatc aggttatttt cagataggat ctttgtcttt gcttgatctg tttctactgc 2641 agatttttca tcagtgatta aacggttact ttgaaaattt accttatttt gttcctctct 2701 cccttatcct gagtttgtat tttattgatg ttcattttga aattgtctga aatttgtttg 2761 ttcttttttac tatatggat
//
```

HERK II
Arabidopsis thaliana protein kinase family protein (AT1G30570) mRNA, complete cds
LOCUS       NM_102794               2550 bp    mRNA    linear   PLN 21-AUG-2009
DEFINITION  Arabidopsis thaliana protein kinase family protein (AT1G30570)
            mRNA, complete cds.
ACCESSION   NM_102794
VERSION     NM_102794.1  GI:18397570
KEYWORDS    .
SOURCE      Arabidopsis thaliana (thale cress)
  ORGANISM  Arabidopsis thaliana
            Eukaryota; Viridiplantae; Streptophyta; Embryophyta; Tracheophyta;
            Spermatophyta; Magnoliophyta; eudicotyledons; core eudicotyledons;
            rosids; eurosids II; Brassicales; Brassicaceae; Arabidopsis.
COMMENT     REVIEWED REFSEQ: This record has been curated by TAIR. The
            reference sequence was derived from AT1G30570.1.
FEATURES             Location/Qualifiers
     source          1..2550
                     /organism="Arabidopsis thaliana"
                     /mol_type="mRNA"
                     /db_xref="taxon:3702"
                     /chromosome="1"
                     /ecotype="Columbia"
     gene            1..2550
                     /locus_tag="AT1G30570"
                     /gene_synonym="T5I8.2; T5I8_2"
                     /db_xref="GeneID:839937"
                     /db_xref="TAIR:AT1G30570"
     CDS             1..2550
                     /locus_tag="AT1G30570"
                     /gene_synonym="T5I8.2; T5I8_2"
                     /note="protein kinase family protein; FUNCTIONS IN: kinase
                     activity; INVOLVED IN: protein amino acid phosphorylation;
                     LOCATED IN: plasma membrane; EXPRESSED IN: 20 plant
                     structures; EXPRESSED DURING: 12 growth stages; CONTAINS
                     InterPro DOMAIN/s: Protein kinase, ATP binding site
                     (InterPro:IPR017441), Protein kinase, core
                     (InterPro:IPR000719), Tyrosine protein kinase
                     (InterPro:IPR001245), Protein kinase-like
                     (InterPro:IPR011009), Serine/threonine protein kinase,
                     active site (InterPro:IPR008271); BEST Arabidopsis
                     thaliana protein match is: THE1 (THESEUS1); kinase/
                     protein kinase (TAIR:AT5G54380.1); Has 82566 Blast hits to
                     81527 proteins in 3120 species: Archae - 48; Bacteria -
                     7102; Metazoa - 36469; Fungi - 6499; Plants - 18648;
                     Viruses - 325; Other Eukaryotes - 13475 (source: NCBI -continued

```
                BLink)."
                /codon_start=1
                /product="protein kinase family protein"
                /protein_id="NP_174345.1"
                /db_xref="GI:15221443"
                /db_xref="GeneID:839937"
                /db_xref="TAIR:AT1G30570"
                /translation=
SEQ ID NO: 8
"MSKLRKKYLEHLLCVLIFFTYVIGYGEAQSKSFLVDCGSNATTE

VDGRTWVGDLSPNKSVTLQGFDAITASTSKGSSVYAEIYKTARVFDAVLNYTFEGITQ

GNYFVRLHFSPFAIENHNVNESSFSVFADGLRLMLDINIAGEIAHKNLILESTGHNAT

ASSLVKEFLLPTGPGKLVLSFIPEKGSFGFVNAIEIVSVDDKLFKESVTKVGGSEVEL

GLGGRGIETMYRLNVGGPKLGPSKDLKLYRTWETDLSYMVIENAGVEVKNSSNITYAL

ADDSPVAPLLVYETARMMSNTEVLEKRFNISWKFEVDPNFDYLVRLHFCELLVDKQNQ

RIFRIYINNQTAAGNFDIFAHAGGKNKGIYQDYLDPVSSKNDVLWIQLGPDSSVGASG

DALLSGLEIFKLSKNGNLAHLIRFDSTGHSVSDSKMRIIWISVGAGIAIIIFFVFLGI

LVVCLCKKRRSKSDESKNNPPGWRPLFLHVNNSTANAKATGGSLRLNTLAASTMGRKF

TLAEIRAATKNFDDGLAIGVGGFGKVYRGELEDGTLIAIKRATPHSQQGLAEFETEIV

MLSRLRHRHLVSLIGFCDEHNEMILVYEYMANGTLRSHLFGSNLPPLSWKQRLEACIG

SARGLHYLHTGSERGIIHRDVKTTNILLDENFVAKMSDFGLSKAGPSMDHTHVSTAVK

GSFGYLDPEYFRRQQLTEKSDVYSFGVVLFEAVCARAVINPTLPKDQINLAEWALSWQ

KQRNLESIIDSNLRGNYSPESLEKYGEIAEKCLADEGKNRPMMGEVLWSLEYVLQIHE

AWLRKQNGENSFSSSQAVEEAPESFTLPACSNQDSSETEQSQTGSALHNSA"

ORIGIN
SEQ ID NO: 7
   1 atgtcgaagc tgaggaaaaa gtatctggaa catcttctat gtgtgttgat tttctttact
  61 tatgttattg gctatggaga agctcagtcc aagagcttcc ttgtagattg tggctcaaat
 121 gctacaaccg aagtagatgg aagaacatgg gttggtgatt tatctcccaa caagagtgtg
 181 accctgcaag gatttgatgc cattactgct tcgacatcga aggaagttc tgtttacgct
 241 gagatatata agactgctcg tgttttcgac gctgtgttga actatacatt tgaaggtata
 301 actcaaggga attactttgt taggctccat ttcagccctt cgctattga aaaccacaat
 361 gtgaatgagt cttctttcag cgtctttgcg gatggtctga gactgatgct tgacatcaac
 421 atcgcgggag aaatcgcgca taagaatctc atcttggaaa gcactggtca caatgctact
 481 gcctcttctt tggttaaaga gtttctgtta cctactggac aggaaaaact ggttttaagt
 541 ttcatcccgg agaagggtc tttcgggttt gtcaatgcta ttgagatagt ctctgttgat
 601 gataagcttt taaggaatc agttactaaa gttggtggaa gtgaagtgga gcttggtttg
 661 ggtggacgag ggattgaaac tatgtatagg ctaaacgttg gtggtcccaa gctaggtcca
 721 agcaaagatc ttaagcttta tagaacatgg gaaacagatt taagctacat ggtgattgag
 781 aacgctggtg tagaagtcaa gaacagctca aatatcacat atgctttggc tgatgattct
 841 cctgtggctc ctcttcttgt ttatgaaact gctaggatga tgtcaaacac tgaagtcttg
 901 gagaaacggt tcaacatttc ttggaagttt gaagttgatc ctaatttcga ctacttggtt
 961 aggcttcatt tctgtgagct tcttgttgat aagcaaaacc agaggatttt caggatatac
1021 ataaacaacc agacggctgc tggtaatttc gatatatttg ctcacgcggg cgggaagaac
1081 aaaggtatat atcaagatta cttggatccg gtctcctcta agaacgacgt tctctggatt
1141 caacttggac ctgactcatc tgttggtgct tctggagacg ctcttctgag tggtcttgag
```

-continued

```
1201 attttcaagc tcagcaaaaa tgggaatctt gctcatctca tcaggtttga ttcgactggt 1261 cactcggtaa gtgactcgaa gatgcggatt atttggatca gtgttggtgc tggtatagca 1321 attatcattt ttttcgtgtt cttgggaatc ttggtagtat gtttatgcaa gaaaaggcga 1381 agcaaatcag atgagtcgaa aaacaatcct cccgggtggc gtccgttgtt tttgcatgtc 1441 aataacagta ctgcaaacgc caaagcaacg ggaggctcgc tgagactgaa cactcttgca 1501 gcatctacaa tgggaaggaa gtttacacta gccgagattc gtgcagcaac taagaacttt 1561 gatgatggtt tagctattgg agttggaggg tttggtaagg tttacagagg agagcttgaa 1621 gatggaacac tcatagctat aaaacgagcc accccacatt ctcagcaagg gcttgctgaa 1681 ttcgaaaccg agatcgtgat gctctcaaga cttaggcata ggcatcttgt gtctttgatc 1741 gggttctgcg atgagcacaa tgagatgatc ttggtttatg aatacatggc aaatggaact 1801 ctcaggagtc atctctttgg aagcaacctt ccgccattat catggaagca acggcttgaa 1861 gcttgtatag gctctgcgag aggattgcat taccttcaca cagggtcaga gagaggaatc 1921 attcacagag atgtcaaaac aacaaacata ctattagacg agaactttgt ggcaaagatg 1981 tctgattttg ggctgtcgaa agctggaccg tccatggacc atactcatgt gagtacagct 2041 gtgaaaggaa gttttggtta tcttgatcct gaatacttta gaaggcaaca gttaacagag 2101 aagtcagatg tttactcttt tggtgttgtg ttgttcgaag ctgtttgtgc tcgagctgtt 2161 ataaacccaa ctttgcctaa agaccagatc aaccttgcgg aatgggcttt aagctggcaa 2221 aaacagagaa acctcgagtc catcatcgac tcaaatctga ggggaaacta cagtcctgaa 2281 tcgttggaga agtatgggga gatagcagag aagtgcttag cggatgaagg gaagaacagg 2341 ccaatgatgg gagaagtgtt atggagcttg gagtatgttt tgcagattca tgaagcttgg 2401 cttcgcaaac agaatggaga aaactcgttt tcgagcagcc aagcggtaga agaagcacca 2461 gagagcttta ctcttccagc ttgttccaat caagattcct cagaaactga gcagagccaa 2521 acaggatctg ctcttcacaa ttcggcttag
//
```

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention as described in the appended claims.

What is claimed is:

1. A genetically modified plant having increased plant growth and cellular elongation comprising:
a heterologous polynucleotide sequence which encodes a CrRLK1L receptor like kinase polypeptide operably linked to a promoter sequence, wherein said CrRLK1L receptor like kinase is HERCULES 1 Receptor Kinase 1 (HERK1),
wherein said HERK1 comprises one or more of the following sequences:
(a) a nucleic acid comprising the polynucleotide sequence of SEQ ID NO: 5, or a complete complement thereof;
(b) a nucleic acid comprising at least 99% sequence identity to SEQ ID NO: 5, or a complete complement thereof;
(c) a nucleic acid encoding a polypeptide sequence at least 95% identical to SEQ ID NO: 6, wherein said sequences are operably linked to a promoter,
wherein said CrRLK1L receptor like kinase activity is increased, and wherein said modified plant has increased plant growth and cellular elongation when compared to a nonmodified plant.

2. Seed of the plant of claim 1 wherein said seed comprises the heterologous polynucleotide sequence which encodes a CrRLK1L receptor like kinase polypeptide operably linked to a promoter sequence, wherein said CrRLK1L receptor like kinase is HERK1.

3. A method for increasing plant growth and cellular elongation comprising:
increasing the activity of a CrRLK1L receptor like kinase in a plant, wherein said CrRLK1L receptor like kinase HERCULES 1 Receptor Kinase 1 (HERK1);
introducing into the plant an expression cassette comprising a HERK1 nucleic acid operably linked to a promoter that functions in plants, wherein said CrRLK1L receptor like kinase activity is increased;
wherein said HERK1 comprises one or more of the following sequences:
(a) a nucleic acid comprising the polynucleotide sequence of SEQ ID NO: 5, or a complete complement thereof;
(b) a nucleic acid encoding a polypeptide sequence at least 95% identical to SEQ ID NO: 6, wherein said sequences are operably linked to a promoter; and
selecting for plants that have increased plant growth or cellular elongation.

4. The method of claim 3, wherein said CrRLK1L receptor like kinase activity is increased by increasing the expression of said HERK1 nucleic acid.

5. The method of claim 3, wherein the expression cassette is introduced by a method selected from the group consisting of: electroporation, micro-projectile bombardment and *Agrobacterium*-mediated transfer.

6. The method of claim 3 wherein the promoter that functions in plants is a tissue-preferred promoter, tissue-specific promoter or an inducible promoter.

7. The method of claim 3 wherein the plant is *Arabidopsis*, wheat, rice, sorghum, barley, oat, lawn grass, rye, soybean, canola, *Brassica*, sunflower, maize, sorghum, alfalfa, cotton, millet, peanut or cacao.

8. A method for increasing plant growth comprising, introducing to said plant an expression construct comprising a CrRLK1L receptor like kinase of one or more of the following sequences:
   (a) a nucleic acid comprising the polynucleotide sequence of SEQ ID NO: 5 or a complete complement thereof;
   (b) a nucleic acid comprising at least 99% sequence identity to SEQ ID NO: 5 or a complete complement thereof;
   (c) a nucleic acid encoding the polypeptide sequence of SEQ ID NO: 6; wherein said sequences are operably linked to a promoter; wherein said CrRLK1L receptor like kinase activity is increased; and selecting for plants that have increased plant growth.

9. The method of claim 8 wherein said promoter is a tissue specific promoter.

* * * * *